United States Patent
Cappola et al.

(10) Patent No.: US 10,987,105 B2
(45) Date of Patent: *Apr. 27, 2021

(54) SURGICAL APPARATUS

(71) Applicant: Covidien LP, Mansfield, MA (US)

(72) Inventors: Kenneth Cappola, Monroe, CT (US); Frank Maffei, Shelton, CT (US); Lee Ann Olson, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 229 days.

This patent is subject to a terminal disclaimer.

(21) Appl. No.: 16/171,806

(22) Filed: Oct. 26, 2018

(65) Prior Publication Data

US 2019/0059899 A1 Feb. 28, 2019

Related U.S. Application Data

(63) Continuation of application No. 14/811,938, filed on Jul. 29, 2015, now Pat. No. 10,130,367.

(Continued)

(51) Int. Cl.
*A61B 17/068* (2006.01)
*A61B 17/10* (2006.01)
(Continued)

(52) U.S. Cl.
CPC .......... *A61B 17/105* (2013.01); *A61B 17/068* (2013.01); *A61B 17/07207* (2013.01); *A61B 90/90* (2016.02); *A61B 90/98* (2016.02); *A61B 2017/00398* (2013.01); *A61B 2017/00473* (2013.01); *A61B 2017/00477* (2013.01); *A61B 2017/00951* (2013.01);

(Continued)

(58) Field of Classification Search
CPC ...................................................... A61B 90/90
USPC ....................................................... 227/176.1
See application file for complete search history.

(56) References Cited

U.S. PATENT DOCUMENTS 3,079,606 A 3/1963 Bobrov et al.
3,490,675 A 1/1970 Green et al.
(Continued)

FOREIGN PATENT DOCUMENTS

AU 198654765 9/1986
CA 2773414 A1 11/2012
(Continued)

OTHER PUBLICATIONS

Chinese Second Office Action dated Mar. 9, 2020, issued in CN Appln. No. 201610109472, 6 pages.
(Continued)

*Primary Examiner* — Michelle Lopez
(74) *Attorney, Agent, or Firm* — Carter, DeLuca & Farrell LLP

(57) ABSTRACT

A surgical apparatus including an electrical conductor with a strain relief is provided. A tool assembly is supported on a body portion and is articulable relative to the body portion. The tool assembly includes an identification assembly in electrical communication with a powered handle assembly. An electrical conductor extends from a connection assembly in the body portion to the identification assembly. The electrical conductor includes a strain relief portion for accommodating the articulation of the tool assembly relative to the body portion.

21 Claims, 37 Drawing Sheets

Related U.S. Application Data

(60) Provisional application No. 62/121,049, filed on Feb. 26, 2015.

(51) Int. Cl.

| | | |
|---|---|---|
| *A61B 17/072* | (2006.01) | |
| *A61B 90/90* | (2016.01) | |
| *A61B 90/98* | (2016.01) | |
| A61B 17/00 | (2006.01) | |
| A61B 17/29 | (2006.01) | |
| A61B 90/00 | (2016.01) | |

(52) U.S. Cl.
CPC ........... *A61B 2017/07271* (2013.01); *A61B 2017/07278* (2013.01); *A61B 2017/07285* (2013.01); *A61B 2017/2927* (2013.01); *A61B 2090/038* (2016.02); *A61B 2090/0808* (2016.02)

(56) References Cited

U.S. PATENT DOCUMENTS

| | | |
|---|---|---|
| 3,499,591 A | 3/1970 | Green |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,241,861 A | 12/1980 | Fleischer |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |

(56) References Cited

U.S. PATENT DOCUMENTS

| | | |
|---|---|---|
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,279,809 B1 | 8/2001 | Nicolo |
| 6,315,183 B1 | 11/2001 | Piraka |

(56) References Cited

U.S. PATENT DOCUMENTS

| | | |
|---|---|---|
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,612,053 B2 | 9/2003 | Liao |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,808,262 B2 | 10/2004 | Chapoy et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |

(56) References Cited

U.S. PATENT DOCUMENTS

| | | |
|---|---|---|
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,796 B2 | 10/2010 | Blake et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |

(56) References Cited

U.S. PATENT DOCUMENTS

| | | |
|---|---|---|
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Rommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,276 B2 | 4/2011 | Guignard et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |

(56) References Cited

U.S. PATENT DOCUMENTS

| | | |
|---|---|---|
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |

(56) References Cited

U.S. PATENT DOCUMENTS

| | | |
|---|---|---|
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | (Prommersberger) Stopek et al. |
| 8,627,994 B2 | 1/2014 | Zemlok et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,757,465 B2 | 6/2014 | Woodard, Jr. et al. |
| 8,758,391 B2 | 6/2014 | Swayze et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 10,085,749 B2 * | 10/2018 | Cappola ............... A61B 17/072 |
| 10,130,367 B2 * | 11/2018 | Cappola ............... A61B 90/90 |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0103819 A1 | 5/2005 | Racenet et al. |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0242610 A1 | 10/2009 | Shelton, IV et al. |
| 2009/0255974 A1 | 10/2009 | Viola |
| 2009/0272787 A1 | 11/2009 | Scirica |
| 2009/0277949 A1 | 11/2009 | Viola et al. |
| 2009/0283568 A1 | 11/2009 | Racenet et al. |
| 2009/0308907 A1 | 12/2009 | Nalagatla et al. |
| 2010/0012703 A1 | 1/2010 | Calabrese et al. |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |

(56) References Cited

U.S. PATENT DOCUMENTS

| | | |
|---|---|---|
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2010/0305552 A1 | 12/2010 | Shelton, IV et al. |
| 2011/0006099 A1 | 1/2011 | Hall et al. |
| 2011/0006101 A1 | 1/2011 | Hall et al. |
| 2011/0017801 A1 | 1/2011 | Zemlok et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0068148 A1 | 3/2011 | Hall et al. |
| 2011/0087276 A1 | 4/2011 | Bedi et al. |
| 2011/0101069 A1 | 5/2011 | Bombard et al. |
| 2011/0108603 A1 | 5/2011 | Racenet et al. |
| 2011/0114702 A1 | 5/2011 | Farascioni |
| 2011/0121049 A1 | 5/2011 | Malinouskas et al. |
| 2011/0132961 A1 | 6/2011 | Whitman et al. |
| 2011/0132964 A1 | 6/2011 | Weisenburgh, II et al. |
| 2011/0139851 A1 | 6/2011 | McCuen |
| 2011/0147433 A1 | 6/2011 | Shelton, IV et al. |
| 2011/0155781 A1 | 6/2011 | Swensgard et al. |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0238084 A1 | 9/2011 | Choi et al. |
| 2011/0278343 A1 | 11/2011 | Knodel et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2012/0016362 A1 | 1/2012 | Heinrich et al. |
| 2012/0037683 A1 | 2/2012 | Lee |
| 2012/0053406 A1 | 3/2012 | Conlon et al. |
| 2012/0061446 A1 | 3/2012 | Knodel et al. |
| 2012/0061450 A1 | 3/2012 | Kostrzewski |
| 2012/0074196 A1 | 3/2012 | Shelton, IV et al. |
| 2012/0074200 A1 | 3/2012 | Schmid et al. |
| 2012/0080474 A1 | 4/2012 | Farascioni |
| 2012/0080475 A1 | 4/2012 | Smith et al. |
| 2012/0080478 A1 | 4/2012 | Morgan et al. |
| 2012/0080479 A1 | 4/2012 | Shelton, IV |
| 2012/0080481 A1 | 4/2012 | Widenhouse et al. |
| 2012/0080482 A1 | 4/2012 | Schall et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080494 A1 | 4/2012 | Thompson et al. |
| 2012/0080495 A1 | 4/2012 | Holcomb et al. |
| 2012/0080498 A1 | 4/2012 | Shelton, IV et al. |
| 2012/0080499 A1 | 4/2012 | Schall et al. |
| 2012/0080502 A1 | 4/2012 | Morgan et al. |
| 2012/0091183 A1 | 4/2012 | Manoux et al. |
| 2012/0100200 A1 | 4/2012 | Belcheva et al. |
| 2012/0138659 A1 | 6/2012 | Marczyk et al. |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0223123 A1 | 9/2012 | Baxter, III et al. |
| 2012/0228358 A1 | 9/2012 | Zemlok et al. |
| 2012/0234893 A1 | 9/2012 | Schuckmann et al. |
| 2012/0234895 A1 | 9/2012 | O'Connor et al. |
| 2012/0234897 A1 | 9/2012 | Shelton, IV et al. |
| 2012/0234899 A1 | 9/2012 | Scheib et al. |
| 2012/0239009 A1 | 9/2012 | Mollere et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241504 A1 | 9/2012 | Soltz et al. |
| 2012/0241505 A1 | 9/2012 | Alexander, III et al. |
| 2012/0248169 A1 | 10/2012 | Widenhouse et al. |
| 2012/0248170 A1 | 10/2012 | Marczyk |
| 2012/0253329 A1 | 10/2012 | Zemlok et al. |
| 2012/0255986 A1 | 10/2012 | Petty et al. |
| 2012/0286021 A1 | 11/2012 | Kostrzewski |
| 2012/0286022 A1 | 11/2012 | Olson et al. |
| 2012/0292369 A1 | 11/2012 | Munro, III et al. |
| 2012/0298719 A1 | 11/2012 | Shelton, IV et al. |
| 2012/0298722 A1 | 11/2012 | Hess et al. |
| 2012/0312858 A1 | 12/2012 | Patankar et al. |
| 2012/0312859 A1 | 12/2012 | Gupta et al. |
| 2012/0312860 A1 | 12/2012 | Ming et al. |
| 2012/0312861 A1 | 12/2012 | Gurumurthy et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037594 A1 | 2/2013 | Dhakad et al. |
| 2013/0037595 A1 | 2/2013 | Gupta et al. |
| 2013/0037596 A1 | 2/2013 | Bear et al. |
| 2013/0037597 A1 | 2/2013 | Katre et al. |
| 2013/0037598 A1 | 2/2013 | Marczyk |
| 2013/0041406 A1 | 2/2013 | Bear et al. |
| 2013/0048697 A1 | 2/2013 | Shelton, IV et al. |
| 2013/0056518 A1 | 3/2013 | Swensgard |
| 2013/0056521 A1 | 3/2013 | Swensgard |
| 2013/0062391 A1 | 3/2013 | Boudreaux et al. |
| 2013/0062393 A1 | 3/2013 | Bruewer et al. |
| 2013/0062394 A1 | 3/2013 | Smith et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0068821 A1 | 3/2013 | Huitema et al. |
| 2013/0075443 A1 | 3/2013 | Giordano et al. |
| 2013/0075444 A1 | 3/2013 | Cappola et al. |
| 2013/0075445 A1 | 3/2013 | Balek et al. |
| 2013/0075446 A1 | 3/2013 | Wang et al. |
| 2013/0075447 A1 | 3/2013 | Weisenburgh, II et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0075451 A1 | 3/2013 | Balek et al. |
| 2013/0082086 A1 | 4/2013 | Hueil et al. |
| 2013/0087597 A1 | 4/2013 | Shelton, IV et al. |
| 2013/0087599 A1 | 4/2013 | Krumanaker et al. |
| 2013/0087600 A1 | 4/2013 | Scirica |
| 2013/0087601 A1 | 4/2013 | Farascioni |
| 2013/0087602 A1 | 4/2013 | Olson et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098966 A1 | 4/2013 | Kostrzewski et al. |
| 2013/0098970 A1 | 4/2013 | Racenet et al. |

(56) References Cited

U.S. PATENT DOCUMENTS

| | | |
|---|---|---|
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | (Tarinelli) Racenet et al. |
| 2013/0112730 A1 | 5/2013 | Whitman et al. |
| 2013/0112732 A1 | 5/2013 | Aranyi et al. |
| 2013/0112733 A1 | 5/2013 | Aranyi et al. |
| 2013/0119109 A1 | 5/2013 | Farascioni et al. |
| 2013/0126581 A1 | 5/2013 | Yates et al. |
| 2013/0126582 A1 | 5/2013 | Shelton, IV et al. |
| 2013/0126586 A1 | 5/2013 | Zhang et al. |
| 2013/0140343 A1 | 6/2013 | Knodel |
| 2013/0144333 A1 | 6/2013 | Viola |
| 2015/0272576 A1 | 10/2015 | Cappola |
| 2016/0249921 A1 | 9/2016 | Cappola |
| 2019/0015099 A1* | 1/2019 | Cappola ............... A61B 90/98 |

FOREIGN PATENT DOCUMENTS

| | | |
|---|---|---|
| CN | 103298425 A | 9/2013 |
| CN | 108289666 A | 7/2018 |
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 1952769 A2 | 8/2008 |
| EP | 2090253 A2 | 8/2009 |
| EP | 2090254 A1 | 8/2009 |
| EP | 2583630 A2 | 4/2013 |
| EP | 2586382 A2 | 5/2013 |
| FR | 391239 A | 10/1908 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51149985 | 12/1976 |
| JP | 08033639 | 2/1996 |
| JP | 2001087272 | 4/2001 |
| JP | 2011526157 A | 10/2011 |
| JP | 2013543393 A | 12/2013 |
| JP | 2014176649 A | 9/2014 |
| JP | 2017531970 A | 10/2017 |
| SU | 659146 A1 | 4/1979 |
| SU | 728848 A1 | 4/1980 |
| SU | 980703 A1 | 12/1982 |
| SU | 990220 A1 | 1/1983 |
| WO | 2008302247 | 7/1983 |
| WO | 8910094 A1 | 11/1989 |
| WO | 9210976 A1 | 7/1992 |
| WO | 9308754 A1 | 5/1993 |
| WO | 9314706 A1 | 8/1993 |
| WO | 2004/032760 A2 | 4/2004 |
| WO | 2009071070 A2 | 6/2009 |
| WO | 2010090937 A2 | 8/2010 |
| WO | 2016036656 A1 | 3/2016 |

OTHER PUBLICATIONS

European Search Report dated Jul. 8, 2016, issued in EP Application No. 16157292.

Australian Office Action dated Aug. 26, 2019, issued in AU Appln. No. 2016200164.

Chinese Office Action dated Sep. 8, 2019, issued in CN Appln. No. 201610109472.

Japanese Office Action dated Jan. 9, 2020, issued in JP Appln. No. 2016-025883, 6 pages.

Australian Examination Report dated Oct. 3, 2020, corresponding to counterpart Australian Application No. 202020202295; 5 pages.

* cited by examiner

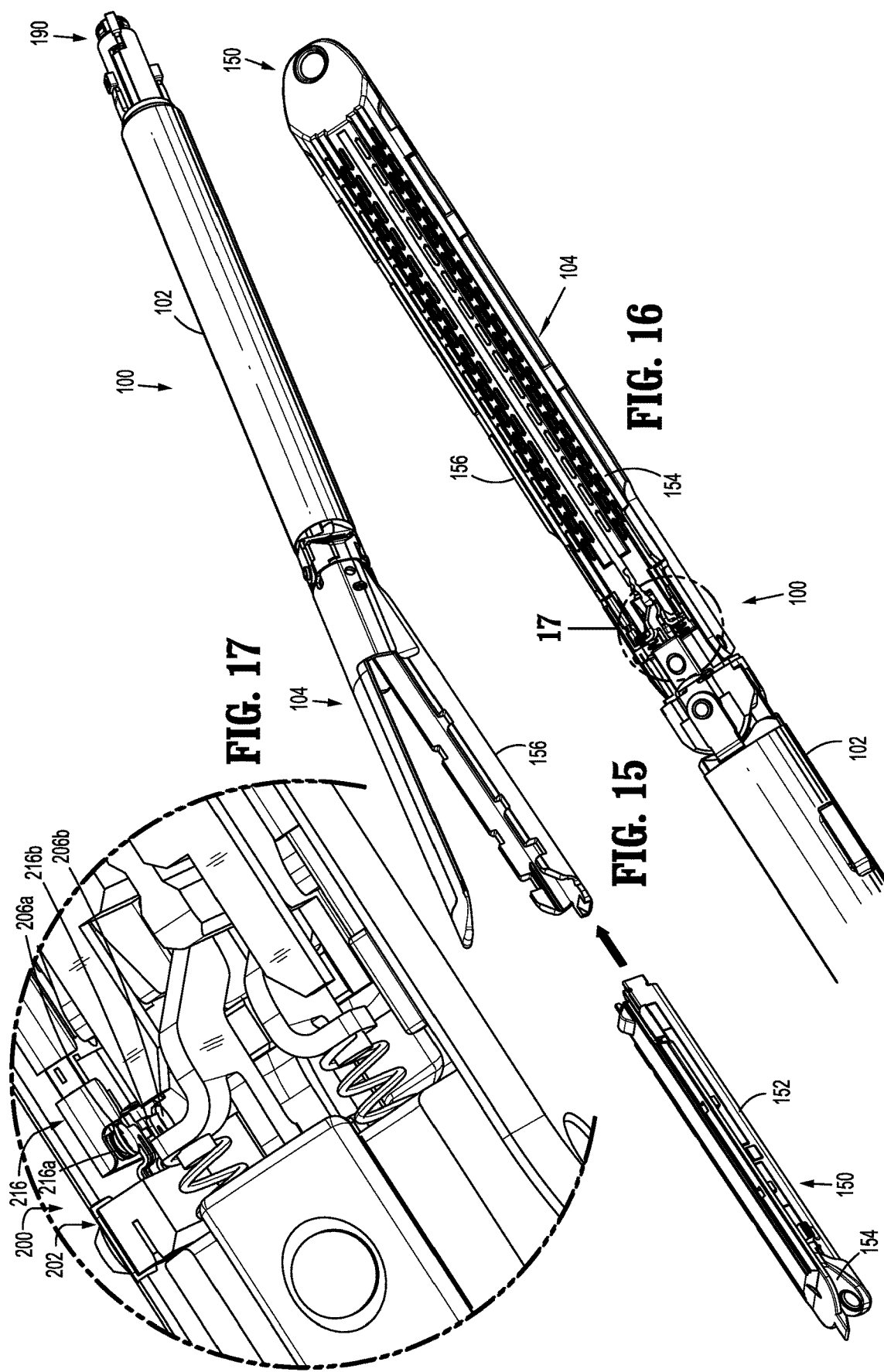

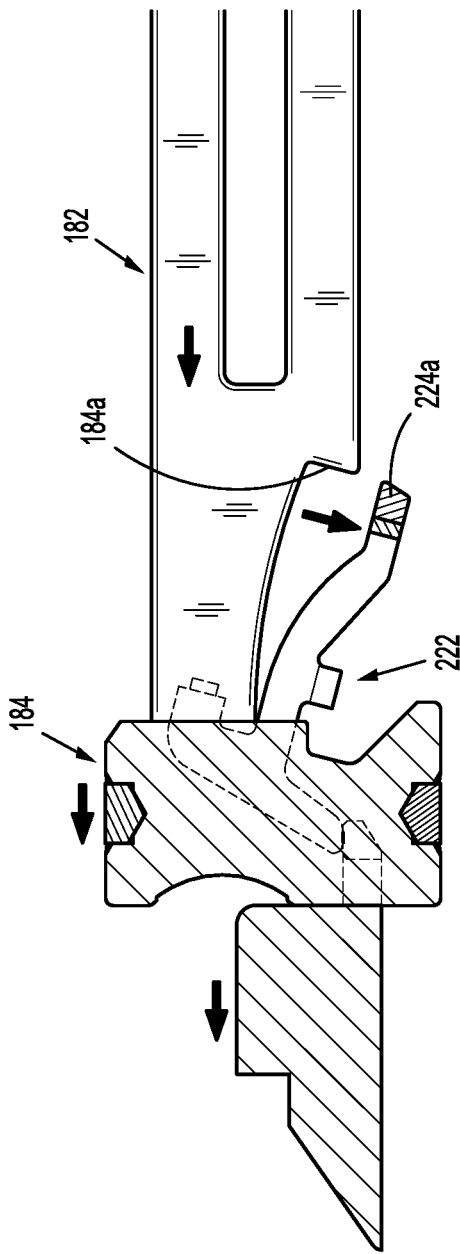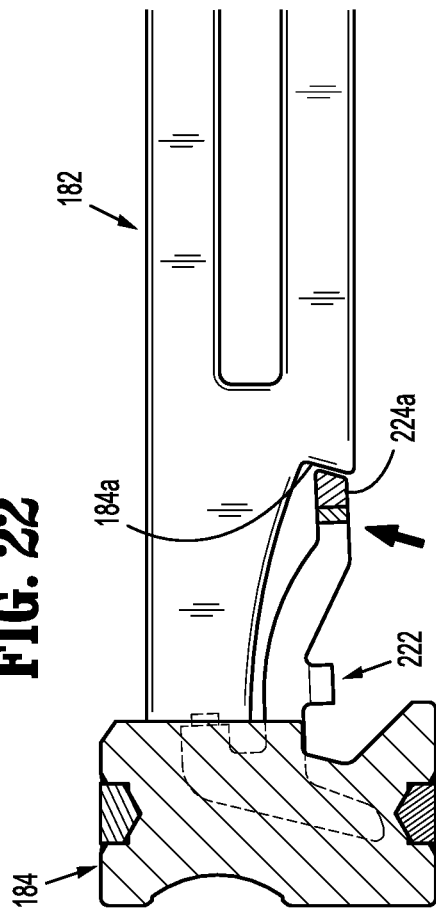

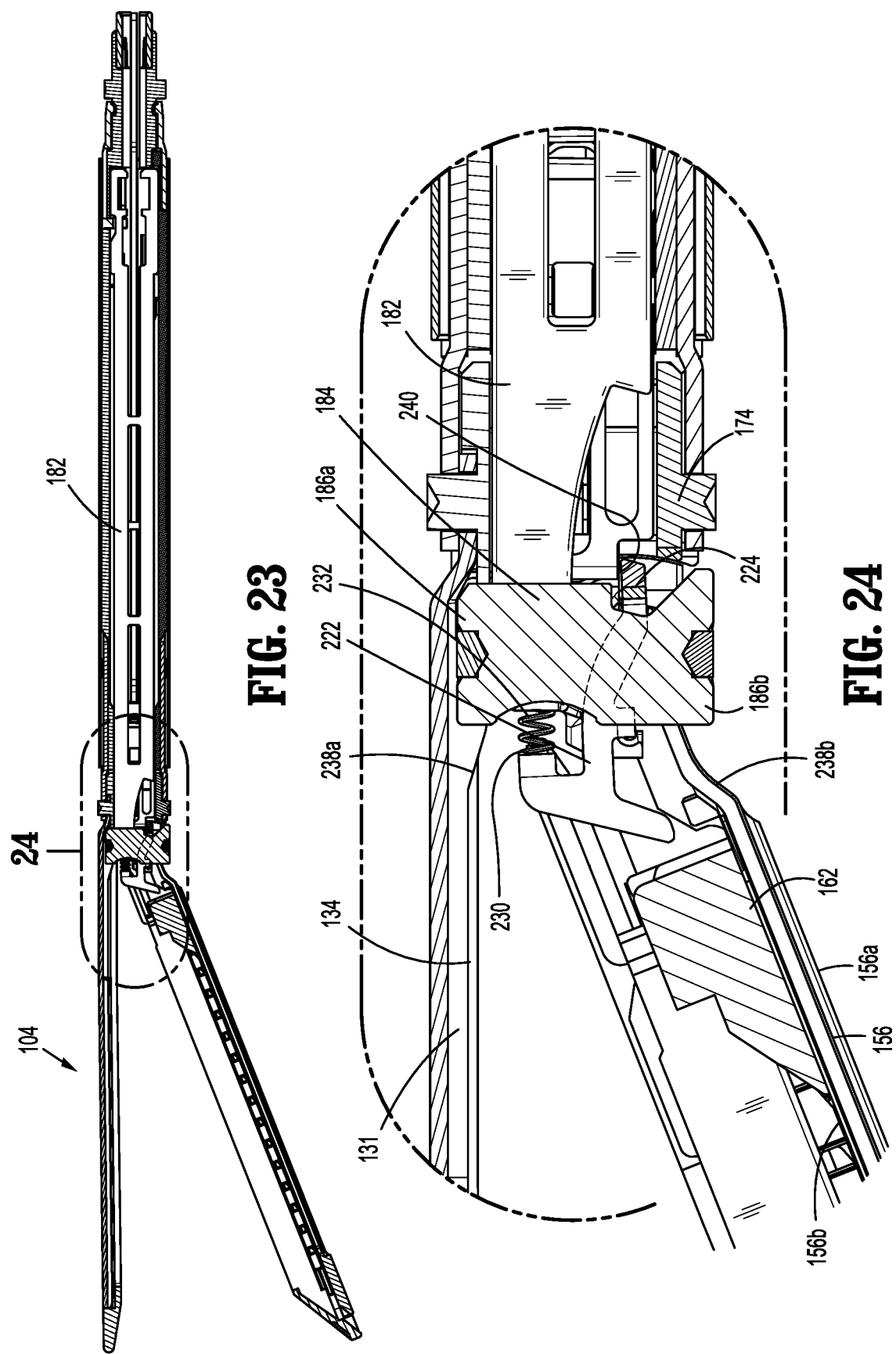

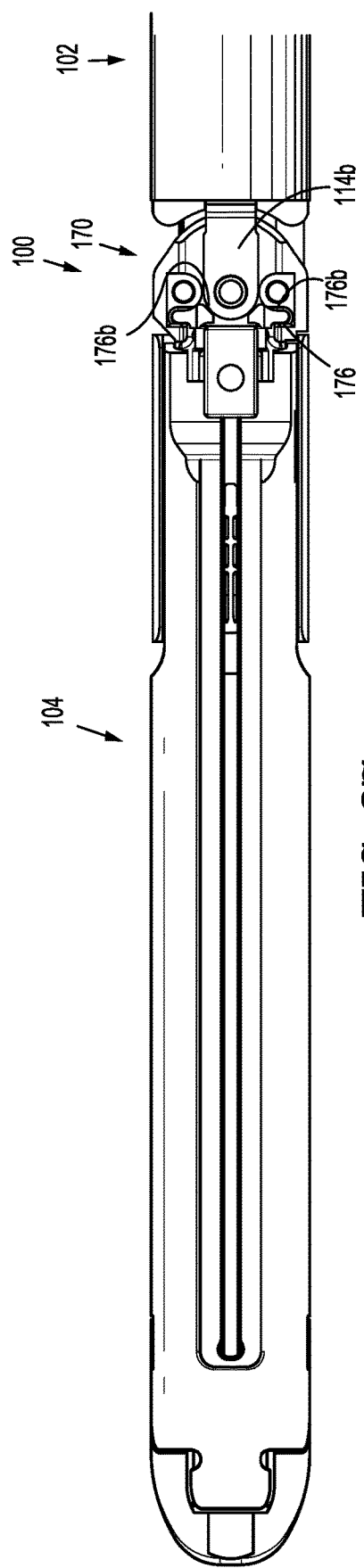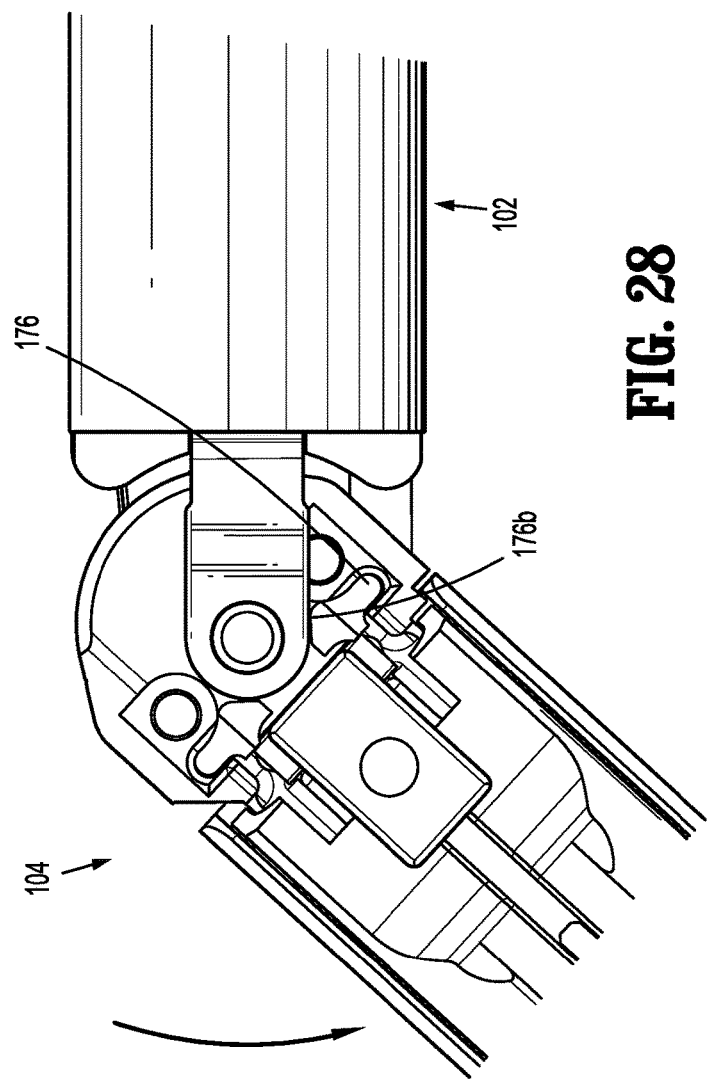

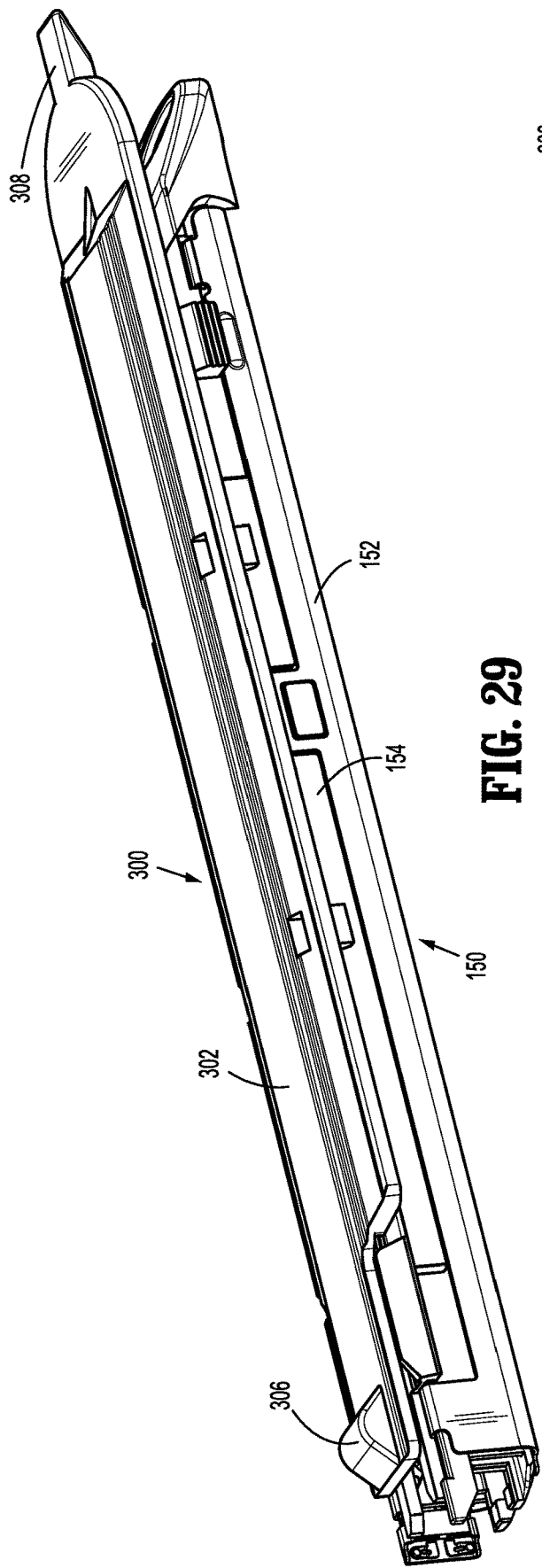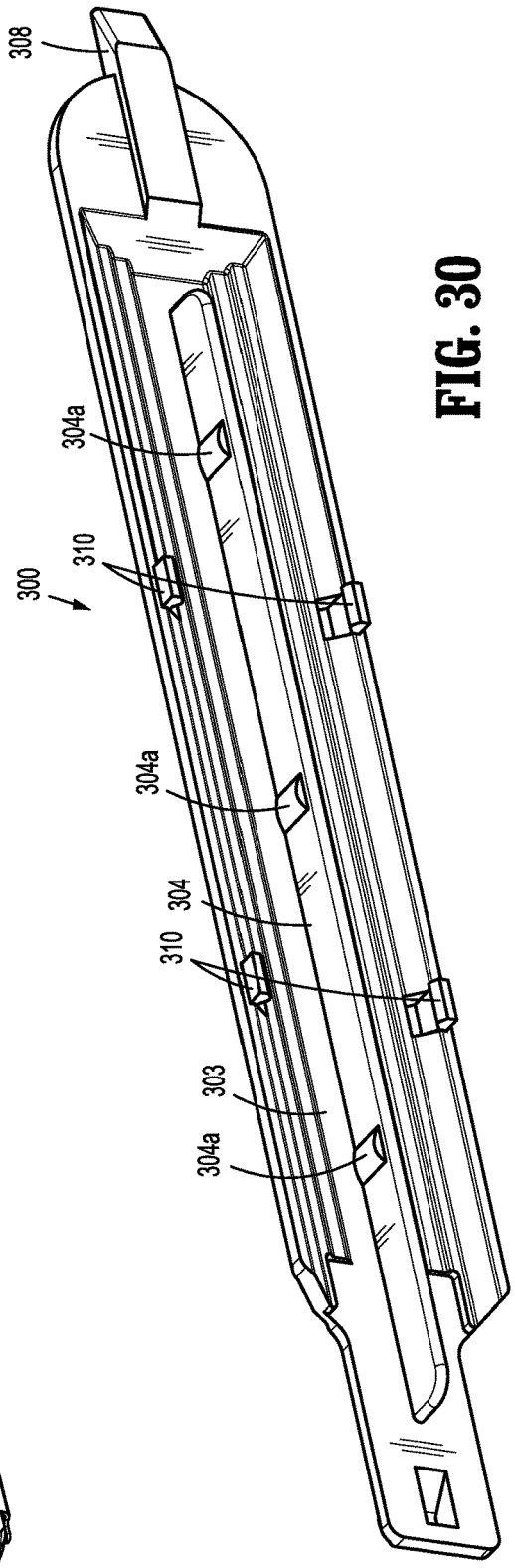

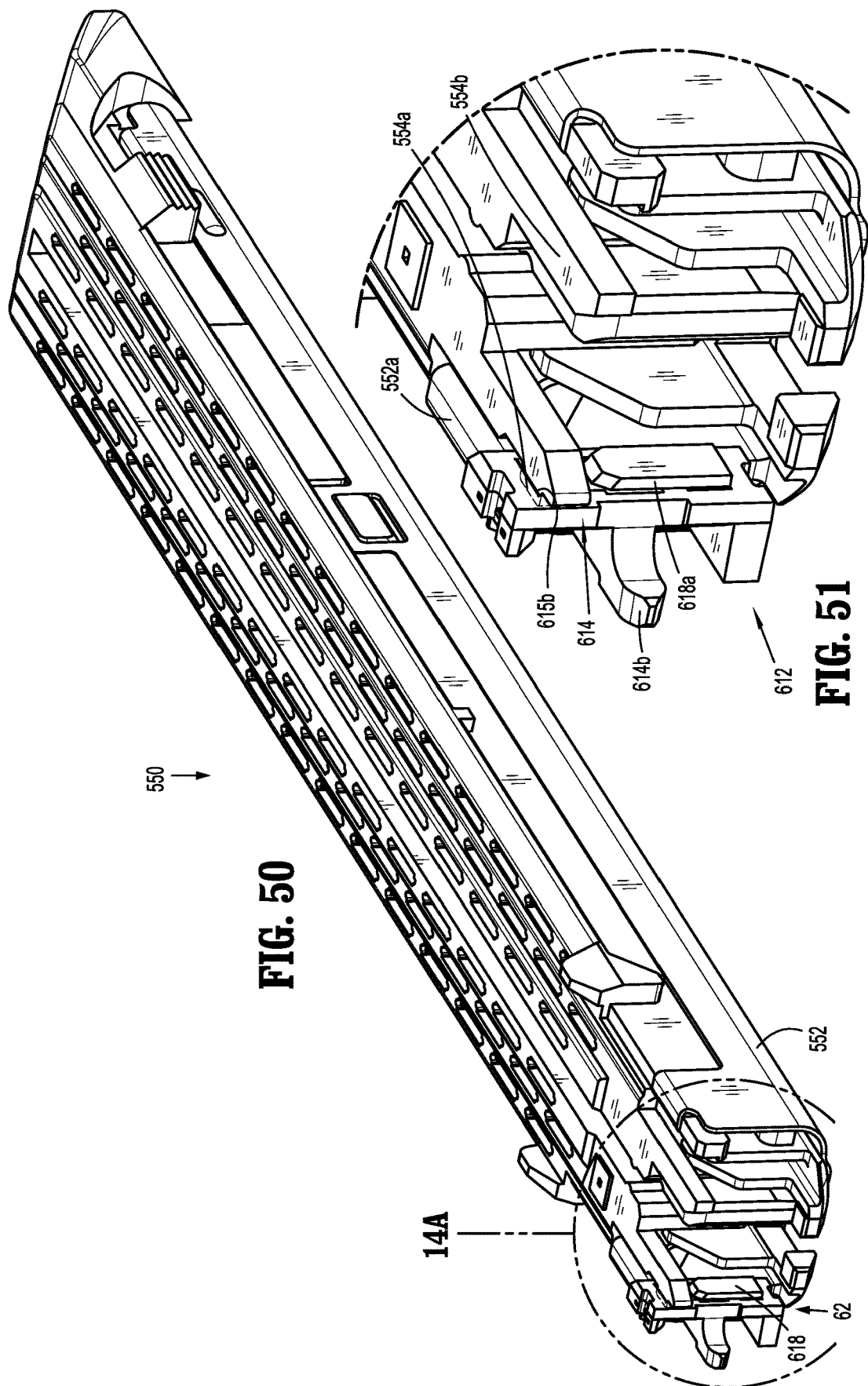

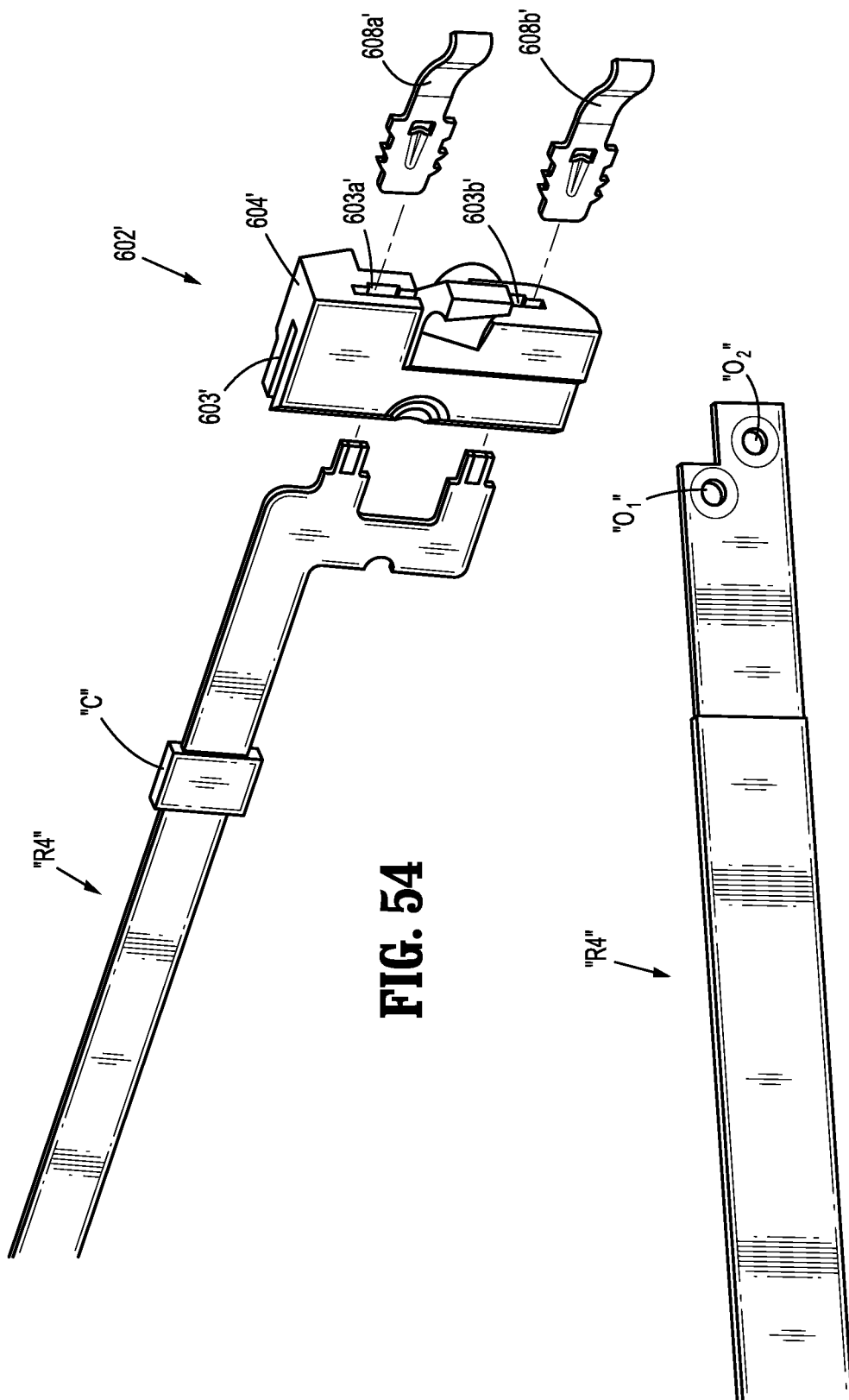

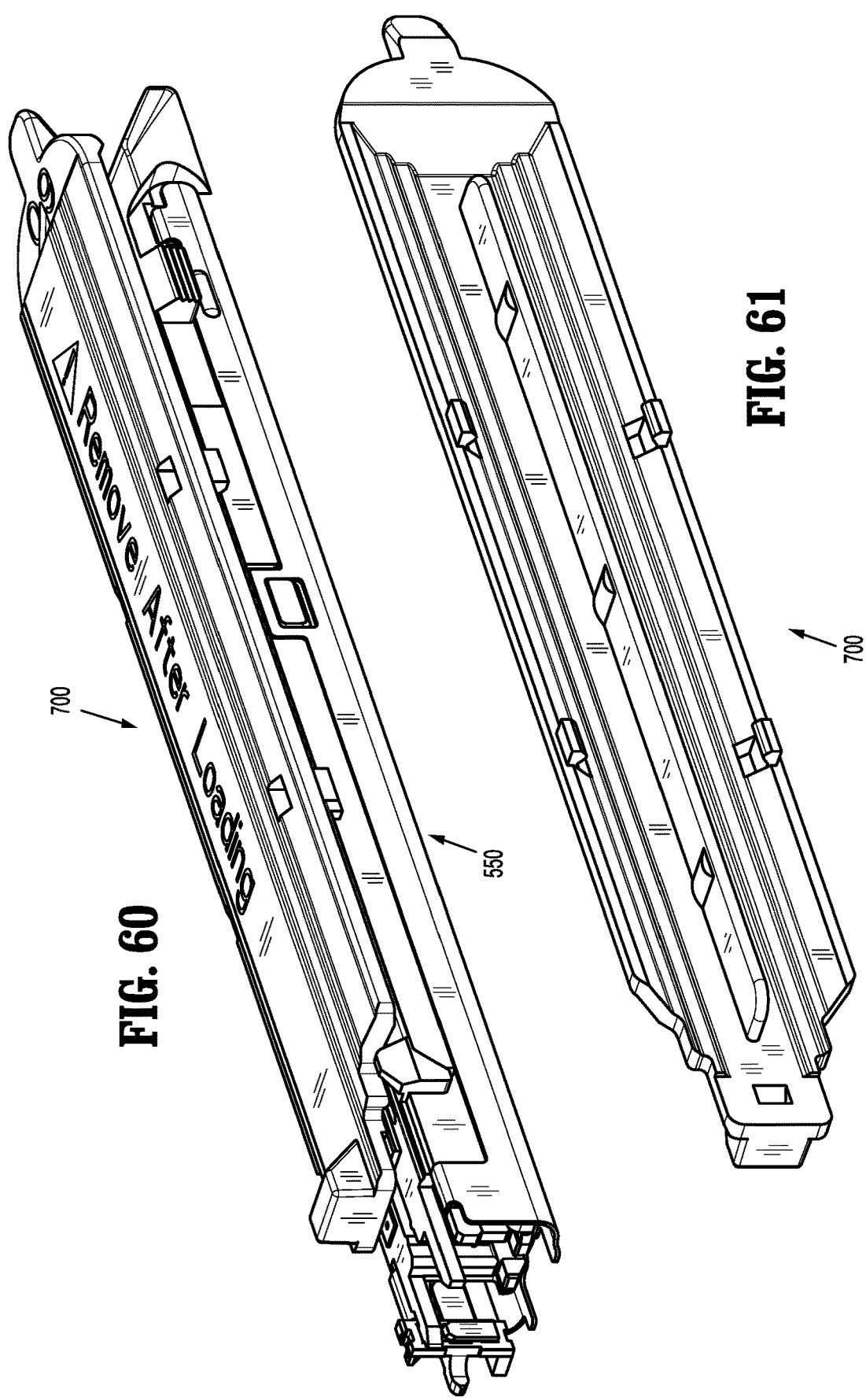

SURGICAL APPARATUS

CROSS-REFERENCE TO RELATED APPLICATION

This is a continuation of U.S. patent application Ser. No. 14/811,938, filed Jul. 29, 2015, which claims the benefit of and priority to U.S. Provisional Patent Application Ser. No. 62/121,049, filed on Feb. 26, 2015, the content of which are incorporated by reference herein in its entirety.

BACKGROUND

Technical Field

The present disclosure relates to surgical apparatus having an articulating tool assembly. More particularly, the present disclosure relates to a surgical apparatus including an improved cartridge and tool assemblies.

Background of Related Art

Surgical apparatus for operating on tissue are well known in the art and typically include a powered handle assembly, a body portion extending distally from the handle assembly, and a tool assembly supported on the distal end of the body portion and being articulable relative to the body portion. The tool assembly includes first and second jaws which are movable in relation to each other between unapproximated and approximated positions. In surgical stapling apparatus, the first jaw supports an anvil assembly and the second jaw supports a cartridge assembly. The cartridge assembly may be replaceable to permit reuse of the tool assembly during a surgical procedure. The replaceable cartridge assembly may be provided in a variety of configurations for use on tissue having different properties, i.e., thickness, density. For example, the different cartridge assemblies may have staples of different sizes and/or the staples may be arranged in different configurations.

Many cartridge assemblies include an identification chip that is electrically coupled to the handle assembly by a conductor extending through the body portion of the surgical stapling apparatus to ensure the handle assembly is programmed to operate with the attached cartridge assembly. During attachment of the cartridge assembly to the surgical stapling apparatus improper loading of the cartridge assembly may result into damage to the electrical connection between the cartridge assembly and the surgical stapling apparatus. To prevent damage to the electrical connections during loading of the cartridge assembly and during use of the surgical stapling apparatus, it would be beneficial to provide a cartridge assembly with an improved electrical connection.

SUMMARY

Accordingly, a surgical apparatus including an electrical conductor with a strain relief is provided. The surgical apparatus includes a body portion having a proximal end and a distal end and includes a connection assembly supported on the proximal end. The surgical apparatus further includes a tool assembly supported on a distal end of the body portion and being articulable relative to the body portion, the tool assembly including an identification assembly. In addition, the surgical apparatus includes an electrical conductor extending from the connection assembly to the identification assembly. The electrical conductor includes a strain relief portion for accommodating the articulation of the tool assembly relative to the body portion.

In embodiments, the strain relief portion includes a plurality of coils. A height of the plurality of coils may decrease from a proximal portion of the plurality of coils to a distal portion of the plurality of coils. Alternatively, the height of the plurality of coils is uniform from a proximal portion of the plurality of coils to a distal portion. The plurality of coils may be equally spaced relative to each other.

In some embodiments, the body portion defines a channel for receiving the electrical conductor. The channel may include a central portion for receiving the strain relief portion of the electrical conductor. The surgical apparatus may include a powered handle assembly and the electrical conductor electrically couples the identification assembly to the handle assembly. The tool assembly may include a stapling assembly. The stapling assembly may include a removable cartridge assembly. The electrical conductor may include a flexible cable. The flexible cable may include a proximal portion and a distal portion. The proximal portion of the flexible cable may be axially affixed to the body portion, for example, using adhesive.

In embodiments, the strain relief portion is configured to permit lengthening of the electrical conductor. Alternatively, or in addition, the strain relief portion is configured to permit shortening of the electrical conductor. The body portion, the tool assembly, and the electrical conductor may form a loading unit which is configured to be releasably coupled to a powered handle assembly.

The loading unit may include a jaw member and a cartridge assembly selectively receivable within the jaw member. The identification assembly may include a connector assembly disposed within the jaw member and a chip assembly disposed within the cartridge assembly. Loading of the cartridge assembly within the jaw member may cause engagement of the chip assembly with the connector assembly. The electrical conductor may include a connector member integrally formed on a proximal end thereof. The electrical conductor may include a stiffened portion attached to the electrical conductor.

In a further aspect, a surgical stapling apparatus comprises a tool assembly having a chip assembly, a staple cartridge body, a support plate, and a jaw member, the chip assembly having a first projection facilitating alignment with and connection with a connector assembly of the jaw member, the chip assembly having a second projection received in a recess in the staple cartridge body, and the connector assembly and chip assembly having an electrical connection therebetween.

The staple cartridge body, support plate, and chip assembly may form a removable and replaceable unit. The apparatus can be a loading unit having a body portion including a connection assembly supported on a proximal end thereof. The connection assembly can form an electrical connection with an adapter assembly.

The jaw can include a rail extending laterally. The chip assembly can have a third projection that interfaces with the rail to prevent vertical movement of the chip assembly, the staple cartridge body, or both. A portion of the staple cartridge body can extend proximally and can be configured to be disposed underneath the rail.

The second projection can define a notch for receiving a tab on the support plate. The staple cartridge body has at least one tab extending from the side of the staple cartridge body. The staple cartridge body at least one tab can have a length; the length of the at least one tab can be indicative of a length of a staple line defined by the staple cartridge body.

In a further aspect, a removable and replaceable staple cartridge assembly has a shipping wedge overlying a tissue contacting surface of the staple cartridge assembly, the shipping wedge includes a cartridge release projection. The staple cartridge body can define a recess that would be disposed adjacent a distal end of the stapler jaw when the shipping wedge is attached to the staple cartridge assembly. Insertion of the projection into the recess can be used to release the staple cartridge body from the stapler jaw.

The shipping wedge may have a raised portion on a proximal end thereof to prevent approximation of a stapler anvil with the staple cartridge assembly, after the staple cartridge assembly has been inserted into the stapler.

BRIEF DESCRIPTION OF THE DRAWINGS

Various embodiments of the present disclosure are described herein with reference to the drawings, wherein:

FIG. 15 is a side, perspective view of the cartridge assembly shown in FIG. 14 being loaded into the loading unit shown in FIG. 2;

FIG. 16 is a top perspective view of the loading unit shown in FIG. 2 with an anvil assembly removed;

FIG. 17 is an enlarged view of the indicated area of detail shown in FIG. 16;

FIG. 21 is a side, cross-sectional view of the distal end of the drive assembly shown in FIG. 20 and the latch member shown in FIG. 19 in a first or unlocked configuration;

FIG. 22 is a cross-sectional side view of the distal end of the drive assembly and the latch member shown in FIG. 21 in a second or locked configuration;

FIG. 23 is a cross-sectional side view taken along line 23-23 shown in FIG. 2;

FIG. 24 is an enlarged view of the indicated area of detail shown in FIG. 23;

FIG. 27 is a top view of a tool assembly of the loading unit shown in FIG. 2 with the anvil plate removed;

FIG. 28 is an enlarged view of a proximal end of the tool assembly shown in FIG. 27 in a first articulated position;

FIG. 29 is a side, perspective view of a cartridge assembly of the loading unit shown in FIG. 2 and a shipping wedge according to an embodiment of the present disclosure;

FIG. 30 is a bottom, perspective view of the shipping wedge shown in FIG. 29;

FIG. 50 is a perspective end view of a cartridge assembly of the loading unit shown in FIG. 33 including the chip assembly shown in FIG. 47;

FIG. 51 is an enlarged view of the indicated area of detail shown in FIG. 50;

FIG. 53 is a perspective view of a proximal end of a flexible cable according to an alternative embodiment of the present disclosure;

FIG. 54 is a perspective view of a distal end of the flexible cable shown in FIG. 53;

FIG. 60 is a side, perspective view of a cartridge assembly of the loading unit shown in FIG. 33 and a shipping wedge according to another embodiment of the present disclosure;

FIG. 61 is a bottom, perspective view of the shipping wedge shown in FIG. 29.

DETAILED DESCRIPTION OF THE DRAWINGS

Figure 1:
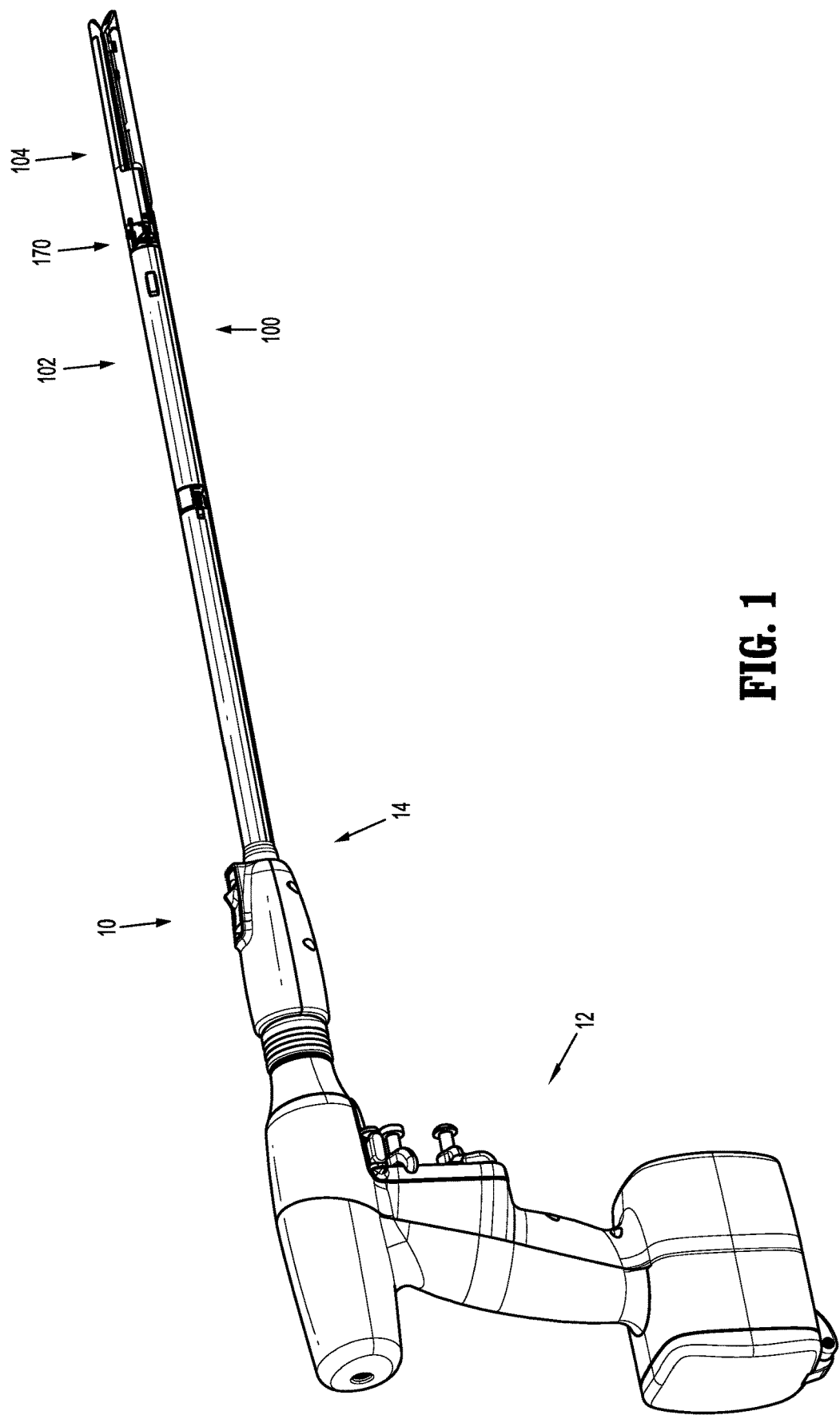
FIG. 1 is a side, perspective view of an embodiment of the presently disclosed surgical stapling apparatus including a tool assembly in an approximated position.

Embodiments of the presently disclosed surgical apparatus will now be described in detail with reference to the drawings wherein like reference numerals designate identical or corresponding elements in each of the several views. In this description, the term "proximal" is generally used to refer to the portion of the apparatus that is closer to a clinician, while the term "distal" is generally used to refer to the portion of the apparatus that is farther from the clinician.

As a tool assembly of a surgical apparatus is articulated, any cables extending from the body portion to the tool assembly experience strain, i.e., compression or tension. During articulation of the tool assembly, the strain experienced by the cable or cables may damage the cables or cause the cables to become detached. The embodiments of the present disclosure address providing a strain relief for relieving the strain experienced by the cable or cables during articulation of the tool assembly. The embodiments of the present disclosure further address preventing damage to the electrical connections within the tool assembly and the surgical apparatus.

FIG. 1 illustrates an embodiment of the presently disclosed surgical apparatus shown generally as surgical stapler 10. Although illustrated as a surgical stapler, the apparatus may include other types of end effectors including forceps, retractors, clip appliers or the like. The surgical stapler 10 includes a powered handle assembly 12, a body portion 14, and a loading unit 100. Handle assembly 12 and body portion 14 are configured to effect operation of loading unit 100. For a detailed description of the structure and function of handle assembly 12 and body portion 14, please refer to commonly owned U.S. Patent Application Publication No. 2012/0253329 ("the '329 publication"), the content of which is incorporated by reference herein in its entirety. Although loading unit 100 is shown and described as being selectively secured to body portion 14 of surgical stapler 10, it is envisioned that loading unit 100 can be supported directly on the distal end of the body portion 14.

Figure 2:
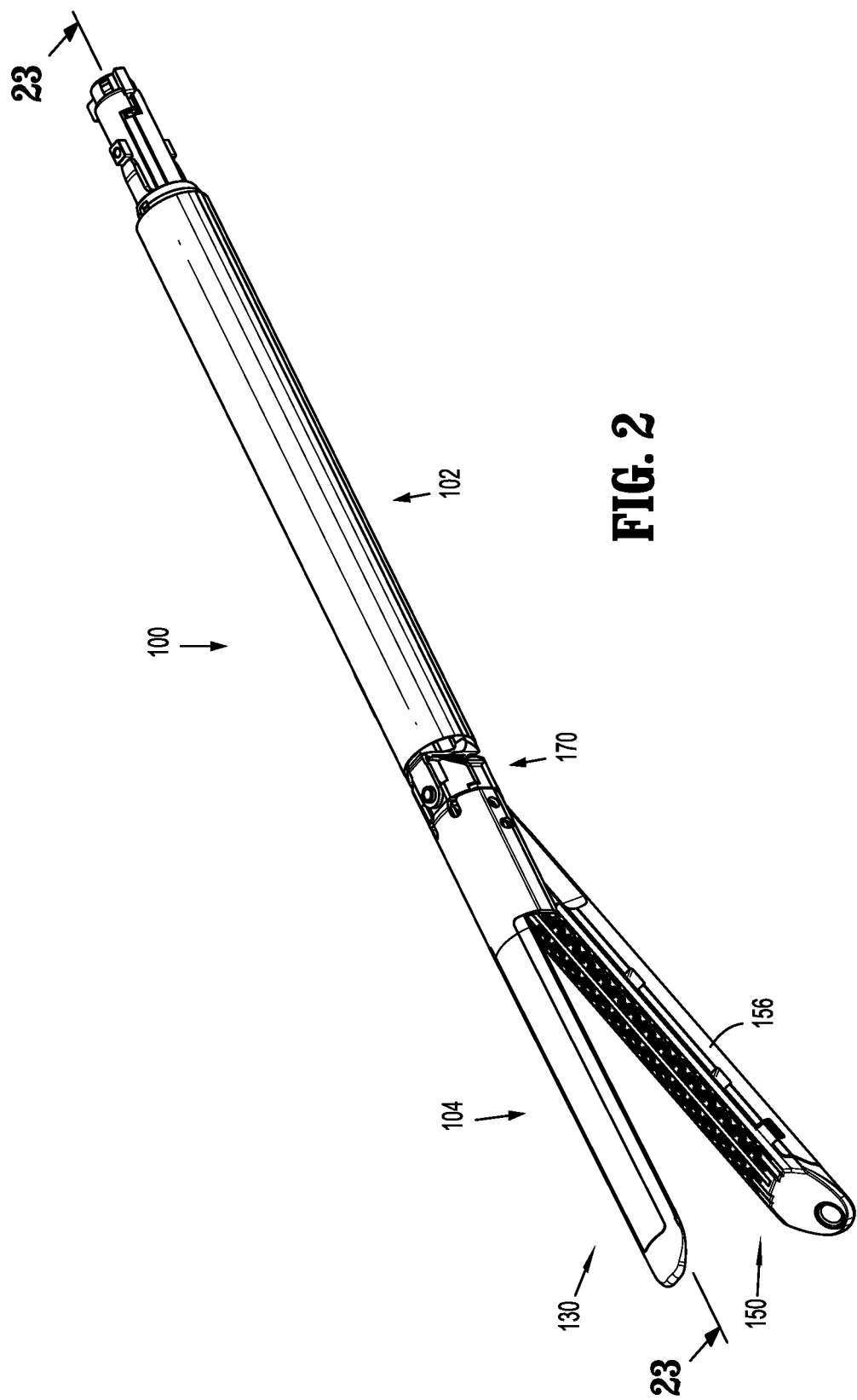
FIG. 2 is a side, perspective view of a disposable loading unit of the surgical stapling apparatus shown in FIG. 1.

Referring to FIGS. 1 and 2, the loading unit 100 includes a proximal body portion 102 and a tool assembly 104. A mounting assembly 170 is secured to the tool assembly 104 and is pivotally coupled to the proximal body portion 102 of the loading unit 100 to pivotally secure the tool assembly 104 to the proximal body portion 102. The loading unit 100 is substantially as described in U.S. Patent Application Publication No. 2013/0098965 ("the '965 publication") except that the firing lockout mechanism has been changed, and components for cooperating with a powered handle assembly, i.e., an identification assembly and a flexible cable, and a shipping wedge have been added. The '965 publication is hereby incorporated by reference herein in its entirety. Accordingly, the components of the loading unit 100 which are common to those which are disclosed in the '965 publication, will only be briefly described herein. In contrast, the components which are newly presented herein, including a connection assembly 190 (FIGS. 5-7), an identification assembly 200 (FIGS. 8-17), a firing lockout assembly 220 (FIGS. 19-28), a shipping wedge 300 (FIGS. 29 and 30), a flexible cable "R2" (FIGS. 31 and 32) and their methods of operation will be described in detail herein.

Figure 3:
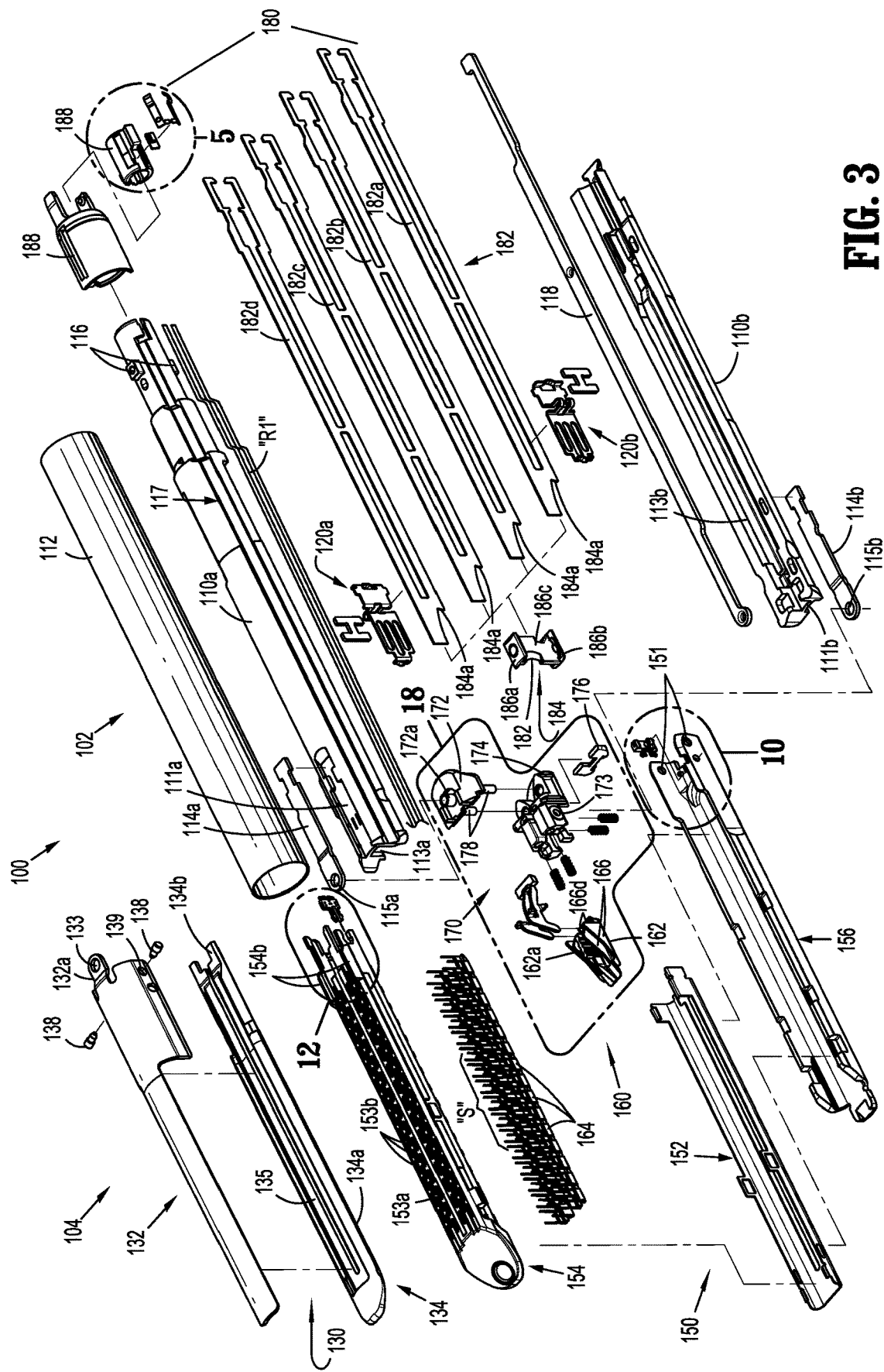
FIG. 3 is a side, perspective view of the loading unit shown in FIG. 2 with parts separated.

With reference to FIG. 3, the proximal body portion 102 of the loading unit 100 includes an upper housing half 110a and a lower housing half 110b which are contained within an outer sleeve 112. The upper housing half 110a defines a recess 111a for receiving a first end of a first coupling member 114a and the lower housing half 110b defines a recess 111b for receiving a first end of a second coupling member 114b. When the outer sleeve 112 is positioned about the upper and lower housing halves 110a, 110b, the first and second coupling members 114a and 114b are retained within the respective recesses 111a, 111b by the outer sleeve 112.

The proximal end of the upper housing half 110a includes engagement nubs 116 for releasably engaging the distal end of the body portion 14 (FIG. 1) of the stapling apparatus 10 (FIG. 1) in a bayonet-type coupling arrangement. The upper and lower housing halves 110a, 110b each define a channel 113a, 113b, respectively, for slidably receiving a drive member 182 of a drive assembly 180, as will be described in further detail below. An articulation link 118 is slidably positioned between the upper and lower housing halves 110a, 110b and is adapted to engage an articulation mechanism (not shown) of the surgical stapler 10 (FIG. 1) to facilitate articulation of the tool assembly 104 in relation to the proximal body portion 102. A pair of blow out plate assemblies 120a, 120b are positioned adjacent the distal end of the upper and lower housing halves 110a, 110b to prevent outward buckling and/or bulging of the drive member 182 during articulation and firing of the tool assembly 104.

A channel 117 extends the length of upper housing half 110a for receiving a conductor, e.g., electrical ribbon or cable "R1" or wires. As will be described in further detail below, electrical ribbon "R1" electrically couples a connection assembly 190 disposed in a proximal end of the proximal body portion 102 of the loading unit 100 with an identification assembly 200 (FIG. 8) disposed within the tool assembly 104 of the loading unit 100. A more detailed description of the components of the proximal body portion 102 is provided in commonly owned U.S. Pat. No. 7,143,924 ("the '924 patent") the content of which is hereby incorporated by reference herein in its entirety.

Still referring to FIG. 3, the tool assembly 104 includes an anvil assembly 130 and a replaceable cartridge assembly 150 which are movable in relation to each other between unapproximated and approximated positions. The anvil assembly 130 includes an anvil body 132 and an anvil plate 134 which is secured to the underside of the anvil body 132 to define a channel 131 (FIG. 24). A proximal end of the anvil body 132 includes a bracket 132a defining a hole 133 for receiving a cylindrical pivot member 172a of an upper mounting portion 172 of a mounting assembly 170. The anvil plate 134 defines a longitudinal slot 135 which is dimensioned to slidably receive a portion of the working end 184 of a drive member 182 as will be discussed in further detail below. A tissue contacting surface 134a of the anvil plate 134 defines a plurality of staple receiving depressions (not shown).

The cartridge assembly 150 includes a support plate 152, cartridge body 154, a plurality of staples "S", and a staple firing assembly 160 that includes an actuation sled 162 and is further described below. The cartridge assembly 150 is receivable in a jaw member 156. The cartridge body 154 and the support plate 152 are attached to the jaw member 156 by a snap-fit connection as described in the '965 publication which has been incorporated herein by reference. Other forms of connection are contemplated and can be used in place of the snap-fit connection or in addition thereto.

The jaw member 156 is pivotally secured to the anvil body 132 by pivot pins 138 which extend through openings 139 formed in the anvil body 132 and openings 151 formed in the jaw member 156. The cartridge body 154 defines a longitudinal slot 153a and a plurality of laterally spaced staple retention slots 153b which are positioned in alignment with the staple receiving depressions (not shown) in the tissue contacting surface 134a of the anvil plate 134. An actuation sled 162 is configured to translate through the cartridge body 154. The longitudinal slot 153a of the cartridge body 154 receives a projection 162a formed on the actuation sled 162 to guide the actuation sled 162 through the cartridge body 154. The cartridge body 154 includes a detent 154a (FIG. 14) extending within the longitudinal slot 153a which are received in the recesses 163a (FIG. 14) formed on the projection 162a of the actuation sled 162 to secure the actuation sled 162 in place during shipping of the cartridge assembly 150. Each retention slot 153b receives a fastener or staple "S" and a pusher 164. The actuation sled 162 is positioned within the cartridge body 154 to pass longitudinally through the cartridge body 154 into engagement with the pushers 164 to sequentially eject the staples "S" from the cartridge body 154. The cartridge body 154 further includes a pair of tissue stop members 154b (FIG. 14) which prevent tissue (not shown) from being positioned proximally of the staple retention slots 153b. For a more detailed discussion of the cartridge assembly 150 including the support plate 152, see the '965 publication which has been incorporated herein by reference.

Figure 4:
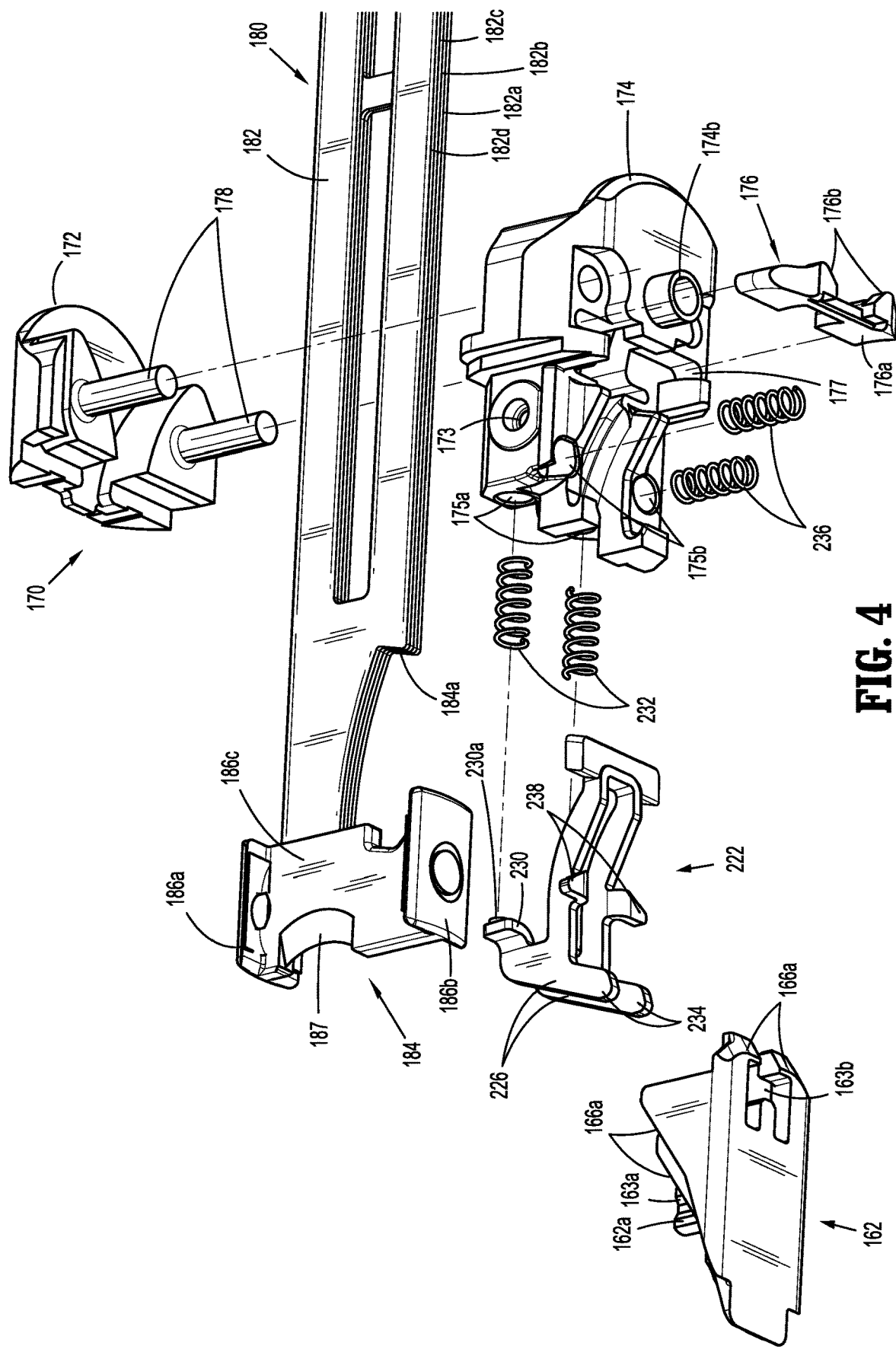
FIG. 4 is an enlarged side, perspective bottom view of a mounting assembly and a firing lockout assembly of the loading unit shown in FIG. 2 with parts separated.

Referring to FIGS. 3 and 4, the mounting assembly 170 includes the upper and lower mounting portions 172, 174 and a retention blade 176. As shown, the upper and lower mounting portions 172, 174 are secured together by the posts 178 that extend from the upper mounting portion 172. Each of the upper and lower mounting portions 172, 174 includes a pivot member 172a (FIG. 3) and 174a (FIG. 4), respectively. As described above, the pivot member 172a on the upper mounting portion 172 is received within the hole 133 (FIG. 3) of the bracket 132a of the anvil body 132 to secure the upper mounting portion 172 to the anvil body 132. The first coupling member 114a (FIG. 3) of the proximal body portion 102 has a second end which defines an opening 115a which also receives the pivot member 172a. The pivot member 174a on the lower mounting portion 174 is received in an opening 115b of the second coupling member 114b (FIG. 3) of the proximal body portion 102. The pivot pins 138 which secure the anvil body 132 to the jaw member 156 extend through the openings 139 formed in the anvil body 132 and the openings 151 formed in the jaw member 156 and are received in the openings 173 formed in the lower mounting portion 174 to secure the lower mounting portion 174 to the jaw member 156 (FIG. 3). The lower mounting portion 174 defines a slot 177 for receiving the retention blade 176. As will be described in further detail below, retention blade 176 includes a curved distal facing surface 176a (FIG. 4) and a pair of limiting members 176b (FIG. 4).

The drive assembly 180 includes the drive member 182 having a body and a working end 184. The working end 184 includes an upper flange 186a, a lower flange 186b, a vertical strut 186c interconnecting the upper flange 186a and the lower flange 186b, and a knife 187 supported on or formed into the vertical strut 186c. The upper flange 186a is positioned to be slidably received within the channel 131 (FIG. 24) of the anvil assembly 130 and the lower flange 186b is positioned to be slidably positioned along an outer surface 156a (FIG. 24) of the jaw member 156. In use, distal movement of the drive member 182 initially advances the upper flange 186a into a cam surface 134b formed on the anvil plate 134 and advances the lower flange 186b into engagement with a cam surface 156b formed on the jaw member 156 to pivot the cartridge assembly 150 towards the anvil assembly 130 to the approximated or closed position. Continued advancement of the drive member 182 progressively maintains a minimum tissue gap between the anvil assembly 130 and the cartridge assembly 150 adjacent the working end 184 of the drive assembly 180 as the working end 184 moves through the tool assembly 104.

The distal end of the body of the drive member 182 supports the working end 184 of the drive member 182 and defines a stop surface 184a. The actuation sled 162 (FIG. 3) is disposed within the cartridge assembly 150 (FIG. 3) at a position distal of the working end 184. When the working end 184 is in its proximal-most position and the tool assembly 104 is in the open or unapproximated position (FIG. 24), the sled 162 and the working end 184 are in their initial position. The sled 162 includes a plurality of cam surfaces 166a which are positioned to engage and lift the pushers 164 within the staple retention slots 153b of the cartridge body 154. The pushers 164 (FIG. 3) are positioned within the cartridge assembly 150 to eject the staples "S" from the cartridge body 154 when the sled 162 is advanced through the tool assembly 104. The proximal end of the sled 162 includes one or more fingers 166a which define an opening or slot 163 (FIG. 4) which will be described in further detail below.

In certain embodiments, the body of the drive member 182 is formed from a plurality of stacked sheets 182a-d of material, e.g., stainless steel. A locking member 188 (FIG. 3) is supported about the proximal end of the loading unit 100 to prevent axial movement of the drive member 182 until the loading unit 100 is attached to the stapling apparatus 10

(FIG. 1). A more detailed discussion of the above-identified components of the loading unit 100 is described in the '924 patent which has been incorporated herein by reference in its entirety.

Figure 5:
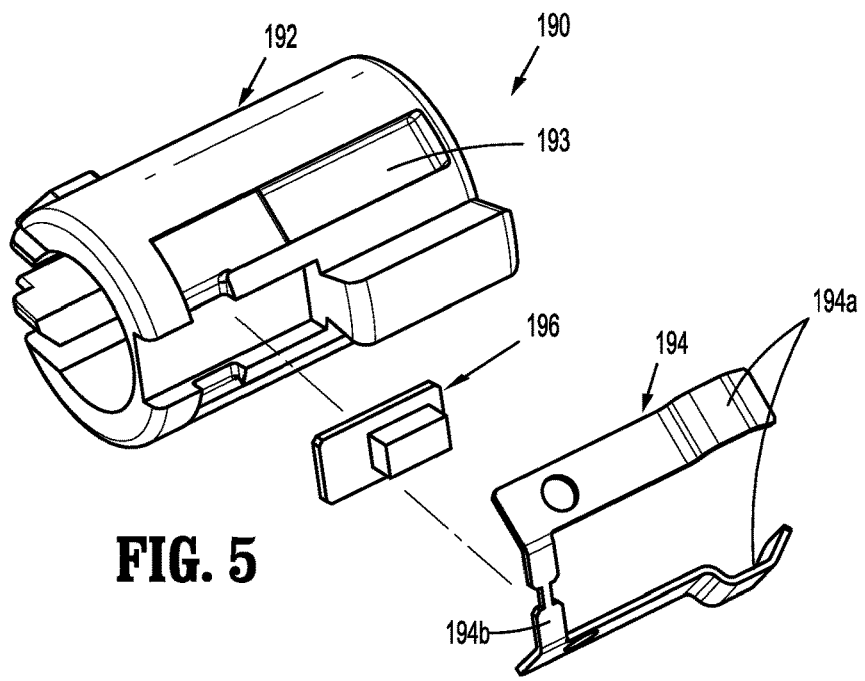
FIG. 5 is a side perspective view of the indicated area of detail shown in FIG. 2.
Figure 6:
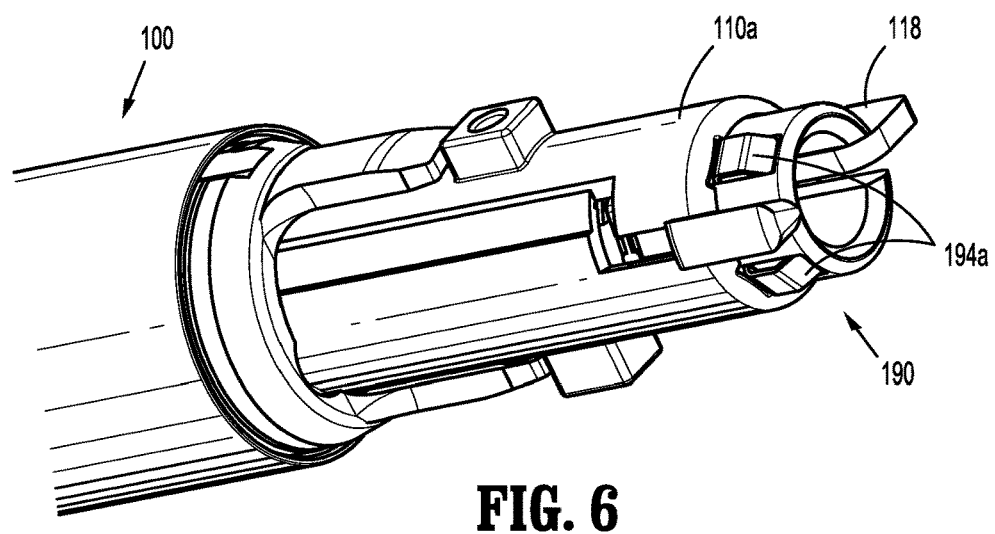
FIG. 6 is an enlarged perspective view of a proximal end of the loading unit shown in FIG. 2.
Figure 7:
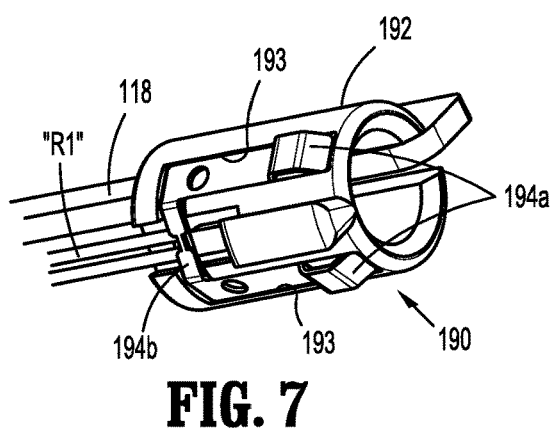
FIG. 7 is a side, perspective view of the proximal end of the loading unit shown in FIG. 2 with an upper housing half removed.
Figure 8:
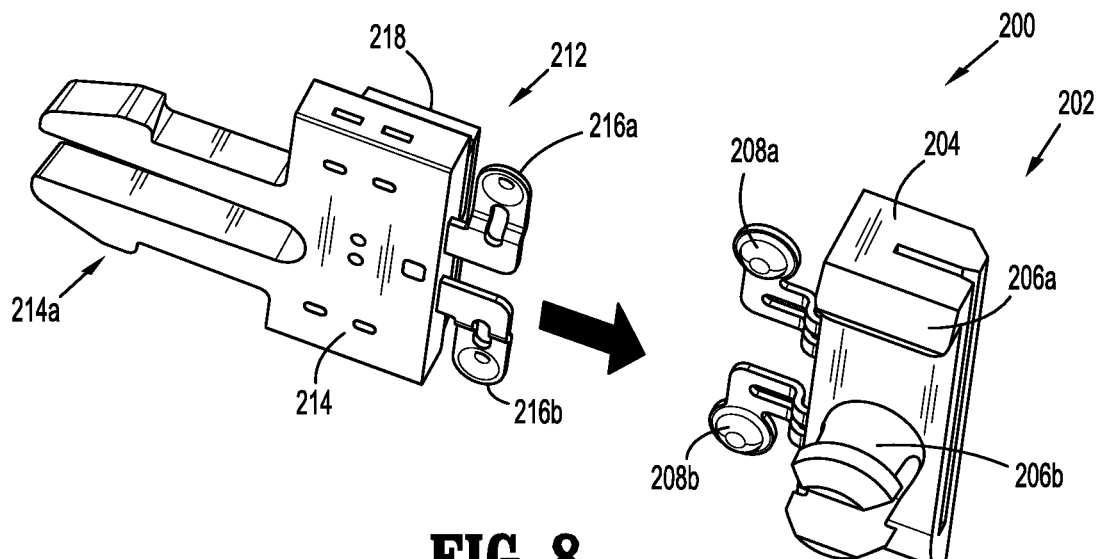
FIG. 8 is a side, perspective view of an identification assembly of the loading unit shown in FIG. 2 with parts separated.
Figure 9:
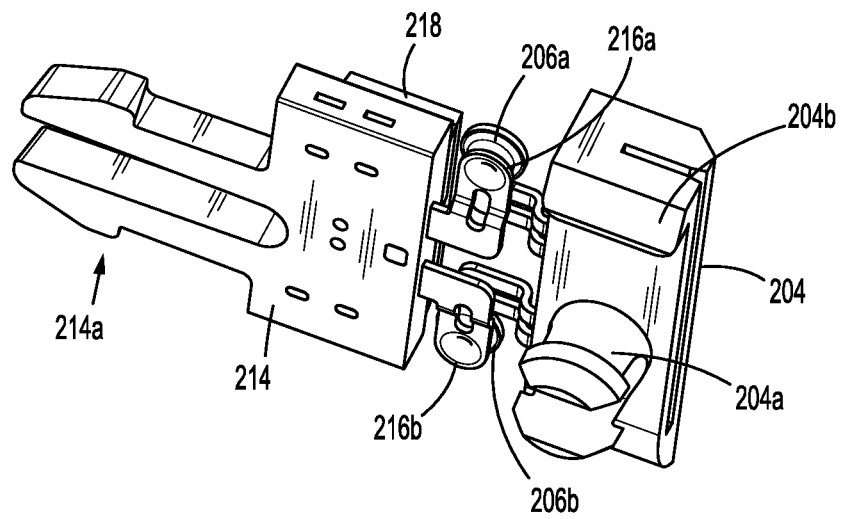
FIG. 9 is a side, perspective view of the identification assembly shown in FIG. 8.
Figure 10:
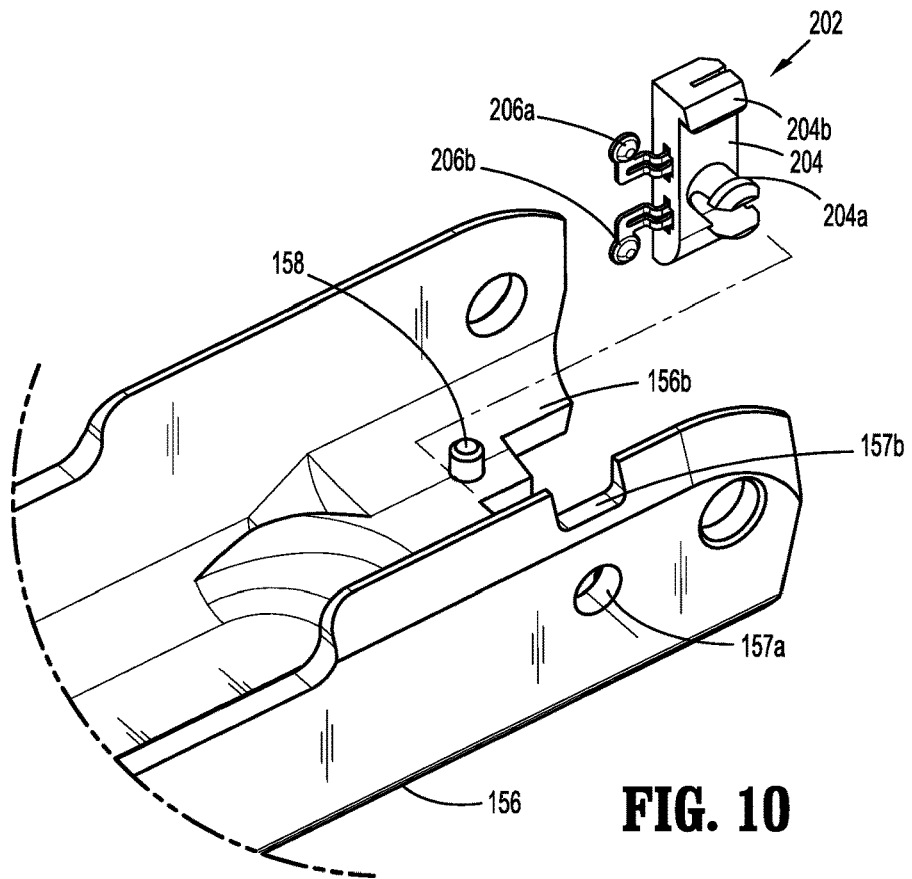
FIG. 10 is a perspective view of a connector assembly of the identification assembly shown in FIG. 8 and a proximal end of a jaw member of the loading unit shown in FIG. 2 with parts separated.
Figure 11:
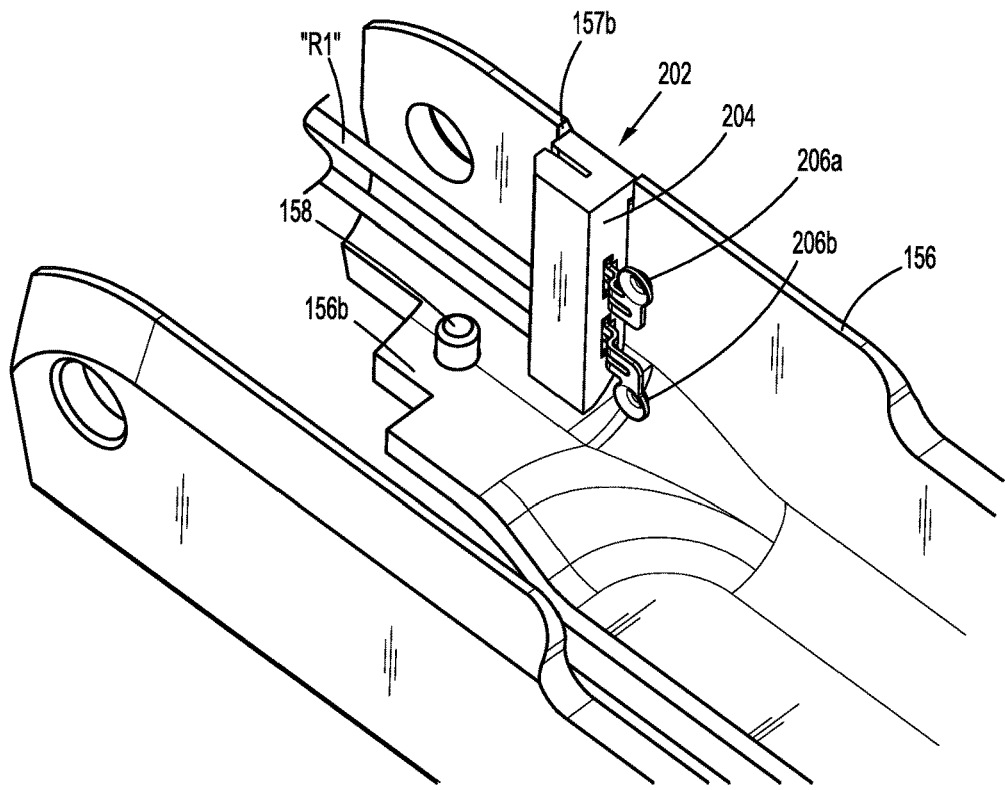
FIG. 11 is an alternative perspective view of the connector assembly and jaw member shown in FIG. 10.
Figure 12:
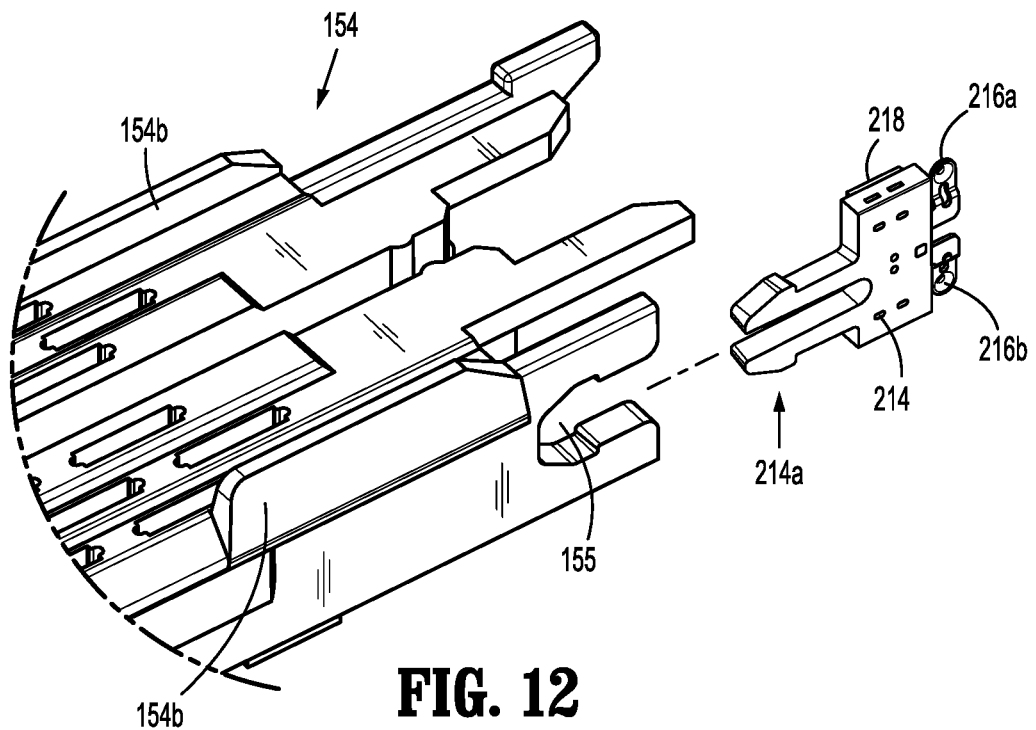
FIG. 12 is an enlarged view of the indicated area of detail shown in FIG. 3.
Figure 13:
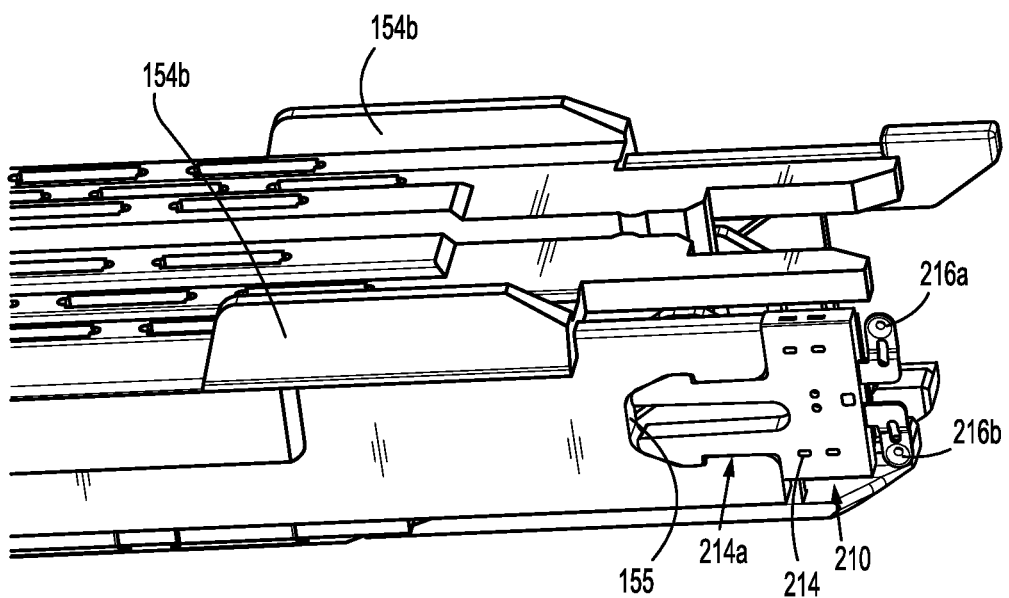
FIG. 13 is a side, perspective view of a chip assembly of the identification assembly shown in FIG. 8 secured to a cartridge body of the loading unit shown in FIG. 2.
Figure 14:
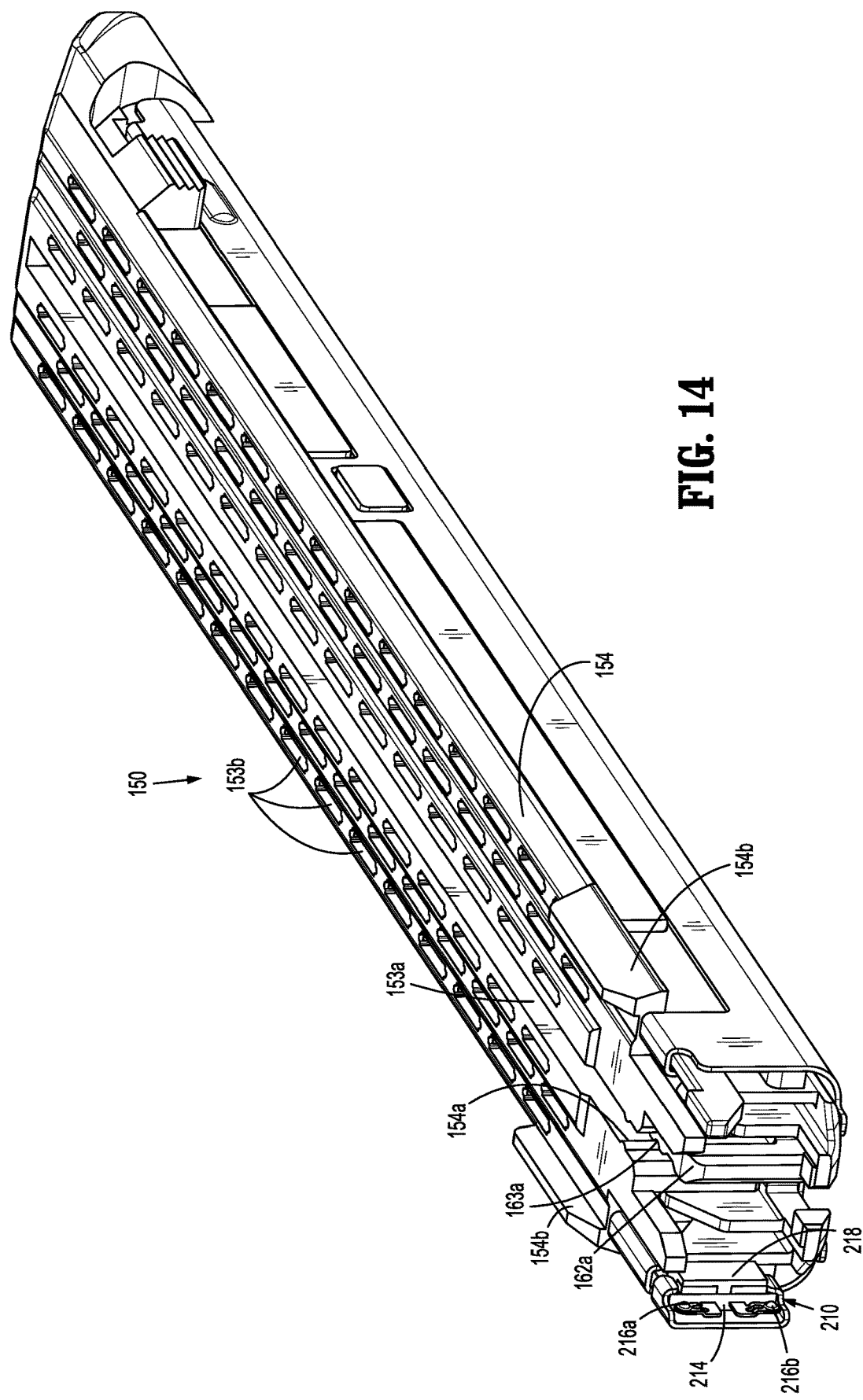
FIG. 14 is a perspective end view of a cartridge assembly of the loading unit shown in FIG. 2 including the chip assembly shown in FIG. 13.

With reference to FIGS. 5-7, a connection assembly 190 is supported on a proximal end of the upper housing half 110a of the proximal body portion 102 of the loading unit 100 and provides an electrical connection between the loading unit 100 and the surgical stapler 10 (FIG. 1). The connection assembly 190 includes a connector housing 192, a contact member 194, and an electronic chip 196. The contact member 194 includes a pair of contact portions 194a that are received within the recesses 193 of the connector 192. The contact portions 194a are positioned to engage corresponding contact portions (not shown) of a contact member (not shown) disposed within the elongate body 14 (FIG. 1) of the surgical stapler 10 (FIG. 1). The contact member 194 includes a connector portion 194b that extends between the contact portions 194a. As described above, a conductor, e.g., electrical ribbon or cable "R1" or wires, extends through the proximal body portion 102 of the loading unit 100 and into the tool assembly 104 to electrically couple the connection assembly 190 with the identification assembly 200 (FIG. 8).

During attachment of the loading unit 100 to the elongate body 14 (FIG. 1) of the surgical stapler 10 (FIG. 1), the contact portions 194a of the contact member 194 of connection assembly 190 are positioned to engage the contact portions (not shown) of a connector assembly (not shown) supported within a distal end of the elongate body 14 (FIG. 1) of the surgical stapler 10 (FIG. 1). Engagement of the contact members 194a of the connection assembly 190 with the contact members of the connector assembly of the surgical stapler 10 connects the identification assembly 200 (FIG. 8) of the loading unit 100 with the handle assembly 12 (FIG. 1) of the surgical stapler 10 (FIG. 1). As noted above, the loading unit 100 may be attached to the elongate body 14 with a bayonet coupling or in any other suitable manner.

With reference now to FIGS. 8-17, the identification assembly 200 of the loading unit 100 includes a connector assembly 202 and a chip assembly 212. The connector assembly 202 includes a connector housing 204. A tab 206a and a protrusion 206b extend outwardly from connector housing 204. The tab 206a is received within an opening 157a (FIG. 10) in the jaw member 156 of the tool assembly 104 to align the connector housing 204 with the jaw member 156 and the protrusion 206b is received within an opening 157b (FIG. 10) in the jaw member 156 to secure the connector assembly 202 to the jaw member 156. The connector housing 204 receives a distal end of the conductor, e.g., electrical ribbon "R1" (FIG. 11), that extends from the connection assembly 190 (FIG. 6) to electrically communicate the contact member 194 of the connection assembly 190 (FIG. 7) with the first and second contact members 206a, 206b. In embodiments, electrical ribbon "R1" is soldered to the first and second contact members 206a, 206b and the connector housing 204 is molded about the distal end of the electrical ribbon "R1" and the first and second contact members 206a, 206b to secure the electrical ribbon "R1" with the first and second contact members 206a, 206b. The contact members 206a, 206b extend distally from the connector housing 204 when the connector housing 204 is secured to the jaw member 156.

The chip assembly 212 includes a chip housing 214 and an identification chip 218. A projection 214a extends from the chip housing 214 and is received within a recess 155 (FIG. 12) formed in a proximal end of the cartridge body 154 (FIG. 12) of the cartridge assembly 150 to secure the chip assembly 212 to the cartridge body 154. The chip assembly 212 further includes first and second contact members 216a, 216b that extend from the chip housing 214 and communicate with the identification chip 218.

The first and second contact members 216a, 216b engage the respective first and second contact members 206a, 206b of the connector assembly 202 when the cartridge body 154 is received within the jaw member 156 (FIG. 16). In embodiments, and as shown, the first and second contact members 206a, 206b of the connector assembly 202 and first and second contact members 216a, 216b of the chip assembly 212 are supported on the connector housing 204 and the chip housing 214, respectively, in a cantilevered fashion to permit engagement between the first contact members 206a, 216a and between the second contact members 206b, 216b. The first and second contact members 206a, 206b of the connector assembly 202 and the first and second contact members 216a, 216b of the chip assembly 212 may include a substantially spherical shape to facilitate engagement between the connector assembly 202 and the chip assembly 212.

The identification chip 218 may include any commercially available chip capable of storing information including specifications of the cartridge assembly 150, e.g., cartridge size, staple arrangement, staple length, clamp-up distance, production date, model number, lot number, expiration date, etc., and transmitting at least some of the information to the handle assembly 12 (FIG. 1). In one embodiment, the identification chip 218 includes an erasable programmable read only memory ("EPROM") chip. In this manner, the configuration of an attached cartridge assembly 150 may be relayed to the handle assembly 12 such that, for example, the firing forces and/or the length of the firing stroke of the handle assembly 12 may be adjusted to accommodate the particular cartridge assembly 150. It is envisioned that instead of an EPROM, the identification chip 218 may be a read/write memory chip, such as read/write RAM, such that data may be written onto the identification chip 218. For example, usage information may be written onto the identification chip 218 that identifies that the loading unit 100 has been fully or partially fired to prevent reuse of an empty or partially fired loading unit, or for any other purpose.

Figure 18:
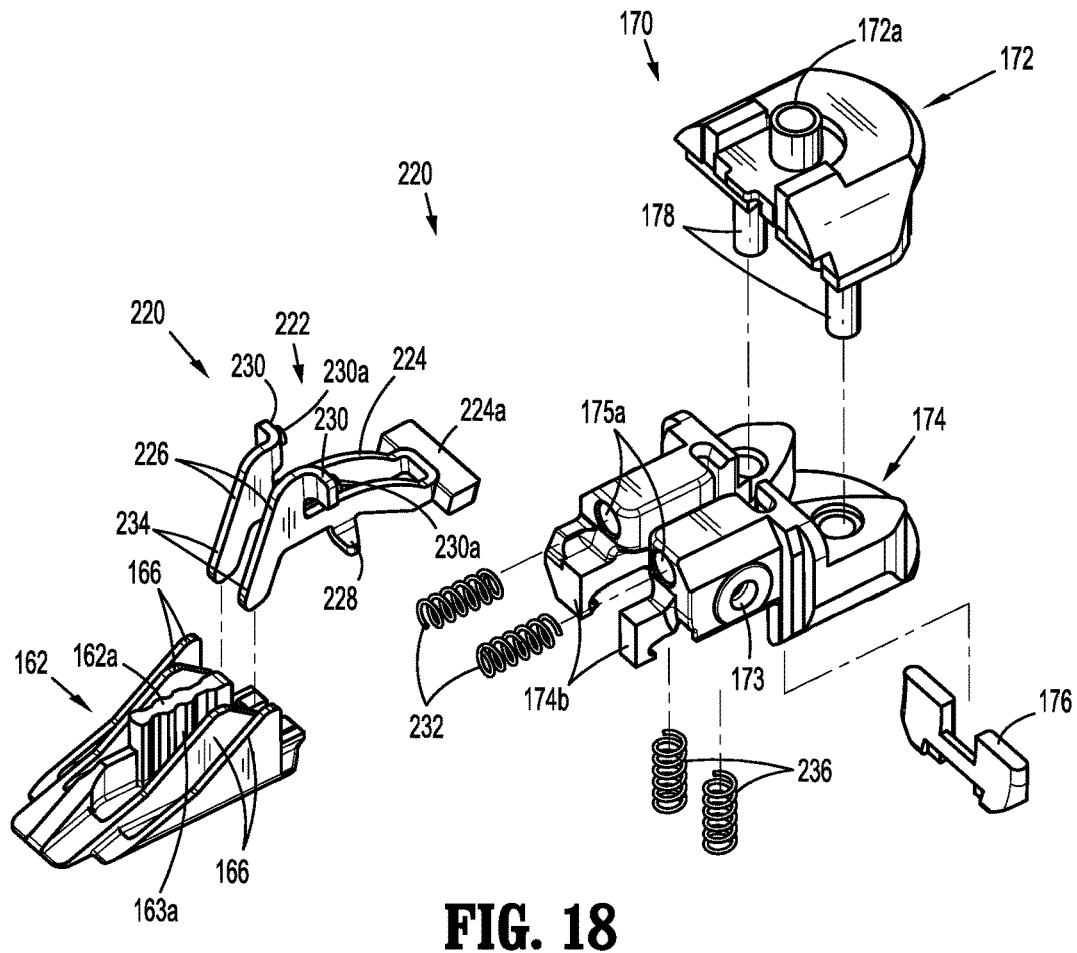
FIG. 18 is a perspective view of the mounting assembly and firing lockout assembly shown in FIG. 4 with parts separated.

With particular reference to FIGS. 16-18, as the cartridge assembly 150 is received within the jaw member 156 of the loading unit, the first and second contact members 216a, 216b of the chip assembly 212 engage the first and second contact member 206a, 206b of the connector assembly 202. Once the first and second contact members 216a, 216b of the chip assembly 212 are engaged with the respective first and second contact members 206a, 206b of the connector assembly 202, information stored on the identification chip 218 of the chip assembly 212 may be relayed to the handle assembly 12 upon connection of the loading unit 100 to the body portion 14 of the surgical stapler 10. As described above, the identification assembly 200 is connected to the surgical stapler 10 (FIG. 1) via a conductor, e.g., electrical ribbon or cable "R1" (FIGS. 7 and 11), extending through the loading unit 100 and by the connection assembly 190 (FIG. 6) which is disposed within a proximal end of the loading unit 100.

The firing lockout assembly 220 will now be described with reference to FIGS. 18-28. The firing lockout assembly 220 is substantially similar to the firing lockout assembly described in U.S. patent application Ser. No. 14/230,516 ("the '516 application"), filed Mar. 31, 2014, and will only be described in detail with reference to the differences therebetween. Accordingly, the content of the '516 application is incorporated by reference herein in its entirety.

The firing lockout assembly 220 includes a latch member 222 which is pivotally supported on a distal end of the lower mounting portion 174. The latch member 222 includes a U-shaped body (FIG. 19) having a proximal base member 224 and two spaced distally extending legs 226. As shown, the base member 224 is provided with a blocking member 224a which defines a blocking surface and is welded or secured to the base member 224 to provide additional support to the base member 224. Alternatively, the base member 224 and the blocking member 224a are integrally or monolithically formed. The latch member 222 is pivotal from a first position (FIG. 21) to a second position (FIG. 22). In the first position shown in FIG. 21, the blocking member 224a of the latch member 222 is aligned with the stop surface 184a of the drive member 182 to prevent advancement of the drive member 182 within the tool assembly 104. In the second position shown in FIG. 22, the blocking member 224a is misaligned with the stop surface 184a of the drive member 182 to permit advancement of the drive member 182 within the tool assembly 104.

Figure 19:
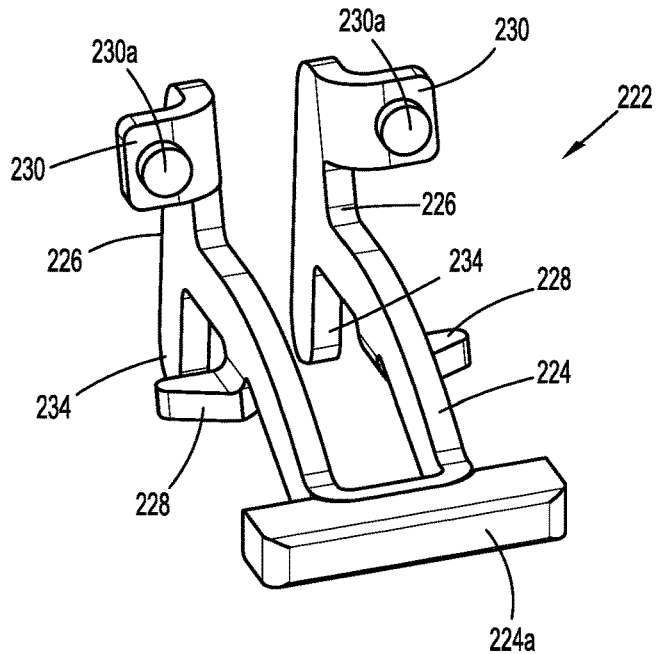
FIG. 19 is an enlarged perspective view of a latch member of the firing lockout assembly shown in FIG. 18.
Figure 20:
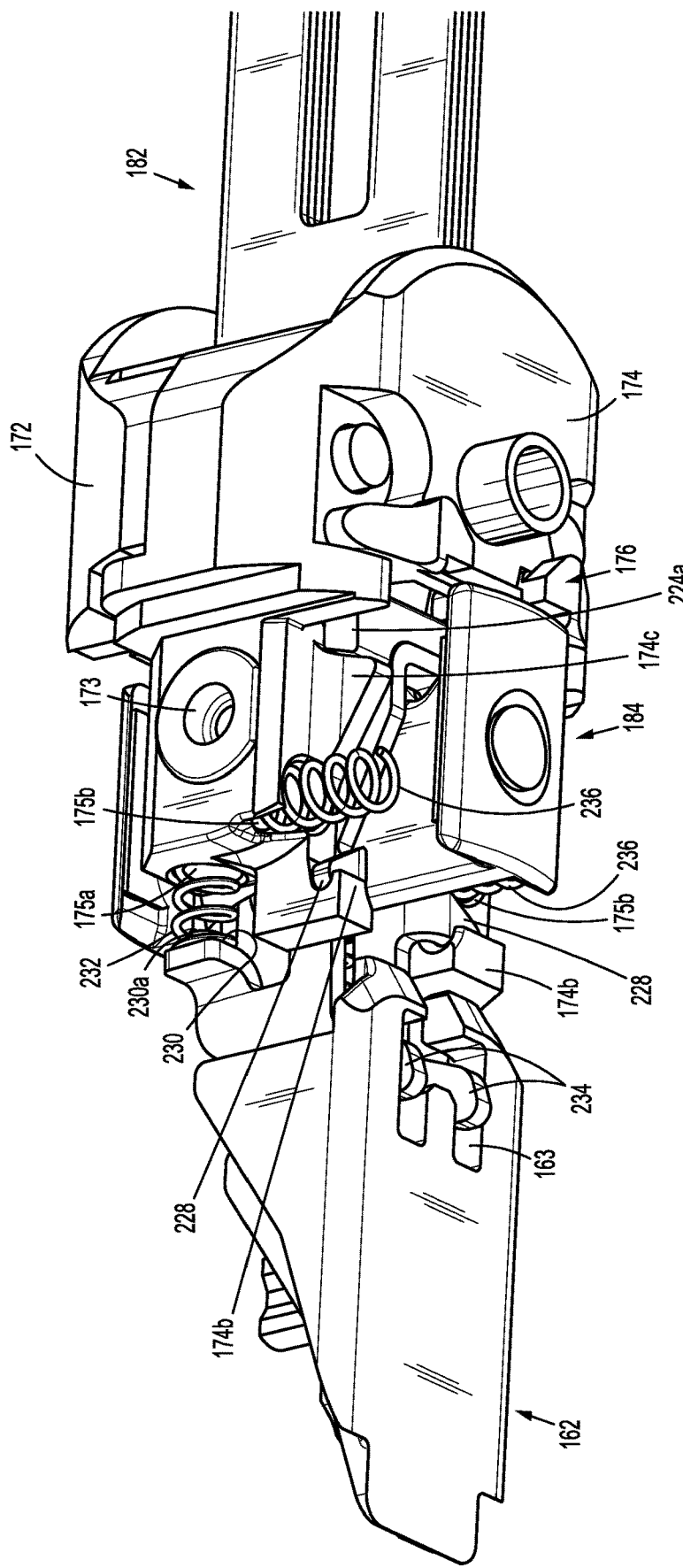
FIG. 20 is a bottom, perspective view of the firing lockout assembly and the mounting assembly shown in FIG. 18 and distal end of a drive assembly of the loading unit shown in FIG. 2.

With particular reference to FIGS. 18-20, each of the legs 226 of the latch member 222 has a centrally located pivot member 228 and an abutment surface 230. The pivot members 228 are supported on hooked arms 174b (FIG. 20) of the lower mounting portion 174 of the mounting assembly 170 to pivotally support the latch member 222 on the lower mounting portion 174. A biasing member includes a pair of springs 232 (FIG. 18) which is supported within respective bores 175a (FIG. 18) formed in a distal face of the lower mounting portion 174 to urge the latch member 222 towards the first position. Each of the springs 232 is positioned to engage a nub 230a formed on the respective abutment surfaces 230 of the latch member 222 to bias the latch member 222 in a counter-clockwise direction as viewed in FIG. 24. A distal end of each of the legs 226 includes a downwardly extending projection 234 which is positioned to extend through an opening 163 (FIG. 20) defined in the sled 162 when the sled 162 is in a retracted position, the latch member 222 is in the first position, and the anvil assembly 130 and the cartridge assembly 150 are in an approximated position.

A pair of springs 236 is positioned between the inner surface 156b (FIG. 10) of the jaw member 156 and a respective bore 175b (FIG. 20) defined in a bottom surface of the lower mounting portion 174 to urge the tool assembly 104 to the unapproximated position (FIG. 2). Jaw member 156 includes a pair of cylinders 158 (FIGS. 10 and 11) for engaging springs 236.

Figure 25:
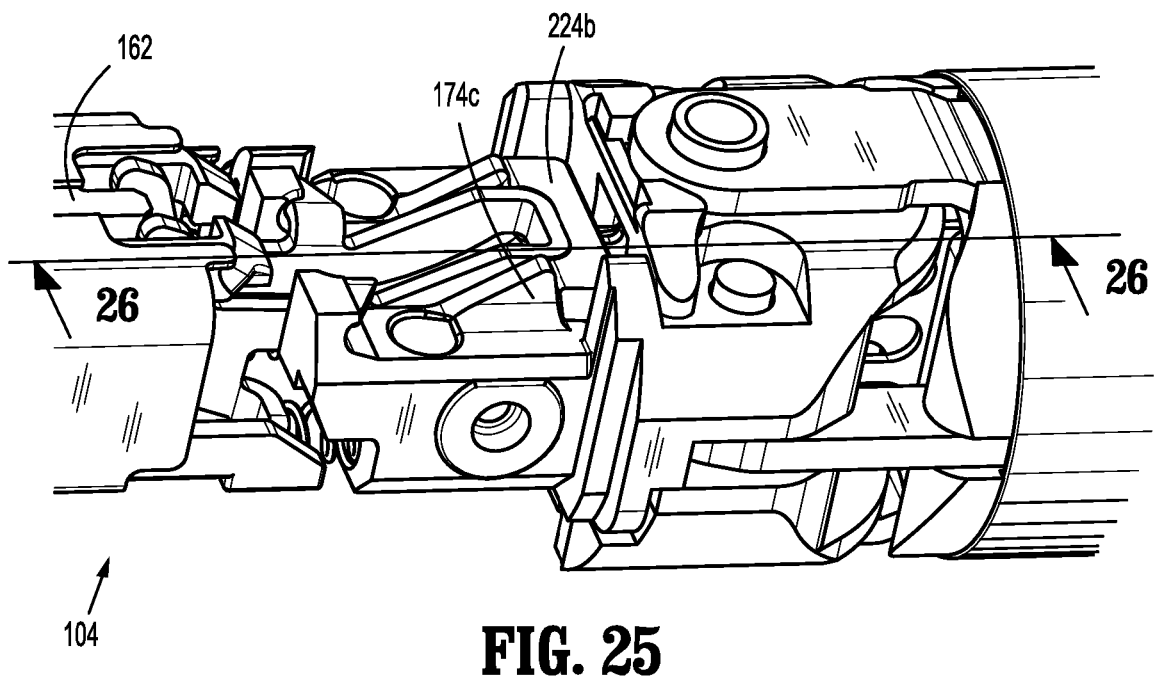
FIG. 25 is a side, perspective view of the firing lockout assembly shown in FIG. 18.

Referring to FIGS. 23 and 24, when the drive member 182 is in the fully retracted position and the tool assembly 104 is in the unapproximated or open position, the upper and lower flanges 186a, 186b of the working end 184 of the drive member 182 are spaced proximally of the sled 162 and proximally of cam surfaces 238a, 238b formed on the anvil plate 134 and the jaw member 156, respectively. In the unapproximated position of the tool assembly 104, the latch member 222 is urged towards a counter-clockwise position by springs 232. The lower mounting portion 174 includes a surface 240 which is positioned to engage the base member 224 or blocking member 224a. Engagement between the blocking member 224a and the surface 240 of the lower mounting portion 174 prevents further counter-clockwise rotation of the latch member 222 to retain the latch member 222 in the first position. As shown in FIG. 25, the blocking member 224a engages a gusset 174c of the lower mounting portion 174 to prevent distal movement of the latch member 222 when the firing lockout assembly 220 is in the locked configuration.

Figure 26:
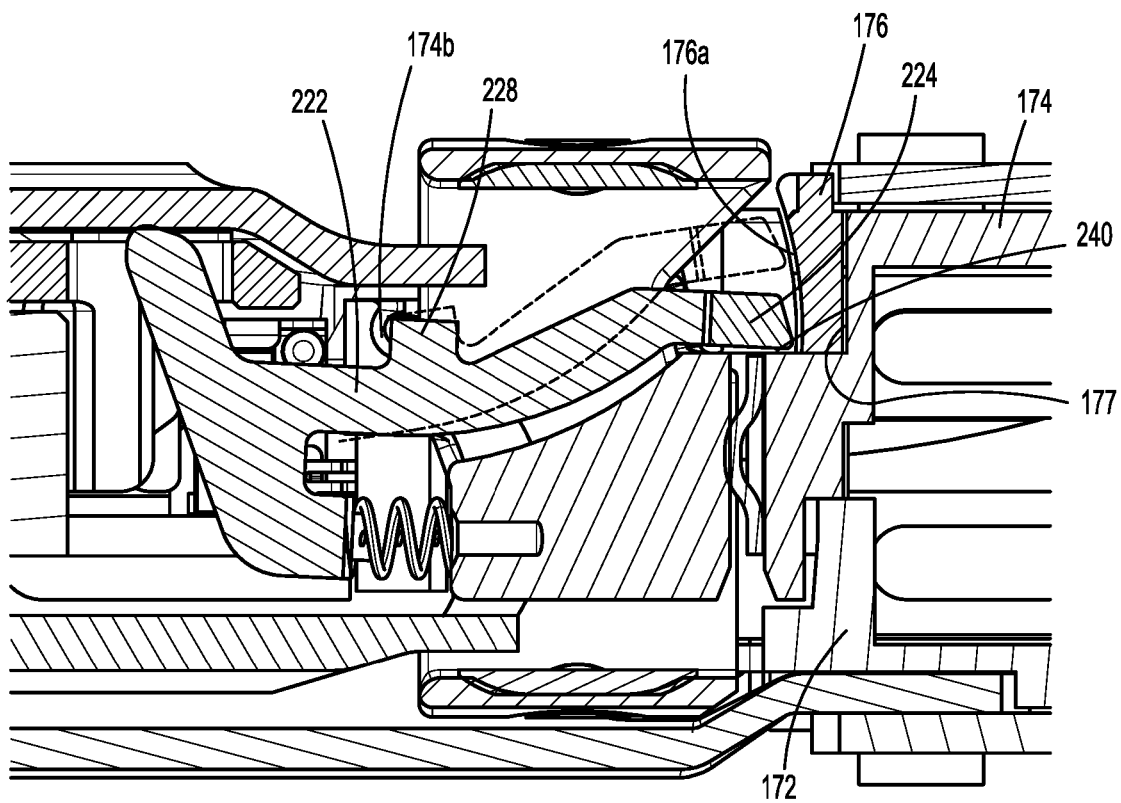
FIG. 26 is a side, cross-sectional view taken along line 26-26 shown in FIG. 25.

The operation of the firing lockout assembly 220 is described in detail in the '516 application. Briefly, during firing of the loading unit 100, the latch member 222 of the firing lockout assembly 220 is pivoted about the pivot members 174b of the lower mounting portion 174. As described above, the retention blade 176 is received within slot 177 in the lower mounting portion 174. As illustrated in FIG. 26, the curved surface 176a of the retention blade 176 accommodates the arcuate motion of the blocking member 224a of the latch member 222 to prevent proximal movement of the latch member 222 during firing of the loading unit 100. Proximal movement of the latch member 222 could cause the pivot members 228 to separate from the hooked arms 174b of the lower mounting portion 174. Separation of the latch member 222 from the lower mounting portion 174 during firing of the loading unit 100 may result in misfiring of the loading unit 100 and/or prevent the firing lockout assembly 220 from functioning properly.

Prior to firing of the loading unit 100, the tool assembly 104 may be articulated relative to the proximal body portion 102. During articulation of the tool assembly 104, limiting member 176b of retention blade 176 engages the second coupling member 114b which extends from the proximal body portion 102 of the loading unit 100 to limit the articulation of the tool assembly 104 relative to the proximal body portion 102.

With reference to FIGS. 29 and 30, the shipping wedge 300 of cartridge assembly 150 is configured to maintain staples "S" (FIG. 3) within staple retention slots 153b of cartridge body 154 and prevent actuation of tool assembly 104 of loading unit 100 prior to removal. The shipping wedge 300 includes an elongate body 302 defining an elongate recess 303 (FIG. 30) along a bottom surface of the elongate body. A flange 304 extends from within the elongated recess 303 and includes a plurality of protrusions 304 for securing the flange 304 within the elongate slot 153a (FIG. 14) of the cartridge body 154 (FIG. 29). A proximal end of the elongate body 302 includes a raised portion 306 (FIG. 29) configured to prevent approximation of the cartridge assembly 150 (FIG. 2) towards the anvil assembly 130 (FIG. 2) once the cartridge assembly 150 is loaded within the jaw member 156 (FIG. 2) of the tool assembly 104 and prior to removal of the shipping wedge 300. A distal end of the elongate body 302 includes a projection 308 which is positioned and configured to be grasped by a clinician to facilitate separation of the shipping wedge 300 from the cartridge assembly 150. A plurality of tabs 310 extend from the elongate body 302 for engaging the cartridge body 154 of the cartridge assembly 150 to releasable secure the shipping wedge 300 to the cartridge body 154 of cartridge assembly 150.

In some embodiments, the projection 308 of the shipping wedge 300 may be used to remove the cartridge assembly 150 from the jaw member 156 after use. The cartridge body 154 can define a recess (not shown) adjacent the jaw member 156 when the cartridge assembly 150 is disposed in the jaw member 156. The shipping wedge 300 is grasped by the user and the projection 308 is inserted into the recess. The shipping wedge 300 may then be manipulated (by twisting, pivoting, etc.) to pop the cartridge assembly 150 out so that it can be removed and possibly replaced.

Figure 31:
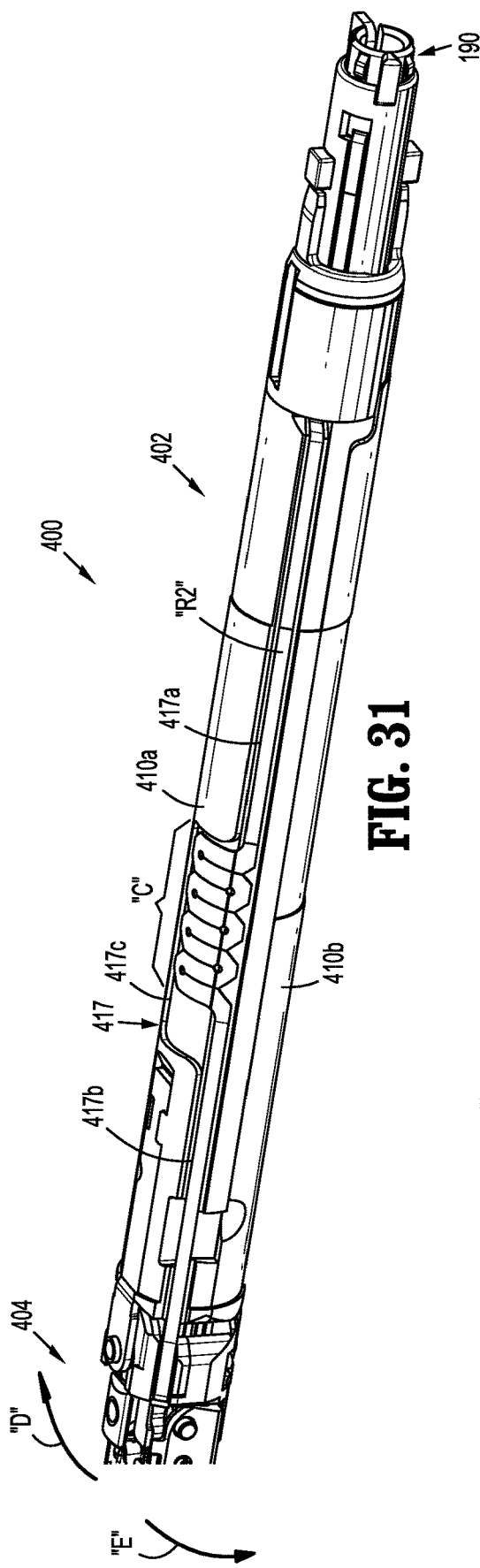
FIG. 31 is a side, perspective view of a loading unit according to another embodiment of the present disclosure, including a flexible cable.
Figure 32:
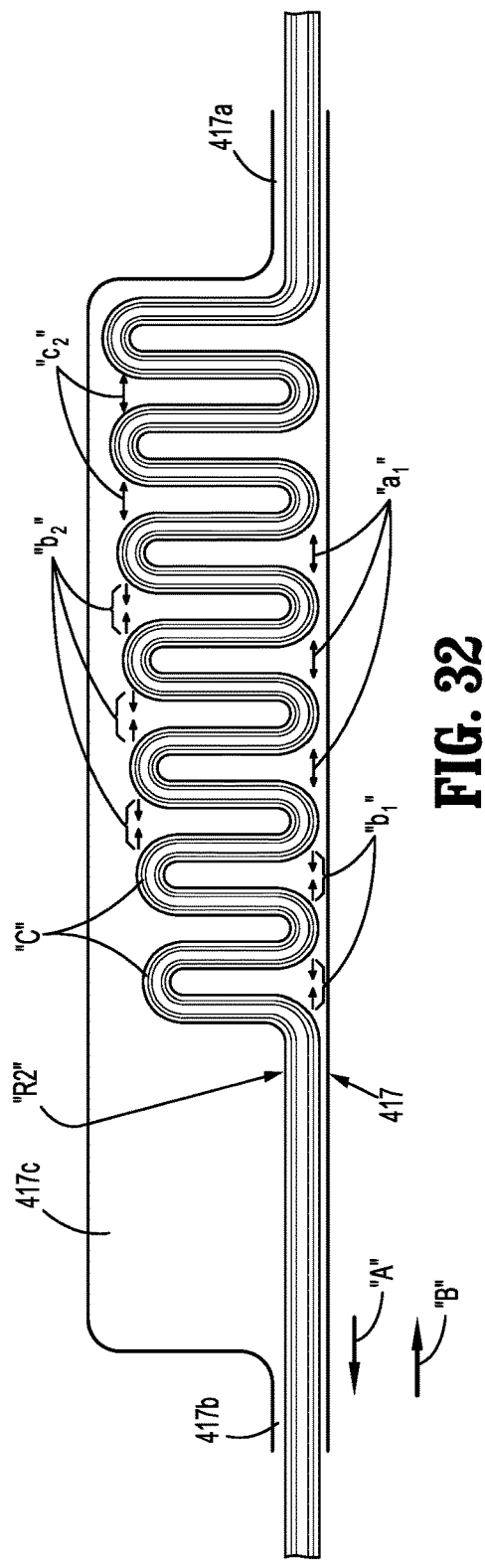
FIG. 32 is a schematic view of the flexible cable of the loading unit shown in FIG. 31.

With reference now to FIGS. 31 and 32, a loading unit according to another embodiment of the present disclosure is shown generally as loading unit 400. The loading unit 400 is substantially similar to the loading unit 100 described hereinabove and will only be described as relates it to the differences therebetween.

The loading unit 400 includes an electrical conductor, i.e., a flexible cable or electrical ribbon "R2", for electrical coupling the connection assembly 190, disposed on a proximal end of the proximal body portion 402 of the loading unit 400, with an identification assembly 200 (FIG. 8), disposed within the tool assembly 404 of the loading unit 400. The flexible cable "R2" includes a strain relief portion. The strain relief portion is an undulating portion of the cable, enabling the loading unit to articulate and still carry the cable. The strain relief portion has at least one bend and can include a plurality of coils "c". As shown, the flexible cable "R2" includes seven (7) coils "c" of decreasing height from a proximal portion of the flexible cable "R2" to a distal portion of the flexible cable "R2". It is envisioned that flexible cable "R2" may include more or less than seven (7) coils "c" and/or that the height of the coils may increase from the proximal portion to the distal portion. Alternatively, the heights of the coils "c" may be uniform or vary in a random or uniform manner. Although shown as having uniform spacing between the coils "c", it is envisioned that the spacing between the coils "c" may be different.

The strain relief portion may be biased to an initial configuration. For example, the material and shape of the cable biases the cable to the coiled configuration shown in FIGS. 31 and 32. During articulation, as described below, the undulating shape of the strain relief portion will open up. Upon returning the tool assembly to a straighter configuration, less articulated position, or non-articulated position, the undulating shape, or coiled shape will close, eventually returning to the initial configuration in the non-articulated position.

During articulation of the tool assembly 404 of the loading unit 400 relative to the proximal body portion 402 of the loading unit 400, the flexible cable "R2" experiences strain. The strain experienced by the flexible cable "R2" is a result of the distance between the connection assembly 190 proximal body portion 402 and the identification assembly 200 disposed within the tool assembly 404 changing as the tool assembly 404 articulates relative to the proximal body portion 402. In particular, the distance between the connection assembly 190 and the identification assembly 200 increases as the tool assembly 404 articulates in a first direction, as indicated by arrow "D" in FIG. 31, and the distance between the connection assembly 190 and the identification assembly 200 decreases as the tool assembly 404 articulates in a second direction, as indicated by arrow "E" in FIG. 31.

The coils "c" of the flexible cable "R2" allow the flexible cable "R2" to have a variable length by deforming in response to a strain on the flexible cable "R2". In particular, when tension is applied to a distal end of the flexible cable "R2", as indicated by arrow "A" in FIG. 32, flexion of each coil "c", as indicated by arrows "$a_1$" in FIG. 32, and/or outward flexion of the coils "c" relative to each other, as indicated by arrows "$a_2$" in FIG. 32, permits the flexible cable "R2" to lengthen, thereby relieving the strain on the flexible cable "R2". When compression is applied to the flexible cable "R2", as indicted by arrow "B" in FIG. 32, inward flexion of each coil "c", as indicated by arrows "$b_1$,", and/or inward flexion of the coils "R2" relative to each other, as indicted by arrows "$b_2$" in FIG. 32, permits the flexible cable "R2" to shorten, thereby relieving the strain on the flexible cable "R2".

The proximal body portion 402 of loading unit 400 includes an upper housing half 410a and a lower housing half 410b. A channel 417 extends a length of upper housing half 410a and receives the flexible cable "R2". The channel 417 includes proximal and distal portions 317a, 417b for receiving the proximal and distal portions of the flexible cable "R2", and a central portion 417c for receiving the coils "c" of the flexible cable "R2" and accommodating the flexion of the coils "c" when the flexible cable "R2" is experiencing strain.

The flexible cable "R2" extends the length of the proximal body portion 402 of loading unit 400 and into the tool assembly 404 of loading unit 400. The flexible cable "R2" electrically couples the connection assembly 190 disposed with the proximal body portion 302 of the loading unit 400 with the identification assembly 200 (FIG. 8) disposed within the tool assembly 404 of the loading unit 400. The flexible cable "R2" may be loosely received within the channel 417 to permit longitudinal movement of the flexible cable "R2". In one embodiment, the proximal end of flexible cable "R2" is axially fixed within the proximal portion 417a of the channel 417 using, e.g., adhesives, over-molding.

As described above, the flexible cable "R2" extends between a proximal end of the body portion 402 of the loading unit 400 and the tool assembly 404 of the loading unit 400. During articulation of the tool assembly 404 of the loading unit 400 relative to the proximal body portion 402 of the loading unit 400, a strain, i.e., tension or compression, is experienced by the flexible cable "R2". In particular, articulating of the tool assembly 404 relative to the proximal body portion 402 in a first direction, as indicated by arrow "D" in FIG. 31, creates a pulling force on distal end of the flexible cable "R2", as indicated by arrow "A" in FIG. 32, and articulating of the tool assembly 404 relative to the proximal body portion 402 in a second direction, as indicted by arrow "E" in FIG. 31, creates a pushing force on the distal end of the flexible cable "R2", as indicated by arrow "B" in FIG. 32. To accommodate the strain experienced by the flexible cable "R2" during articulation of the tool assembly 404, and thereby prevent breaking and/or buckling of the flexible cable "R2", as described above, the coils "c" of the flexible cable "R2" are configured to flex individually, and relative to each other. As the coils "c" flex outwardly, the flexible cable "R2" stretches, and as the coils "c" flex inwardly, the flexible cable "R2" compresses. Return of the tool assembly 404 to the non-articulated position causes the coils "c" of the flexible cable "R2" to return to the non-strained configuration.

Although shown and described as being incorporated into the loading unit 400, it is envisioned that the flexible cable "R2" may be incorporated into any device having an articulating tool assembly and requiring electrical coupling of the articulating tool assembly to a handle assembly.

With reference now to FIGS. 33-61, a loading unit according to another embodiment of the present disclosure is shown generally as loading unit 500. The loading unit 500 is substantially similar to the loading unit 100 described hereinabove and will only be described in detail as relates to the differences therebetween.

Figure 34:
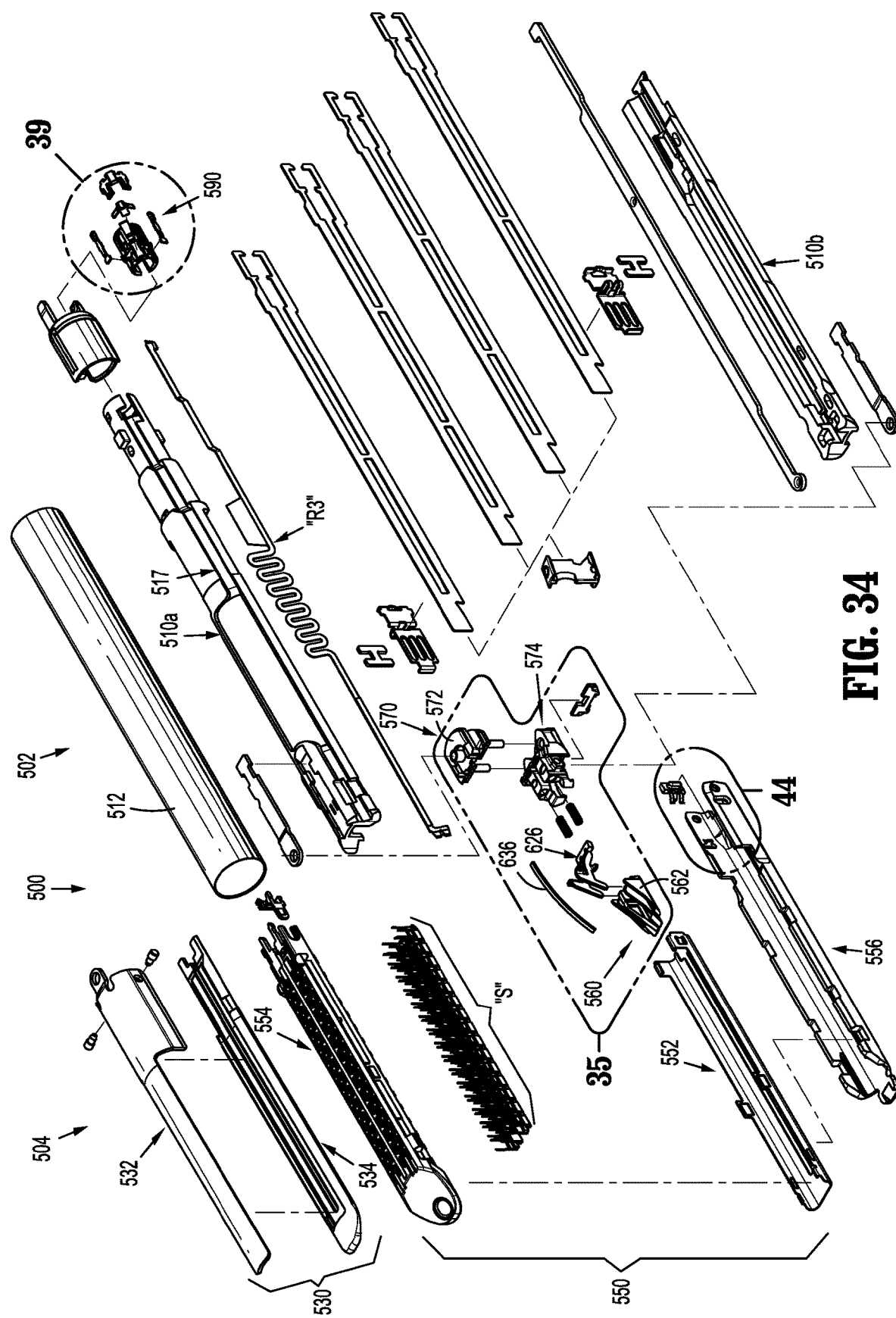
FIG. 34 is a side, perspective view of the loading unit shown in FIG. 33 with parts separated.

With reference to FIG. 34, a proximal body portion 502 of the loading unit 500 includes an upper housing half 510a and a lower housing half 510b which are contained within an outer sleeve 512. A channel 517 extends the length of upper housing half 510a for receiving a conductor, e.g., flexible cable "R3". As will be described in further detail below, flexible cable "R3" electrically couples a connection assembly 590 disposed in a proximal end of the proximal body portion 502 of the loading unit 500 with an identification assembly 600 (FIG. 43) disposed within the tool assembly 504 of the loading unit 500 and the cartridge assembly 550.

Still referring to FIG. 34, the tool assembly 504 includes an anvil assembly 530 and the cartridge assembly 550 and a jaw member 556. The anvil assembly 530 includes an anvil body 532 and an anvil plate 534. The cartridge assembly 550 is received within the jaw member 556 and includes a support plate 552, a cartridge body 554, a plurality of staples "5", and a staple firing assembly 560 which includes an actuation sled 562 configured to translate through the cartridge body 554. The actuation sled 562 defines a plurality recesses 561 (FIG. 36) for increasing the structural integrity of the actuation sled 562. The recesses 561 in the actuation sled 562 also reduce the amount of material necessary to form the actuation sled 562.

Figure 35:
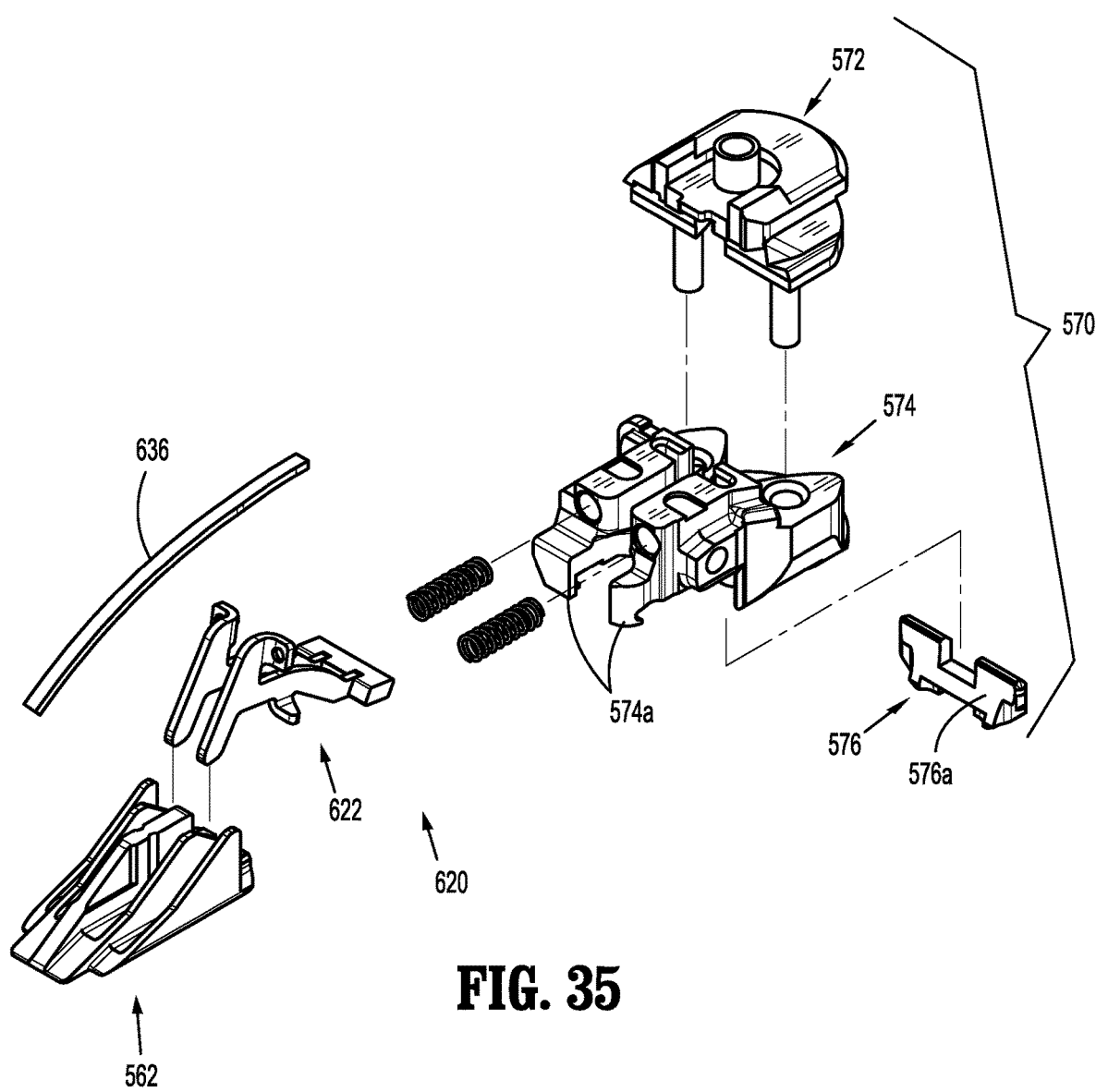
FIG. 35 is a side perspective view of the indicated area of detail shown in FIG. 34 showing a mounting assembly and a firing lockout assembly.

Referring also to FIG. 35, a mounting assembly 570 and a firing lockout assembly 620 of the loading unit 500 are substantially similar to the mounting assembly 170 and the firing lockout assembly 220 described above. Briefly, the mounting assembly 570 includes upper and lower mounting portions 572, 574 and a retention blade 576 welded to the lower mounting portion 574 in a proximal position. The firing lockout assembly 620 includes a latch member 622 having pivot members 628 that pivotally support the latch member 622 on hooked arms 574a (FIG. 37) of the lower mounting portion 574 and a proximal base member 624 that moves relative to a curved surface 576a of the retention blade 576.

Figure 36:
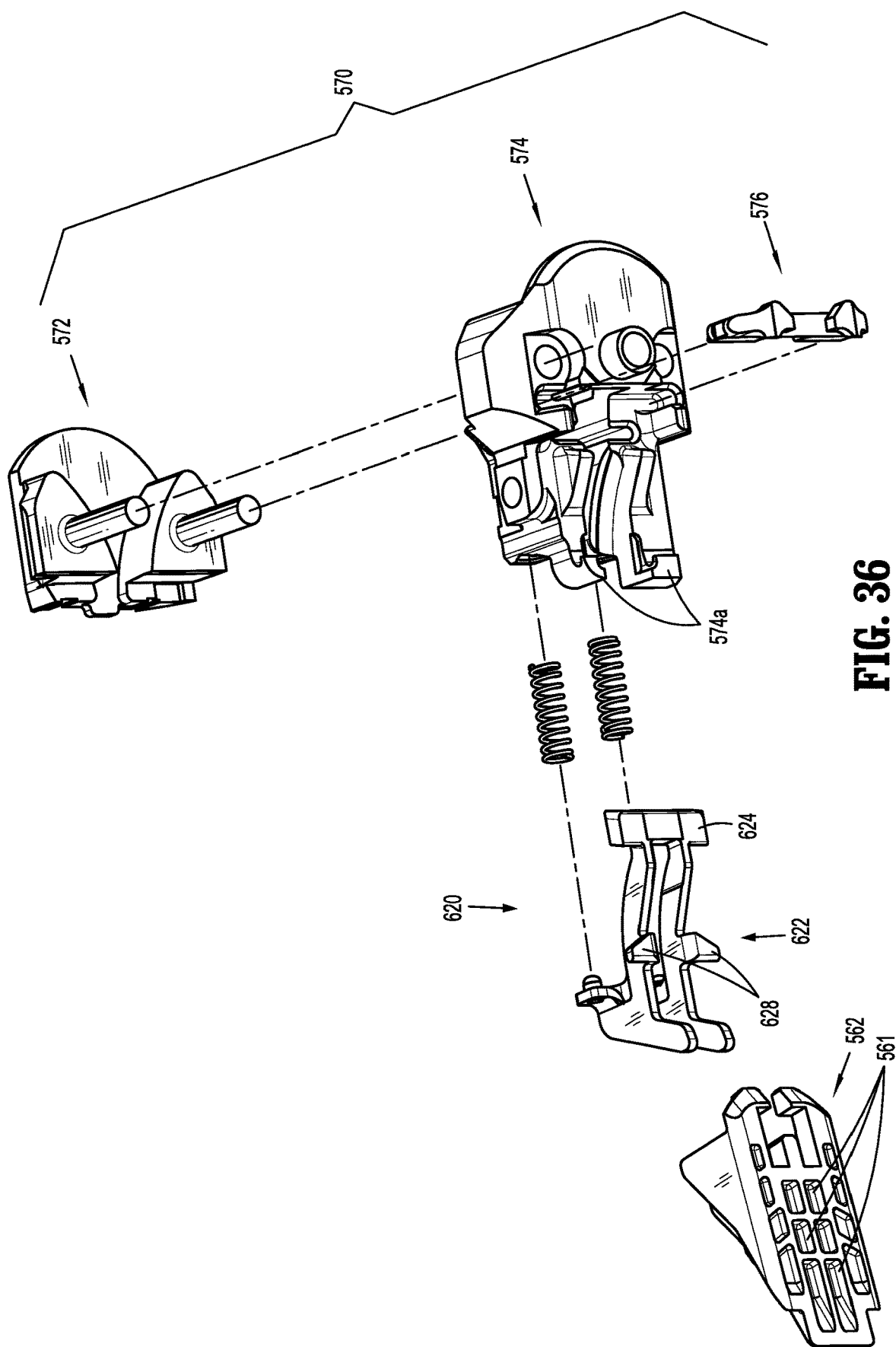
FIG. 36 is a perspective bottom view of the mounting assembly and the firing lockout assembly shown in FIG. 35 with parts separated.
Figure 37:
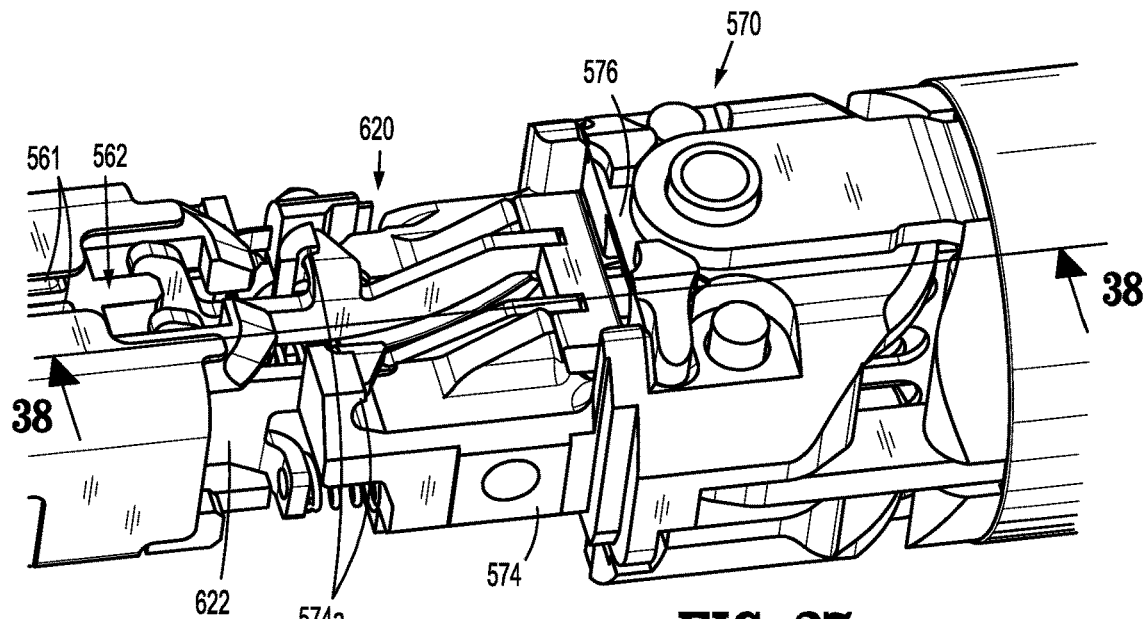
FIG. 37 is a side, perspective view of the firing lockout assembly shown in FIG. 35.
Figure 38:
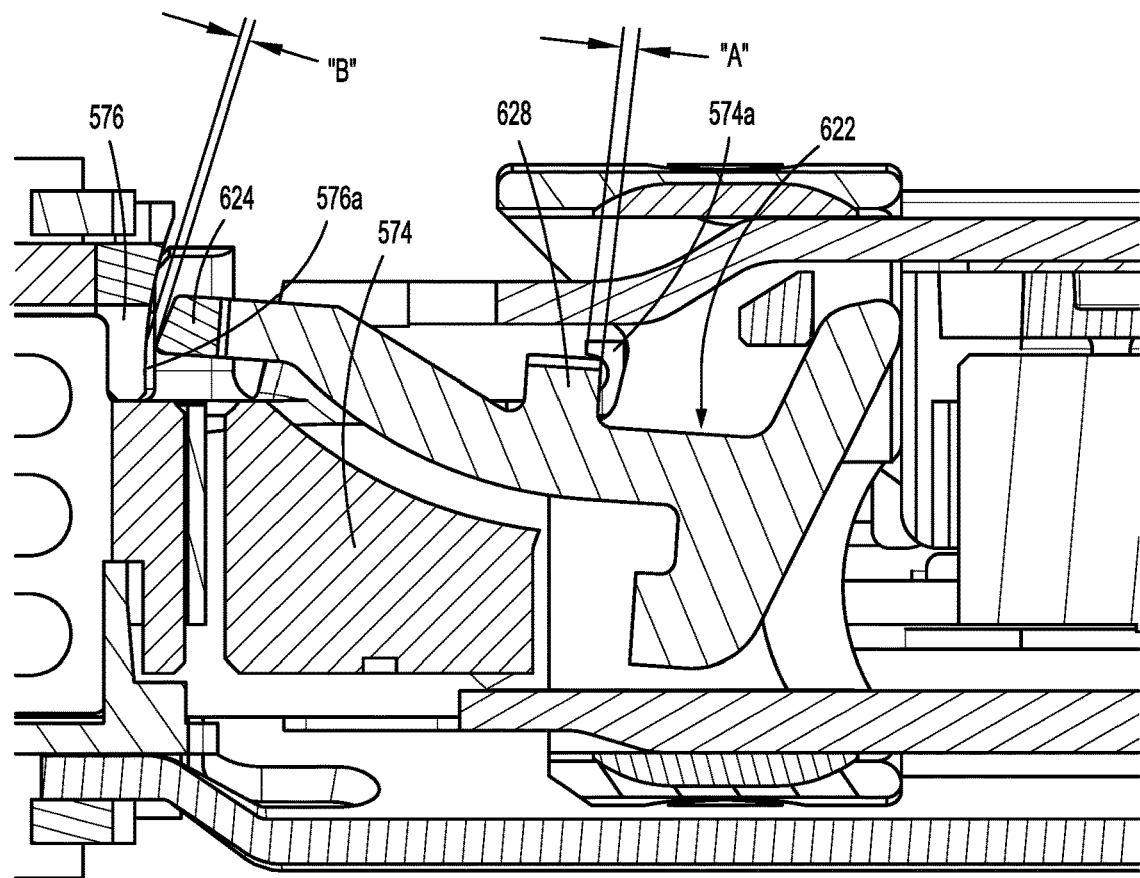
FIG. 38 is a side, cross-sectional view taken along line 38-38 shown in FIG. 37.

Referring also to FIGS. 36-38, to prevent the latch member 622 from disengaging from the hooked arms 574a of the lower mounting portion 574, the hooked arms 574a of the lower mounting portion 574 include a length "A" (FIG. 38) which is greater than the distance "B" (FIG. 38) between the proximal base member 624 of the latch member 622 and the curved surface 576a of the retention blade 576. In this manner, the latch member 622 is prevented from moving proximally a distance sufficient to separate from the hooked arms 574a of the lower mounting portion 574.

Figure 33:
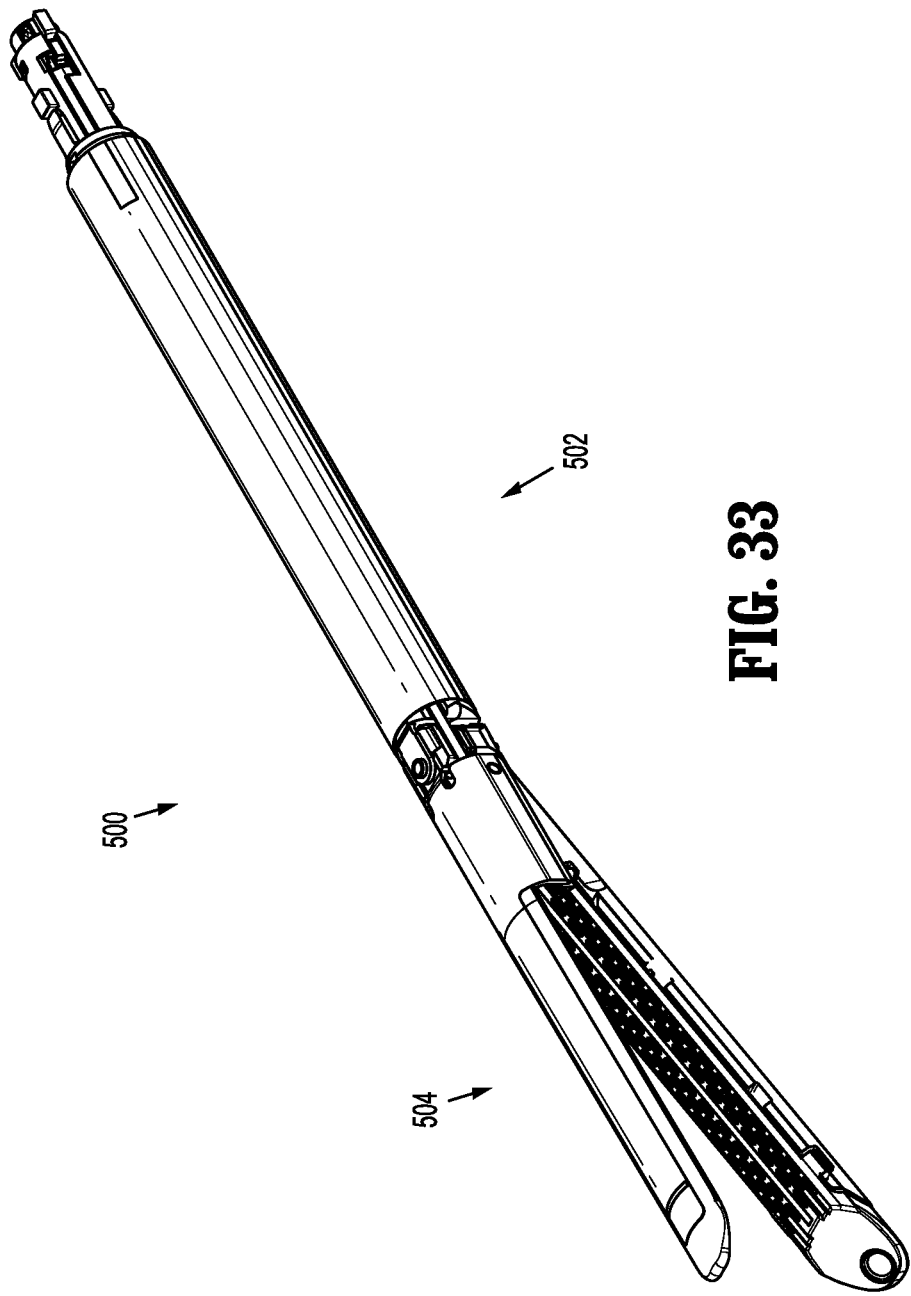
FIG. 33 is a side, perspective view of a disposable loading unit according to another embodiment of the present disclosure.

With particular reference to FIG. 35, a leaf spring 636 is secured to the lower mounting portion 574 of the mounting assembly 570 and is configured to engage the jaw member 556 to urge the tool assembly 504 to an unapproximated or open position (FIG. 33). The leaf spring 636 may be welded, adhered, or otherwise secured to the lower mounting portion 574.

Figure 39:
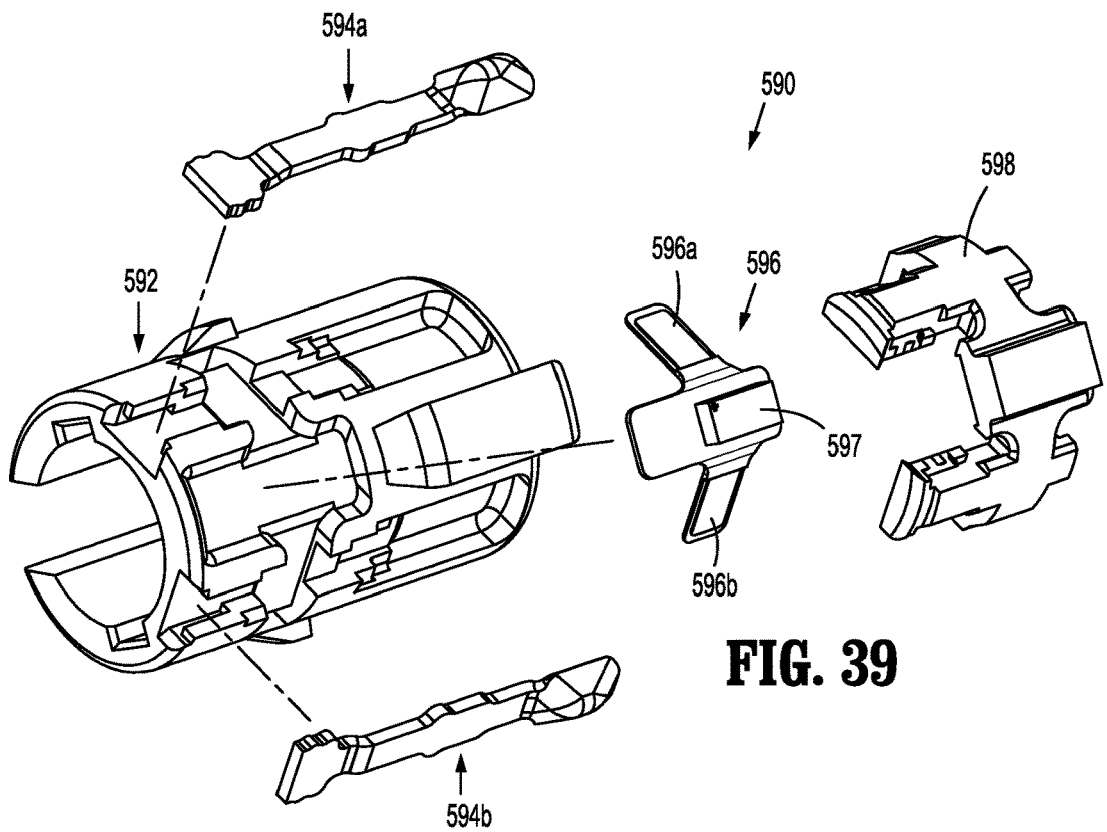
FIG. 39 is a side perspective view of the indicated area of detail shown in FIG. 34.
Figure 40:
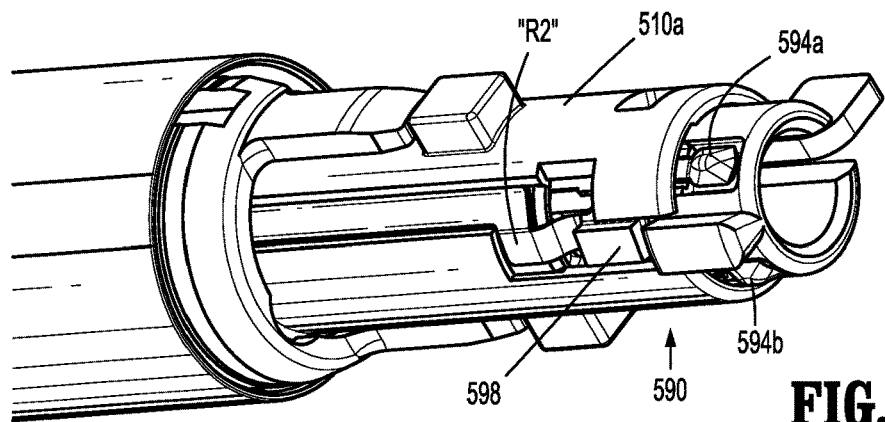
FIG. 40 is an enlarged perspective view of a proximal end of the loading unit shown in FIG. 33.
Figure 41:
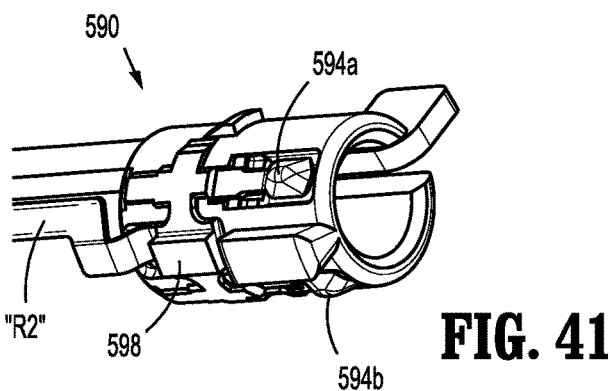
FIG. 41 is a side, perspective view of the proximal end of the loading unit shown in FIG. 40 with an upper housing half removed.
Figure 42:
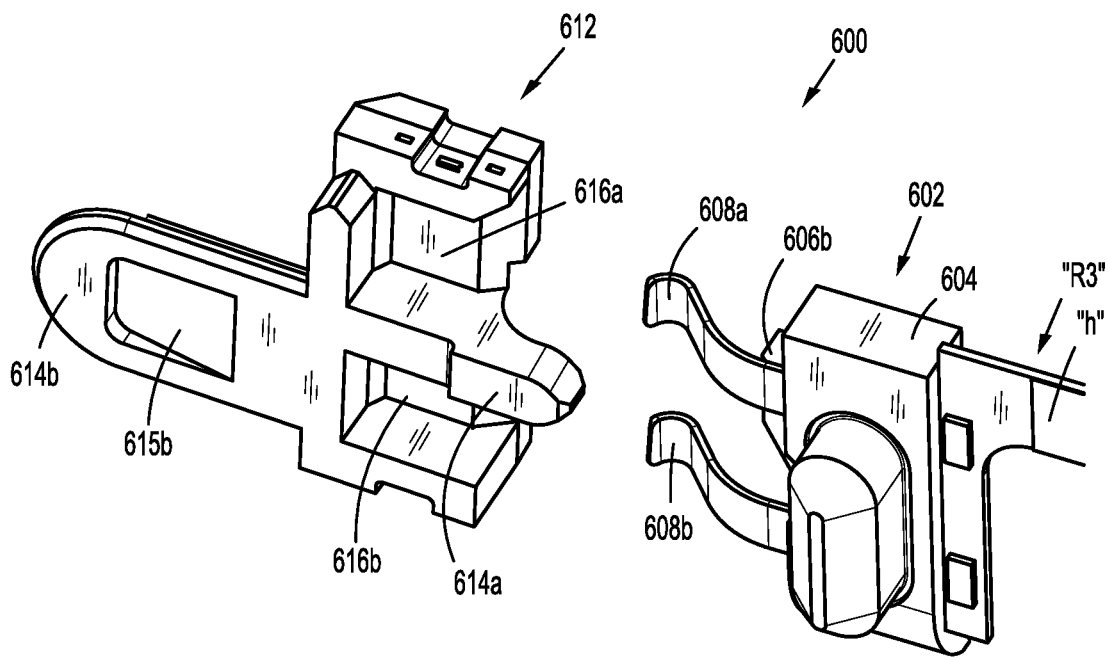
FIG. 42 is a side, perspective view of an identification assembly of the loading unit shown in FIG. 33 with parts separated.
Figure 43:
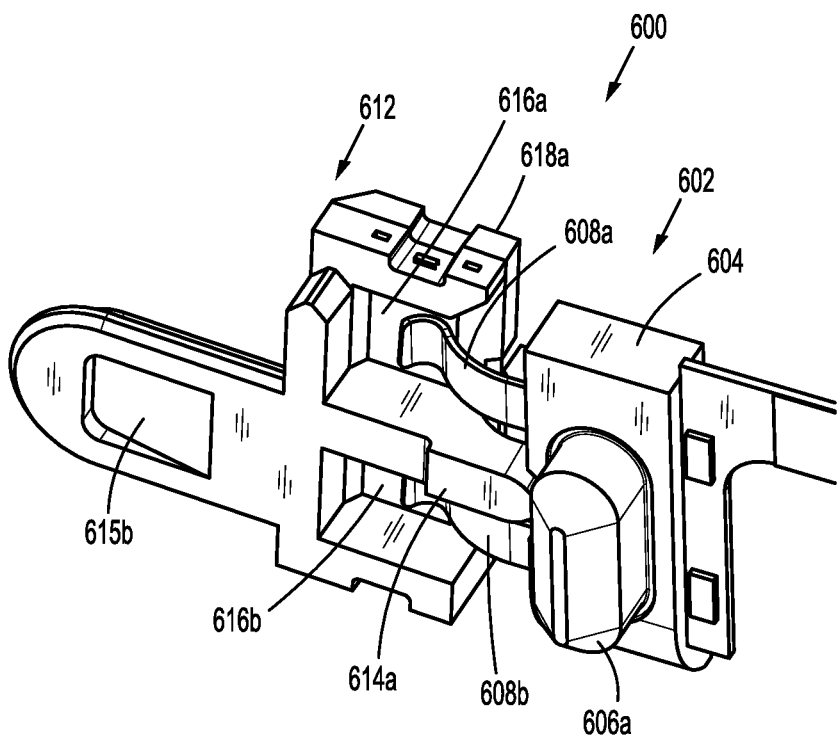
FIG. 43 is a side, perspective view of the identification assembly shown in FIG. 42.
Figure 44:
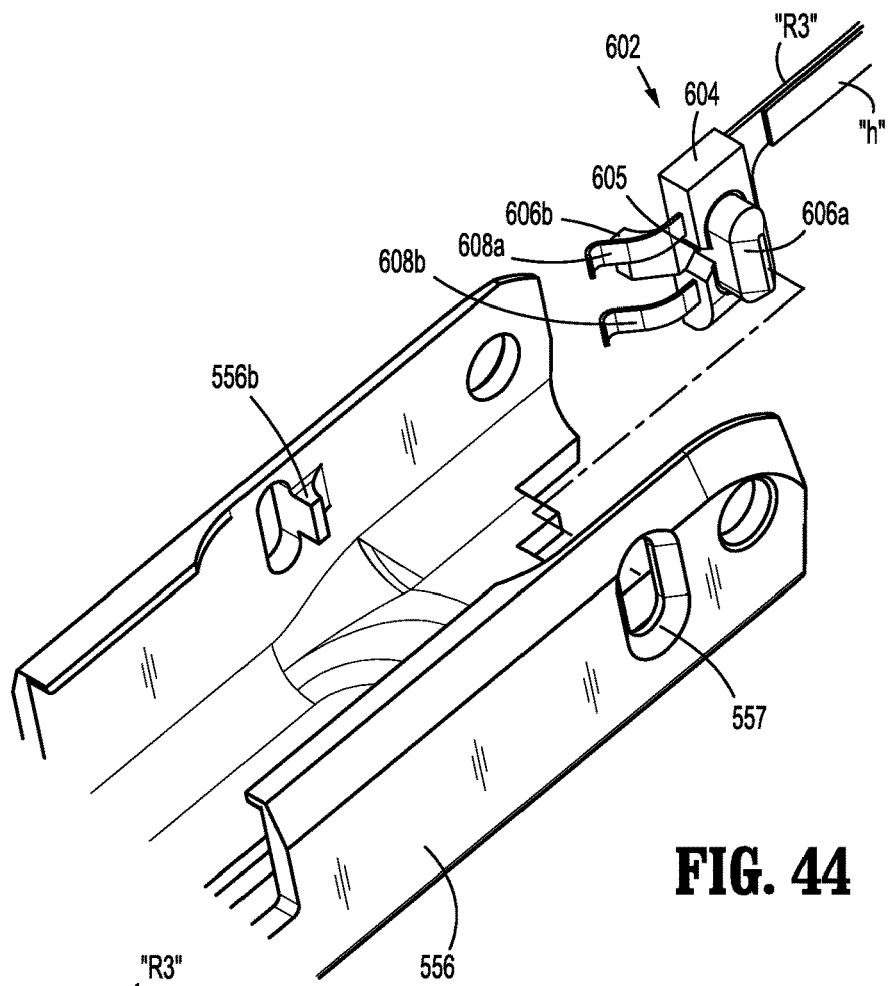
FIG. 44 is a perspective view of a connector assembly of the identification assembly shown in FIG. 42 and a proximal end of a jaw member of the loading unit shown in FIG. 33 with parts separated.
Figure 45:
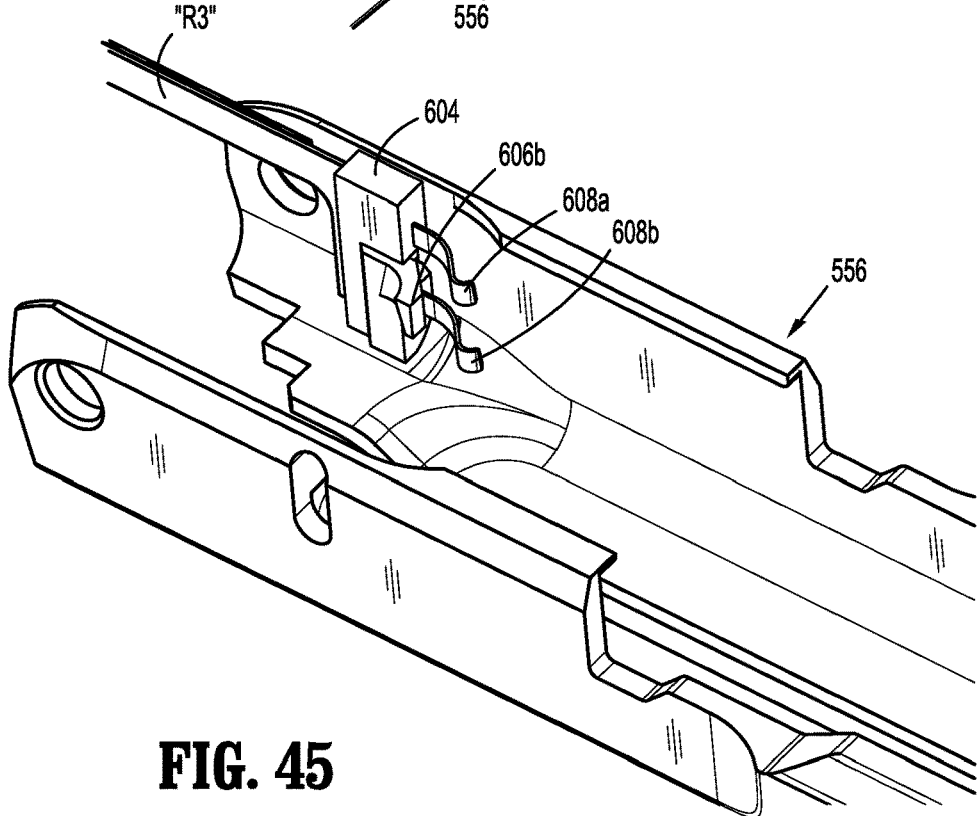
FIG. 45 is an alternative perspective view of the connector assembly and jaw member shown in FIG. 44.

With reference to FIGS. 39-41, a connection assembly 590 is supported on a proximal end of the upper housing half 510a of the proximal body portion 502 of loading unit 500 and provides an electrical connection between the loading unit 500 and the surgical stapler 10 (FIG. 1). The connection assembly 590 includes a connector housing 592, first and second contact members 594a, 594b, and a connector member 596. The connector member 596 may be integrally formed with, or otherwise electrically connected to, a proximal end of the flexible cable "R3" (FIG. 34).

The connector member 596 includes first and second pads 596a, 596b for connection with the respective first and second contact members 594a, 594b. In one embodiment, the first and second pads 596a, 596b are formed of copper, and the first and second contact members 594a, 594b are soldered to the first and second pads 596a, 596b, respectively. The connector 596 may further include an electronic chip 597 (FIG. 39), i.e., an EPROM chip, for providing information regarding the configuration and/or the condition of the loading unit 500 to the surgical stapler 10 when the loading unit 500 is secured to the surgical stapler 10.

The first and second contact members 594a, 594b and the connector member 596 are secured to the connector housing 592 using adhesives, friction fit, or in any other suitable manner. In one embodiment, and as shown, the first and second contact members 594a, 594b and the connector member 596 are secured to the connector housing 592 by an overmold 598. The overmold 598 may also protect the electronic chip 597. The overmold 598 may be formed of, for example, santoprene or other suitable plastic. The first and second contact members 594a, 594b are positioned to engage corresponding contact portions (not shown) of a contact member (not shown) disposed within the elongate body 14 (FIG. 1) of the surgical stapler 10 (FIG. 1).

With reference now to FIGS. 42-51 the identification assembly 600 of the loading unit 500 is substantially similar to the identification assembly 200 of the loading unit 100 described hereinabove, and will only be described in detail as relates to the differences therebetween. The identification assembly 600 includes a connector assembly 602 and a chip assembly 612.

With particular reference to FIGS. 42-45, the connector assembly 602 includes a connector housing 604, a protrusion 606a extending from a first side of the connector housing 604, and an alignment feature 606b extending from an opposite side of the connector housing 604. The protrusion 606a is received within a slot 557 (FIG. 44) in the jaw member 556 to secure the connector assembly 602 to the jaw member 556. The protrusion 606a may be heat staked, adhered or otherwise secured to the jaw member 556 within the slot 557. The alignment feature 606b acts to guide the connector assembly 602 into engagement with the chip assembly 612 as the cartridge assembly 550 (FIG. 47) is received within the jaw member 556 in the event that the cartridge body 554 narrows, e.g., when the sled 562 (FIG. 36) is in distal position.

The connector housing 604 further includes first and second contact members 608a, 608b extending distally therefrom. The connector housing 604 receives a distal end of the flexible cable "R3" (FIG. 34) that extends from connection assembly 590 (FIG. 38) to electrically communicate the first and second contact members 594a, 594b of the connection assembly 590 (FIG. 40) with the respective first and second contact members 608a, 608b of the connector assembly 602. In embodiments, connector housing 604 is molded about the distal end of the flexible cable "R3" to secure the flexible cable "R3" with the first and second contact members 608a, 608b. The connector housing 604 defines a notch 605 (FIG. 44) between the first and second contact members 608a, 608b for facilitating alignment of the connector assembly 602 with the chip assembly 612.

Figure 46:
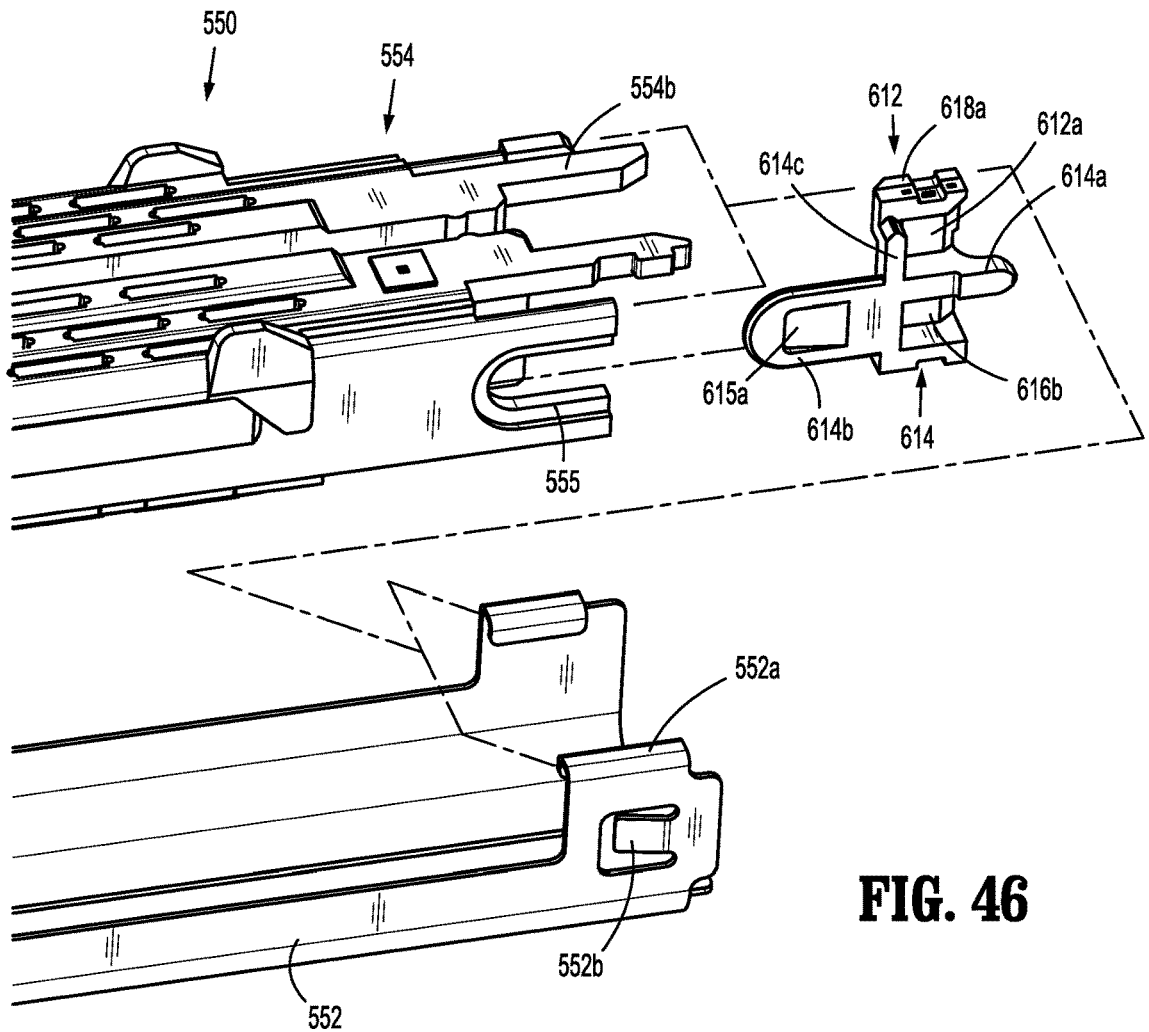
FIG. 46 is an enlarged view of the indicated area of detail shown in FIG. 34.
Figure 47:
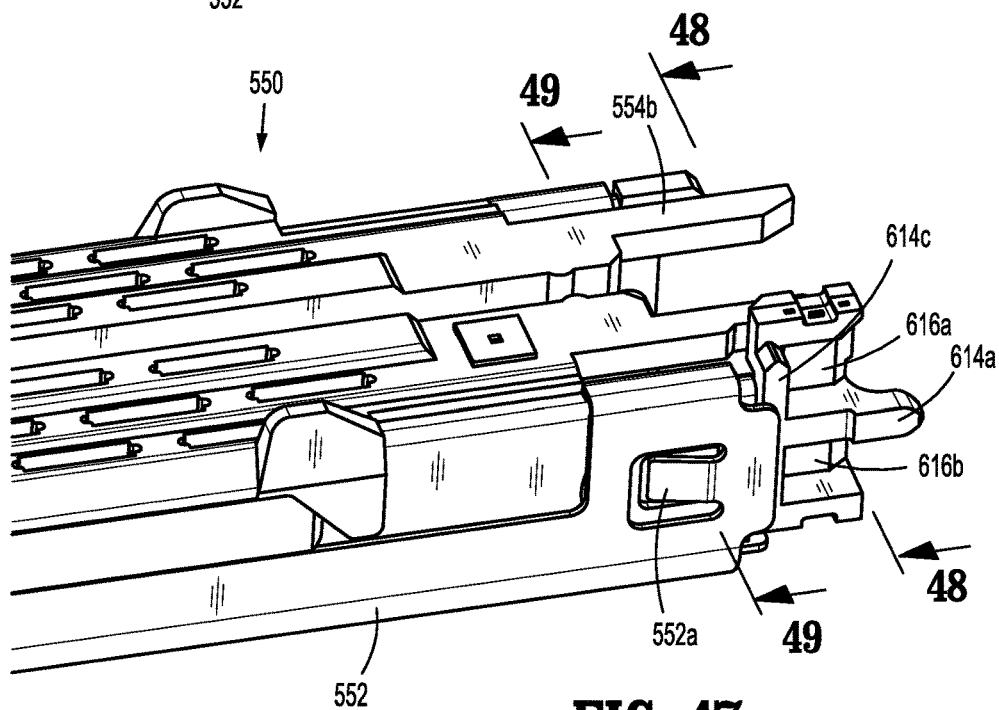
FIG. 47 is a side, perspective view of a chip assembly of the identification assembly shown in FIG. 42 secured to a cartridge body of the loading unit shown in FIG. 33 and received within a support plate of the loading unit.

With particular reference to FIGS. 46 and 47, the chip assembly 612 includes a chip housing 614 and an identification chip 618 (FIG. 48) protected by an overmold 618a. In one embodiment, the overmold 618a is formed of Santoprene®. A first projection 614a extends proximally from the chip housing 614 and facilitates alignment with the connector housing 604 of connector assembly 602. More particularly, the first projection 614a is configured to be received within the notch 605 (FIG. 44) formed in the connector housing 604 between the first and second contact members 608a, 608b. A second projection 614b extends distally from the chip housing 614 and is received within a recess 555 (FIG. 46) formed in a proximal end of the cartridge body 554 (FIG. 46) of the cartridge assembly 550 to attach the chip assembly 612 to the cartridge body 554. A third projection 614c extends in a vertical direction and engages a rail 552a of the support plate 552 to prevent vertical movement of the chip assembly 612 once the chip assembly is secured to the cartridge body 554 and the cartridge body 554 is secured within the support plate 552.

Figure 49:
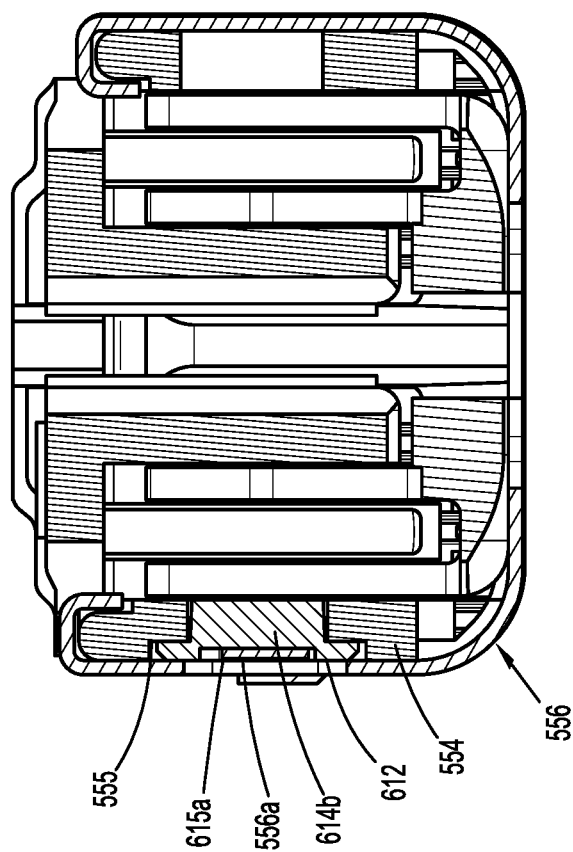
FIG. 49 is a cross-sectional end view taken along line 49-49 shown in FIG. 47.

As shown in FIG. 49, the recess 555 in the cartridge body 554 and the second projection 614b of the chip assembly 612 includes a stepped configuration which provides lateral support for the chip assembly 612. The second projection 614b of the chip housing 614 defines a notch 615a for receiving a tab 552b (FIG. 46) of the support plate 552. Receipt of the tab 552a of the support plate 556 within the notch 615a of the chip assembly 612 prevents proximal movement of the chip assembly 612 relative to the support plate 552 and the cartridge body 554.

With particular reference now to FIGS. 50 and 51, the chip housing 614 defines a notch 615b for receiving a protrusion 554a formed on a proximal end of the cartridge body 554. Receipt of the protrusion 554a of the cartridge body 554 within the notch 615b of the chip assembly 612 secures the chip assembly 612 to the cartridge body 554 when the second projection 614b is received within the recess 555 of the cartridge body 554. The chip assembly 612 forms an electrical and mechanical connection with the connector assembly.

Figure 48:
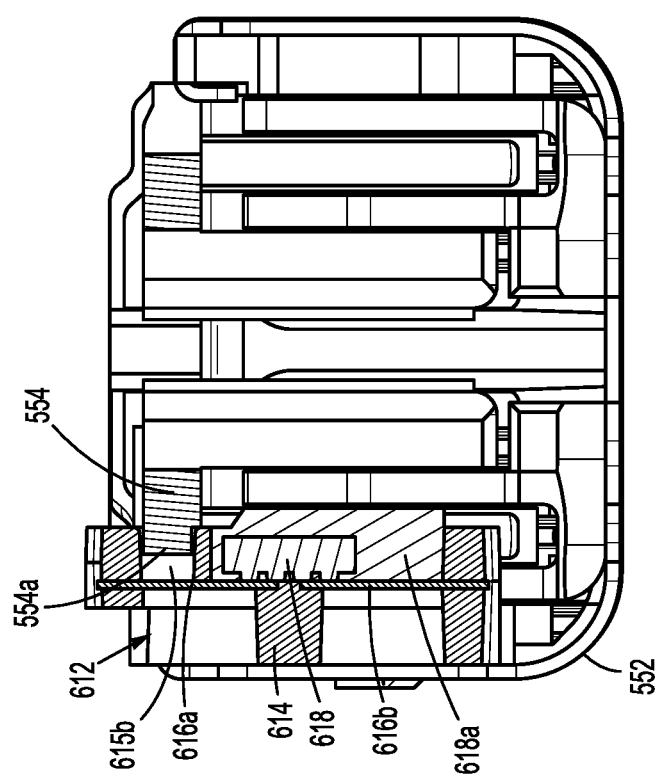
FIG. 48 is a cross-sectional end view taken along line 48-48 shown in FIG. 47.

The chip assembly 612 further includes first and second contact portions 618a, 618b that are electrically connected to the identification chip 618 (FIG. 48). In one embodiment, the first and second contact portions 618a, 618b are soldered to the identification chip 618 and the chip housing 614 forms an overmold that surrounds the first and second contact portions 618a, 618b. The overmold may be formed of, for example, Vectra® or other suitable material.

The first and second contact portions 616a, 616b engage the respective first and second contact members 608a, 608b of the connector assembly 602 when the cartridge body 554 is received within the jaw member 556 (FIG. 45) of the loading unit 500. In embodiments, and as shown, the first and second contact members 608a, 608b of the connector assembly 602 are supported on the connector housing 604 in a cantilevered fashion to ensure electrical contact between the first contact members 608a and the first contact portion 616a and between the second contact member 608b and the second contact portion 616b.

Figure 52:
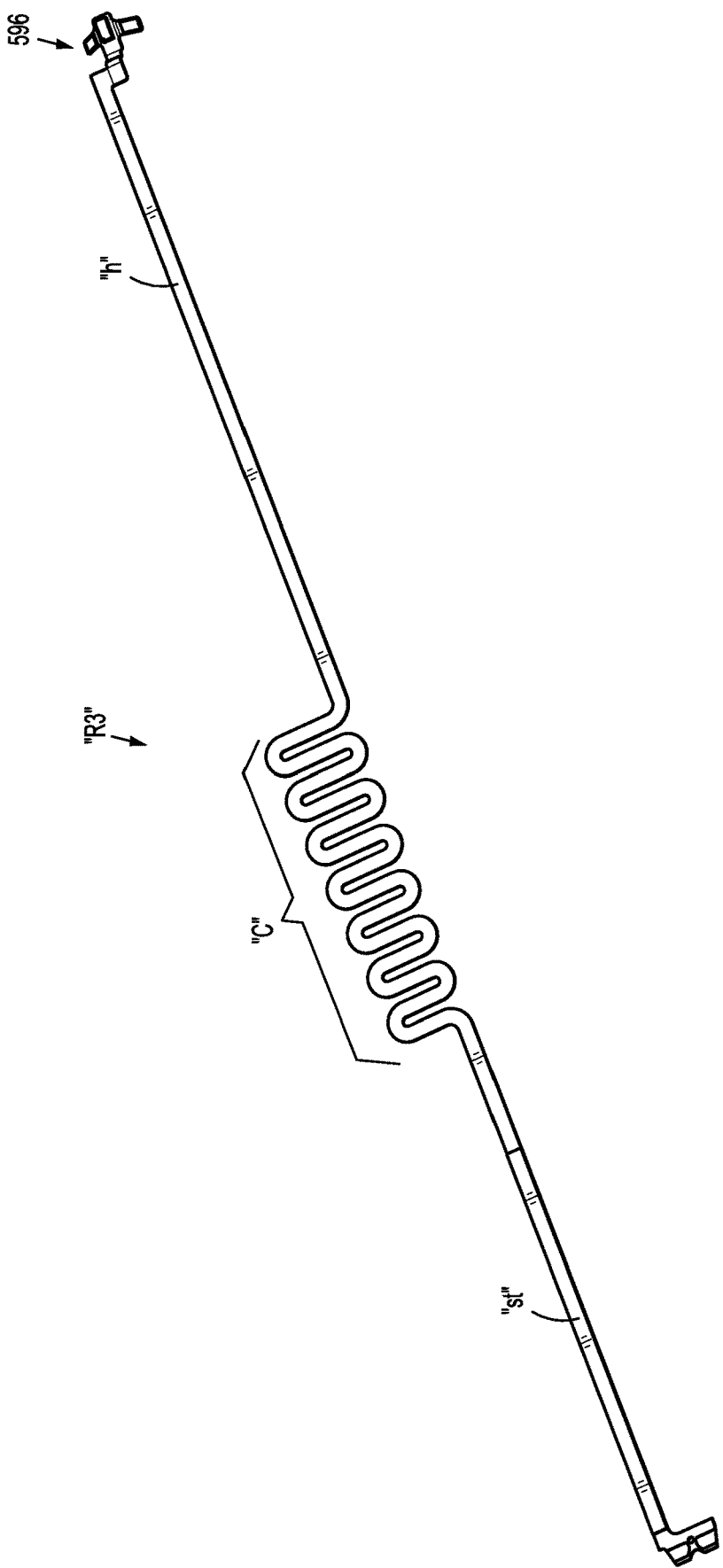
FIG. 52 is a perspective view of a flexible cable of the loading unit shown in FIG. 33.

Turning briefly to FIG. 52, the flexible cable "R3" is substantially similar to flexible cable "R2" described hereinabove. As noted above, the connector member 596 of the connection assembly 590 may be integrally formed with, or otherwise electrically coupled to, the proximal end of the flexible cable "R3". A distal end of the flexible cable "R3" is configured for electrical connection with the connector housing 604 of the connector assembly 602 of the identification assembly 600. The first and second contact members 608a, 608b may be soldered with, or otherwise electrically connected to, the distal end of the flexible cable "R3" and as noted above, the connector housing 604 may be overmolded to the distal end of the flexible cable "R3" to secure the connection between the flexible cable "R3" and the first and second contact members 608a, 608b.

The flexible cable "R3" includes a plurality of coils "c", an adhesive backing "h" along a proximal portion of the flexible cable "R3", and a stiffener portion "st" along a distal portion of the flexible cable "R3". The adhesive backing "h" may be formed of a PSA adhesive or other suitable material, and operates to adhere the flexible cable "R3" to the upper housing halve 510a (FIG. 34) of the proximal body portion 502 of loading unit 500. The stiffener portion "st" may be integrally formed with the cable "R3" or securely affixed thereto. The stiffener portion "st" facilitates sliding of the cable "R3" during articulation of the tool assembly 504. The stiffener portion "st" also helps to prevent buckling of the cable "R3" where the cable "R3" is not otherwise supported. The stiffener portion "st" may be formed of, for example, a polyimide material, and may be attached to a straight portion of the cable.

Turning to FIGS. 53 and 54, an alternative embodiment of a conductor, e.g., flexible cable or electrical ribbon, according to the present disclosure is shown generally as flexible cable "R4". In embodiments, the flexible cable "R4" is substantially similar to the electrical ribbon "R1" and each of the flexible cables "R2" and "R3" disclosed hereinabove, and will only be described in detail as relates to the differences therebetween.

Referring initially to FIG. 53, a proximal end of the flexible cable "R4" defines first and second openings "$O_1$", "$O_2$" for receiving first and second posts (not shown) of a connection assembly (not shown). Receipt of the first and second posts within the first and second openings "$O_1$", "$O_2$" of the flexible cable "R4" electrically couples the flexible cable "R4" with the connection assembly.

Figure 55:
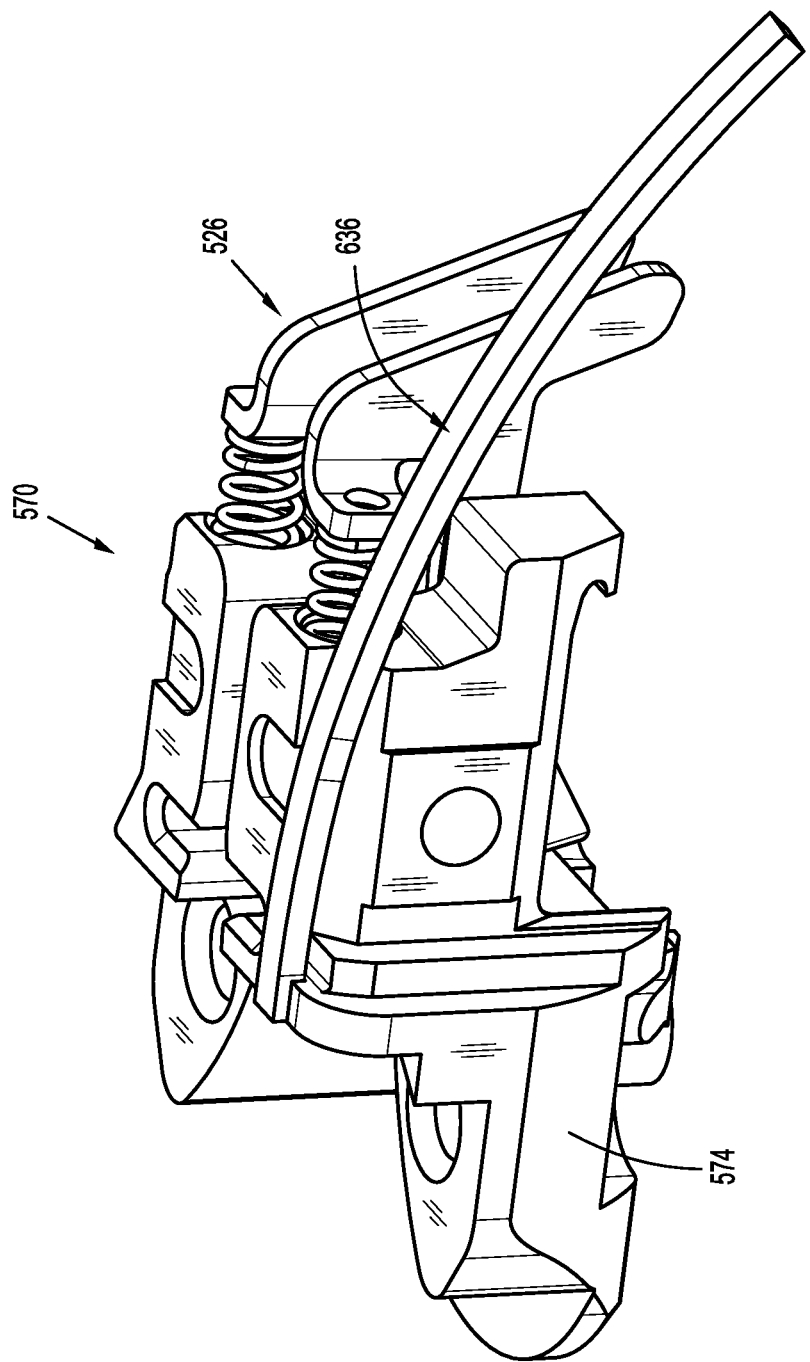
FIG. 55 is a perspective side view of the mounting assembly shown in FIG. 35.

Turning now to FIG. 55, a distal end of the flexible cable "R4" is received within a proximal slot 603' of a connector housing 604' of a connector assembly 602' and is heat staked within the connector housing 604'. A first contact member 608a' is press fit within a first distal slot 603a' of the connector housing 604' and a second contact member 608b' is press fit within a second distal slot 603b' of the connector housing 604' to electrically couple the first and second contact members 608a', 608b' with the distal end of the flexible cable "R4". A distal portion of the flexible cable "R4" includes a collar "C" to restrain and support the flexible cable "R4" with the connector housing 604'.

Figure 56:
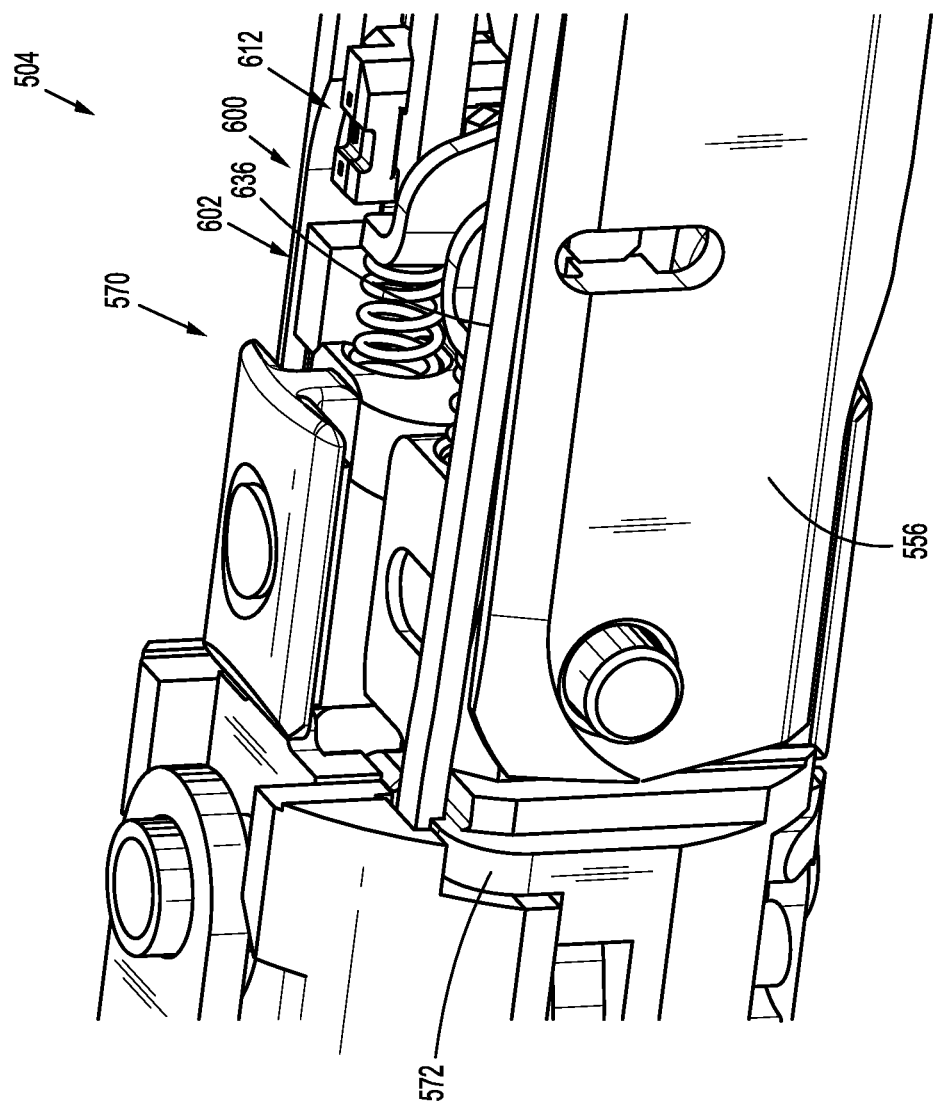
FIG. 56 is a perspective side view of a proximal end of the tool assembly of the loading unit shown in FIG. 33, with an anvil assembly removed.

With reference to FIGS. 55 and 56, as noted above, the leaf spring 636 of the mounting assembly 570 of the loading unit 500 is secured to the lower mounting portion 574 of the mounting assembly 570 using, for example, adhesive, welding, or mechanical fasteners. The leaf spring 636 engages the jaw member 556 of the tool assembly 504 to urge the tool assembly 504 to the unapproximated position (FIG. 33).

Figure 57:
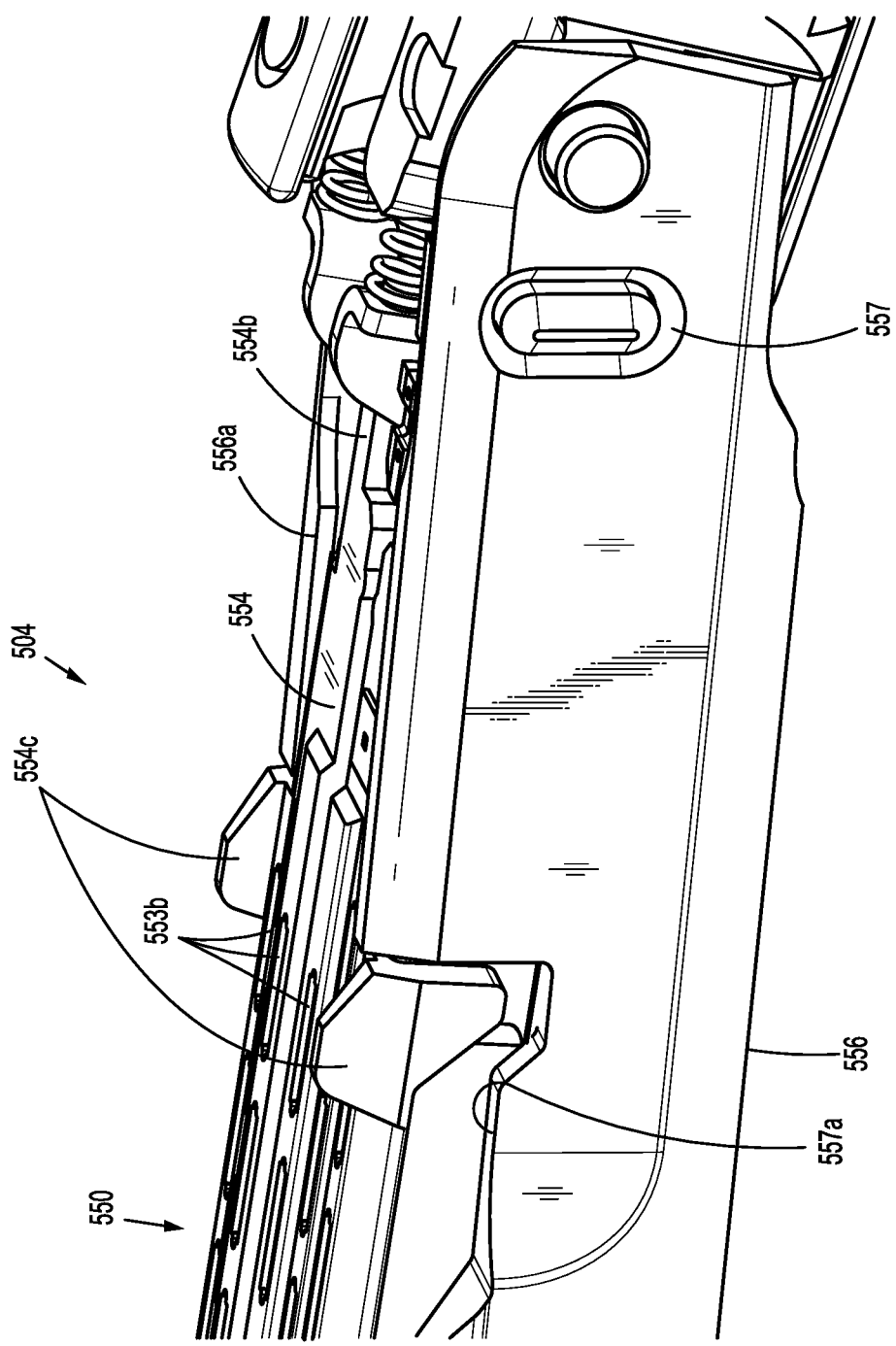
FIG. 57 is a perspective side view of the proximal end of the tool assembly of the loading unit shown in FIG. 33 during loading of a cartridge assembly.

With reference to FIG. 57, the jaw member 556 of the tool assembly 504 includes a rail member 556a along a proximal end thereof. The rail member 556a engages a proximal portion of the cartridge body 554 of the cartridge assembly 550 as the cartridge assembly 550 is received within the jaw member 556 of the tool assembly 504 to limit the angle at which the cartridge assembly 550 can be loaded into the jaw member 556. As shown, the cartridge body 554 includes a proximal extension 554b for engaging the rail member 556a of the jaw member 556. Limiting the angle at which the cartridge assembly 550 can be loaded in the jaw member 556 facilitates proper engagement between the chip assembly 612 (FIG. 56) of the identification assembly 600 (FIG. 56) in the cartridge assembly 550 and the connector assembly 602 of the identification assembly 600 in the jaw member 556. The jaw member 556 further includes a stop features 556b (FIG. 44) for preventing over-insertion of the cartridge assembly 550 within the jaw member 556.

With continued reference to FIG. 56, the cartridge body 554 includes a tissue stop 554c which prevents tissue (not shown) from being positioned proximally of the staple retention slots 553b. Receipt of the tissue stop 554c within a notch 557a formed in the jaw member 556 provides indication that the cartridge assembly 550 is fully inserted and properly seated within the jaw member 556.

Figure 58:
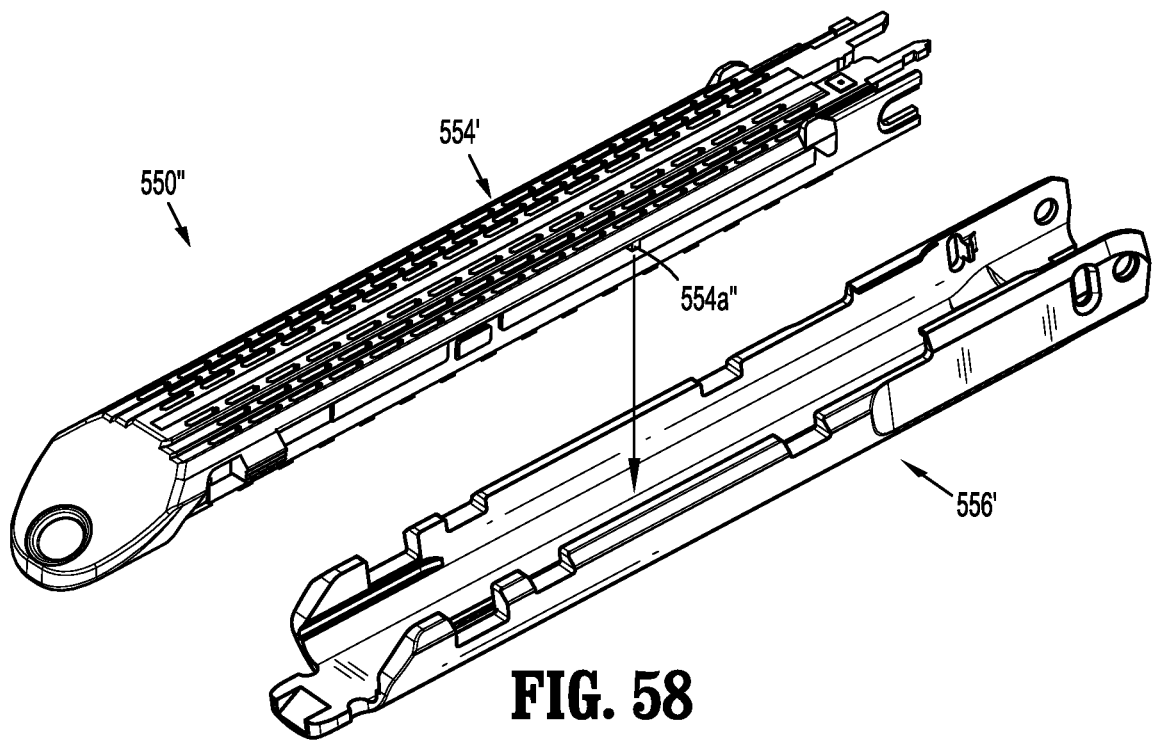
FIG. 58 is a perspective view of a cartridge body of a cartridge assembly having a first length and a jaw member of a second length.
Figure 59:
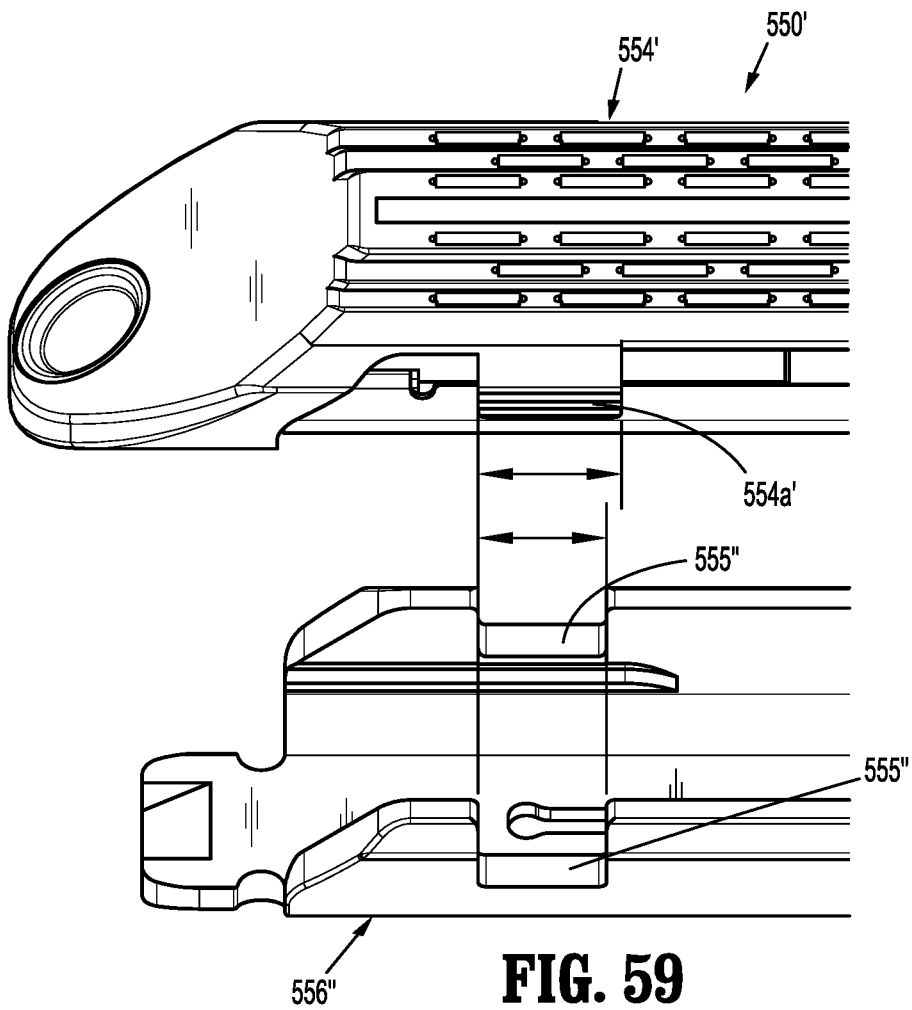
FIG. 59 is a perspective view of a cartridge body of a cartridge assembly having a the second length and a jaw member of the first length.

With reference now to FIGS. 58 and 59, the loading units of the present disclosure may be provided with staple cartridges of different sizes. For example, a first cartridge assembly 550' (FIG. 59) is forty-five millimeters (45 mm) in length and a second cartridge assembly 550" (FIG. 59) is sixty millimeters (60 mm) in length. Receipt of the first cartridge assembly 550' in a second jaw member 556" (FIG. 59) configured to receive the second cartridge assembly 550" or receipt of the second cartridge assembly 550" in a first jaw member 556' (FIG. 58) configured to receive the first cartridge assembly 550' may result in malfunctioning of the loading unit, e.g., misfiring.

To prevent loading of the first cartridge assembly 550' in the second jaw member 556", a cartridge body 554' of the first cartridge assembly 550' includes opposed tabs 554a' which are larger than opposed cutouts 555" in the second jaw member 556". In the event that the first cartridge assembly 550' is inadvertently loaded into the second jaw member 556", the opposed tabs 554a' of the cartridge body 554' of the first cartridge assembly 550' will prevent the first cartridge assembly 550' from properly seating in the second jaw member 556". Similarly, the cartridge body 554" of the second cartridge assembly 550" includes opposed tabs 554a" and the first jaw member 556' is devoid of opposed cutouts for receiving the opposed tabs 554". Accordingly, in the event the second cartridge assembly 550' is inadvertently loaded into the first jaw member 556', the opposed tabs 554a" of the cartridge body 554" will prevent the second cartridge assembly 550" from properly seating in the first jaw member 556'.

With reference to FIGS. 60 and 61, a shipping wedge according to an embodiment of the present disclosure is shown generally as shipping wedge 700. The shipping wedge 700 is substantially similar to the shipping wedge 300 described hereinabove. The shipping wedge 700 is configured to selectively engage the cartridge assembly 550.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

The invention claimed is:

1. An electrical conductor for use in a surgical instrument, the electrical conductor comprising:
   a proximal portion configured for electrical connection with a handle assembly;
   a distal portion configured for electrical connection with an identification assembly; and
   a strain relief portion disposed between the proximal portion and the distal portion having an initial condition, a compressed condition, and a tensed condition, the strain relief portion having a first length in the initial condition, a second length in the compressed condition, and a third length in the tensed condition, wherein the first length is longer than the second length and shorter than the third length.

2. The electrical conductor of claim 1, wherein the strain relief portion includes a plurality of coils having a height.

3. The electrical conductor of claim 2, wherein the height of the plurality of coils decreases from a proximal portion of the plurality of coils to a distal portion of the plurality of coils.

4. The electrical conductor of claim 2, wherein the height of the plurality of coils is uniform from a proximal portion of the plurality of coils to a distal portion of the plurality of coils.

5. The electrical conductor of claim 2, wherein the height of the plurality of coils increases from a proximal portion of the plurality of coils to distal portion of the plurality of coils.

6. The electrical conductor of claim 2, wherein the plurality of coils are uniformly spaced along the strain relief portion.

7. The electrical conductor of claim 1, further including a connector housing secured to the distal portion.

8. The electrical conductor of claim 1, wherein the distal portion includes first and second contact members.

9. The electrical conductor of claim 1, further including a connector member secured to the proximal portion.

10. The electrical conductor of claim 1, further including an adhesive backing disposed along the proximal portion.

11. The electrical conductor of claim 1, further including stiffener portion disposed along the proximal portion.

12. The electrical conductor of claim 1, further including a connection assembly having first and second posts, wherein the proximal portion defines first and second openings for receiving the respective first and second posts.

13. The electrical conductor of claim 1, wherein the distal portion includes a collar.

14. An electrical conductor for use in a surgical instrument, the electrical conductor comprising:
   a proximal portion configured for electrical connection with a handle assembly;
   a distal portion configured for electrical connection with an identification assembly; and
   a strain relief portion disposed between the proximal portion and the distal portion having a compressed condition and a tensed condition, the strain relief portion having a first length in the compressed condition and a second length in the tensed condition, wherein the second length is longer than the first length.

15. The electrical conductor of claim 14, wherein the strain relief portion includes a plurality of coils having a height.

16. The electrical conductor of claim 15, wherein the height of the plurality of coils decreases from a proximal portion of the plurality of coils to a distal portion of the plurality of coils.

17. The electrical conductor of claim 15, wherein the height of the plurality of coils is uniform from a proximal portion of the plurality of coils to a distal portion of the plurality of coils.

18. An electrical conductor for use in a surgical instrument, the electrical conductor comprising:
   a proximal portion configured for electrical connection with a handle assembly;
   a distal portion configured for electrical connection with an identification assembly; and
   a strain relief portion disposed between the proximal portion and the distal portion having an initial condition, a compressed condition, and a tensed condition, the strain relief portion having a first length in the initial condition, a second length in the compressed condition, and a third length in the tensed condition, wherein the second length is shorter than the third length.

19. The electrical conductor of claim 18, wherein the strain relief portion includes a plurality of coils having a height.

20. The electrical conductor of claim 19, wherein the height of the plurality of coils decreases from a proximal portion of the plurality of coils to a distal portion of the plurality of coils.

21. The electrical conductor of claim 19, wherein the height of the plurality of coils is uniform from a proximal portion of the plurality of coils to a distal portion of the plurality of coils.

\* \* \* \* \*